United States Patent
Bala et al.

(10) Patent No.: US 7,666,878 B2
(45) Date of Patent: Feb. 23, 2010

(54) PYRROLOPYRIDINE DERIVATIVES AND THEIR USE AS CRTH2 ANTAGONISTS

(75) Inventors: Kamlesh Jagdis Bala, Horsham (GB); Catherine Leblanc, Horsham (GB); David Andrew Sandham, Horsham (GB); Katharine Louise Turner, Horsham (GB); Simon James Watson, Horsham (GB); Lyndon Nigel Brown, Lower Beeding (GB); Brian Cox, Horsham (GB)

(73) Assignee: Novartis AG, Basel (CH)

( * ) Notice: Subject to any disclaimer, the term of this patent is extended or adjusted under 35 U.S.C. 154(b) by 39 days.

(21) Appl. No.: 11/597,781

(22) PCT Filed: Jun. 16, 2005

(86) PCT No.: PCT/EP2005/006493

§ 371 (c)(1),
(2), (4) Date: Aug. 24, 2007

(87) PCT Pub. No.: WO2005/123731

PCT Pub. Date: Dec. 29, 2005

(65) Prior Publication Data

US 2008/0114022 A1    May 15, 2008

(30) Foreign Application Priority Data

Jun. 17, 2004 (GB) ............................ 0413619.8
Apr. 15, 2005 (GB) ............................ 0507693.0

(51) Int. Cl.
*C07D 471/02* (2006.01)
*A61K 31/4745* (2006.01)

(52) U.S. Cl. ..................... 514/300; 546/112
(58) Field of Classification Search ............... 514/300; 546/112
See application file for complete search history.

(56) References Cited

U.S. PATENT DOCUMENTS

| 5,212,195 | A | 5/1993 | Clark et al. | |
| 6,248,753 | B1 | 6/2001 | Chen | |
| 2008/0287416 | A1* | 11/2008 | Sandham et al. | 514/210.21 |
| 2008/0312229 | A1* | 12/2008 | Sandham et al. | 514/234.5 |
| 2008/0312230 | A1* | 12/2008 | Sandham | 514/234.5 |

FOREIGN PATENT DOCUMENTS

| EP | 1 424 325 | 6/2004 |
| EP | 1 505 061 | 2/2005 |
| WO | 9507910 | * 3/1995 |
| WO | WO 95/07910 | 3/1995 |
| WO | WO 95/33748 | 12/1995 |
| WO | WO 02/34747 A1 | 5/2002 |
| WO | WO 03/066047 | 8/2003 |
| WO | WO 2004/007451 | 1/2004 |
| WO | WO 2005/040112 | 5/2005 |
| WO | WO 2005/121141 | 12/2005 |

OTHER PUBLICATIONS

Andrew Brodrick et al, "1H-Pyrrolo[2,3-b]pyridines. Part III. A Novel Synthetic Route From 1-Substituted 2-Aminopyrroles" J. Organic Chemistry 19:1910-1913, 1975.
Anthony Verbiscar, "Synthesis of 1-p-Chlorobenzy1-7-azaindole-3-alpha-piperidylmethanol as a Potential Antimalarial Agent" J. Medicinal Chemistry 15(2):149-152, 1975.
Adberrahim Mouaddib et al., "Synthesis of Indolo[3,2-c]quinoline and Pyrido[3',2':4,5][3,2-c]quinoline Derivatives" Synthesis 4:549-556, 2000.
Adberrahim Mouaddib et al., "Synthesis of Benzo[5'6']cyclohepta[4,5] pyrrolo[2,3-beta]pyridin-12-one" Tetrahedron Letters 40:5853-5854, 1999.
C. Nicholas Hodge et al., "Corticotropin-Releasing Hormone Receptor Antagonists: Framework Design and Synthesis Guided . . . " J. Med. Chem. 42:819-832, 1999.
Yakhontov et al., Khimiya Geterotsiklicheskikh Soedinenii 1:141-144, 1967.
Yakhonotov et al., Biol. Aktivn. Soedin, Akad. Nauk SSSR pp. 83-90, 1965.

* cited by examiner

*Primary Examiner*—D. Margaret Seaman
*Assistant Examiner*—Niloofar Rahmani
(74) *Attorney, Agent, or Firm*—Vinit Kathardekar; Mark Milstead

(57) ABSTRACT

There are provided according to the invention compounds of formula (I),

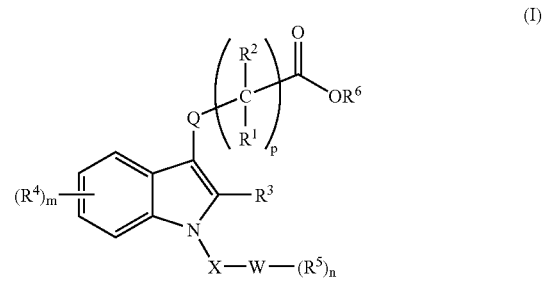

in free or salt form, wherein R1, R2, R3, R 4, R5, R6, Q, W, X, m, n and p are as described in the specification, process for preparing them, and their use as pharmaceuticals.

13 Claims, No Drawings

PYRROLOPYRIDINE DERIVATIVES AND THEIR USE AS CRTH2 ANTAGONISTS

The present invention relates to organic compounds, their preparation and their use as pharmaceuticals.

In a first aspect, the present invention provides compounds of formula (I)

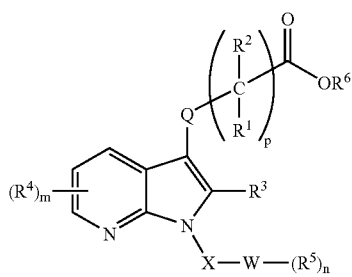

in free or salt form, wherein

Q is a bond or a $C_1$-$C_{10}$-alkylene group optionally substituted by halogen;

$R^1$ and $R^2$ are, independently, H, halogen or $C_1$-$C_8$-alkyl, or $R^1$ and $R^2$, together with the carbon atom to which they are attached, form a divalent $C_3$-$C_8$-cycloaliphatic group;

$R^3$ is H, $C_1$-$C_8$-alkyl, a $C_3$-$C_{15}$-carbocyclic group, $C_1$-$C_8$-haloalkyl, alkoxy $C_1$-$C_8$ alkyl, $C_1$-$C_8$-hydroxyalkyl;

$R^4$ and $R^5$ are, independently, halogen, $C_1$-$C_8$-alkyl, $C_1$-$C_8$-haloalkyl, a $C_3$-$C_{15}$-carbocyclic group, nitro, cyano, $C_1$-$C_8$-alkylsulfonyl, $C_1$-$C_8$-alkylsulfinyl, $C_1$-$C_8$-alkylcarbonyl, $C_1$-$C_8$-alkoxycarbonyl, $C_1$-$C_8$-alkoxy, $C_1$-$C_8$-haloalkoxy, carboxy, carboxy-$C_1$-$C_8$-alkyl, amino, $C_1$-$C_8$-alkylamino, di($C_1$-$C_8$-alkyl)amino, $SO_2NH_2$, ($C_1$-$C_8$-alkylamino)sulfonyl, di($C_1$-$C_8$-alkyl)aminosulfonyl, aminocarbonyl, $C_1$-$C_8$-alkylaminocarbonyl, di($C_1$-$C_8$-alkyl)aminocarbonyl or a 4- to 10-membered heterocyclic group having one or more heteroatoms selected from the group consisting of oxygen, nitrogen and sulphur;

$R^6$ is H or $C_1$-$C_8$-alkyl;

W is a $C_6$-$C_{15}$-aromatic carbocyclic group or a 4- to 10-membered heterocyclic group containing at least one ring heteroatom selected from the group consisting of nitrogen, oxygen and sulphur;

X is $-SO_2-$, $-CH_2-$, $-CON(C_1$-$C_8$-alkyl)-, $-CH(C_1$-$C_8$-alkyl)- or a bond;

m and n are each, independently, an integer from 0-3; and p is 1.

Terms used in the specification have the following meanings:

"Optionally substituted", as used herein, means the group referred to can be substituted at one or more positions by any one or any combination of the radicals listed thereafter.

"Halogen" or "halo" may be fluorine, chlorine, bromine or iodine; preferably it is bromine or chlorine or fluorine.

"$C_1$-$C_8$-alkyl" denotes straight-chain or branched $C_1$-$C_8$-alkyl, which may be, e.g., methyl, ethyl, n-propyl, isopropyl, n-butyl, isobutyl, sec-butyl, tert-butyl, straight- or branched-pentyl, straight- or branched-hexyl, straight- or branched-heptyl or straight- or branched-octyl. Preferably, $C_1$-$C_8$-alkyl is $C_1$-$C_4$-alkyl.

"$C_3$-$C_{15}$-carbocyclic group", as used herein, denotes a carbocyclic group having 3- to 15-ring carbon atoms, e.g., a monocyclic group, either cycloaliphatic, such as a $C_3$-$C_8$-cycloalkyl, e.g., cyclopropyl, cyclobutyl, cyclopentyl, cyclohexyl, cycloheptyl or cyclooctyl; or aromatic, such as phenyl; or a bicyclic group, such as bicyclooctyl, bicyclononyl including indanyl and indenyl, and bicyclodecyl including naphthyl. Preferably the $C_3$-$C_{15}$-carbocyclic group is a $C_3$-$C_{10}$-carbocyclic group, e.g., phenyl or naphthyl. The $C_3$-$C_{15}$-carbocyclic group can be substituted with 1-3 substituents or unsubstituted. Preferred substituents include halo, cyano, amino, nitro, carboxy, $C_1$-$C_8$-alkyl, $C_1$-$C_8$-haloalkyl, $C_1$-$C_8$-alkoxy, $C_1$-$C_8$-alkylcarbonyl, $C_1$-$C_8$-alkylsulfonyl, $-SO_2NH_2$, ($C_1$-$C_8$-alkylamino)-sulfonyl, di($C_1$-$C_8$-alkyl)aminosulfonyl, aminocarbonyl, $C_1$-$C_8$-alkylaminocarbonyl and di($C_1$-$C_8$-alkyl)aminocarbonyl, a $C_3$-$C_{10}$-carbocyclic group and a 5- to 12-membered heterocyclic group having at least one ring heteroatom selected from nitrogen, oxygen and sulphur.

"$C_6$-$C_{15}$-aromatic carbocyclic group", as used herein, denotes an aromatic group having 6- to 15-ring carbon atoms, e.g., phenylene, naphthylene or anthrylene. The $C_6$-$C_{15}$-aromatic group can be substituted with 1-3 substituents or can be unsubstituted. Preferred substituents include halo, cyano, amino, nitro, carboxy, $C_1$-$C_8$-alkyl, halo-$C_1$-$C_8$-alkyl, $C_1$-$C_8$-alkoxy, $C_1$-$C_8$-alkylcarbonyl, $C_1$-$C_8$-alkylsulfonyl, $-SO_2NH_2$, ($C_1$-$C_8$-alkylamino)-sulfonyl, di($C_1$-$C_8$-alkyl) aminosulfonyl, aminocarbonyl, $C_1$-$C_8$-alkylaminocarbonyl and di($C_1$-$C_8$-alkyl)aminocarbonyl, a $C_3$-$C_{15}$-carbocyclic group and a 5- to 12-membered heterocyclic group having at least one ring heteroatom selected from nitrogen, oxygen and sulphur.

"Divalent $C_3$-$C_8$-cycloaliphatic" denotes cycloalkylene having 3- to 8-ring carbon atoms, e.g., a monocyclic group, such as a cyclopropylene, cyclobutylene, cyclopentylene, cyclohexylene, cycloheptylene or cyclooctylene, any of which can be substituted by one or more, usually one or two, $C_1$-$C_4$-alkyl groups; or a bicyclic group, such as bicycloheptylene or bicyclooctylene. Preferably "$C_3$-$C_8$-cycloalkylene" is $C_3$-$C_5$-cycloalkylene, e.g., cyclo-propylene, cyclobutylene or cyclopentylene.

"$C_1$-$C_8$-alkoxy" denotes straight-chain or branched $C_1$-$C_8$-alkoxy which may be, e.g., methoxy, ethoxy, n-propoxy, isopropoxy, n-butoxy, isobutoxy, sec-butoxy, tert-butoxy, straight- or branched-pentoxy, straight- or branched-hexyloxy, straight- or branched-heptyloxy or straight- or branched-octyloxy. Preferably, $C_1$-$C_8$-alkoxy is $C_1$-$C_4$-alkoxy.

"$C_1$-$C_8$-haloalkyl" and "$C_1$-$C_8$-haloalkoxy" denote $C_1$-$C_8$-alkyl and $C_1$-$C_8$-alkoxy as hereinbefore defined substituted by one or more halogen atoms, preferably one, two or three halogen atoms, preferably fluorine, bromine or chlorine atoms. Preferably, $C_1$-$C_8$-haloalkyl is $C_1$-$C_4$-alkyl substituted by one, two or three fluorine, bromine or chlorine atoms. Preferably, $C_1$-$C_8$-haloalkoxy is $C_1$-$C_4$-alkoxy substituted by one, two or three fluorine, bromine or chlorine atoms.

"$C_1$-$C_8$-alkylsulfonyl", as used herein, denotes $C_1$-$C_8$-alkyl as hereinbefore defined linked to $-SO_2-$. Preferably $C_1$-$C_8$-alkylsulfonyl is $C_1$-$C_4$-alkylsulfonyl, especially methylsulfonyl.

"$C_1$-$C_8$-alkylsulfinyl", as used herein, denotes $C_1$-$C_8$-alkyl as hereinbefore defined linked to $-SO-$. Preferably $C_1$-$C_8$-alkylsulfinyl is $C_1$-$C_4$-alkylsulfinyl, especially methylsulfinyl.

"Amino-$C_1$-$C_8$-alkyl" and "amino-$C_1$-$C_8$-alkoxy" denote amino attached by a nitrogen atom to $C_1$-$C_8$-alkyl, e.g., $NH_2-(C_1$-$C_8)-$, or to $C_1$-$C_8$-alkoxy, e.g., $NH_2-(C_1$-$C_8)-O-$, respectively, as hereinbefore defined. Preferably, amino-$C_1$-$C_8$-alkyl and amino-$C_1$-$C_8$-alkoxy are, respectively, amino-$C_1$-$C_4$-alkyl and amino-$C_1$-$C_4$-alkoxy.

"Amino-(hydroxy)-$C_1$-$C_8$-alkyl" denotes amino attached by a nitrogen atom to $C_1$-$C_8$-alkyl and hydroxy attached by an oxygen atom to the same $C_1$-$C_8$-alkyl. Preferably, amino-(hydroxy)-$C_1$-$C_8$-alkyl is amino-(hydroxy)-$C_2$-$C_4$-alkyl.

"Carboxy-$C_1$-$C_8$-alkyl" and "carboxy-$C_1$-$C_8$-alkoxy" denote carboxy attached by a carbon atom to $C_1$-$C_8$-alkyl or $C_1$-$C_8$-alkoxy, respectively, as hereinbefore defined. Preferably, carboxy-$C_1$-$C_8$-alkyl and carboxy-$C_1$-$C_8$-alkoxy are, respectively, carboxy-$C_1$-$C_4$-alkyl and carboxy-$C_1$-$C_4$-alkoxy.

"$C_1$-$C_8$-alkylcarbonyl", "$C_1$-$C_8$-alkoxycarbonyl" and "$C_1$-$C_8$-haloalkylcarbonyl" denote $C_1$-$C_8$-alkyl, $C_1$-$C_8$-alkoxy or $C_1$-$C_8$-haloalkyl, respectively, as hereinbefore defined attached by a carbon atom to a carbonyl group. "$C_1$-$C_8$-alkoxycarbonyl" denotes $C_1$-$C_8$-alkoxy as hereinbefore defined wherein the oxygen of the alkoxy group is attached to the carbonyl carbon. Preferably, $C_1$-$C_8$-alkylcarbonyl, $C_1$-$C_8$-alkoxycarbonyl and $C_1$-$C_8$-haloalkylcarbonyl are, respectively, $C_1$-$C_4$-alkylcarbonyl, $C_1$-$C_4$-alkoxycarbonyl and $C_1$-$C_4$-haloalkylcarbonyl.

"$C_1$-$C_8$-alkylamino" and "di($C_1$-$C_8$-alkyl)amino" denote $C_1$-$C_8$-alkyl as hereinbefore defined attached by a carbon atom to an amino group. The $C_1$-$C_8$-alkyl groups in di($C_1$-$C_8$-alkyl)amino may be the same or different. Preferably, $C_1$-$C_8$-alkylamino and di($C_1$-$C_8$-alkyl)amino are, respectively, $C_1$-$C_4$-alkylamino and di($C_1$-$C_4$-alkyl)amino.

"$C_1$-$C_8$-alkylaminocarbonyl" and "di($C_1$-$C_8$-alkyl)aminocarbonyl" denote $C_1$-$C_8$-alkylamino and di($C_1$-$C_8$-alkyl)amino, respectively, as hereinbefore defined attached by a nitrogen atom to the carbon atom of a carbonyl group. Preferably, $C_1$-$C_8$-alkylaminocarbonyl and di($C_1$-$C_8$-alkyl)-aminocarbonyl are, respectively, $C_1$-$C_4$-alkylaminocarbonyl and di($C_1$-$C_4$-alkyl)-aminocarbonyl.

"Di($C_1$-$C_8$-alkyl)amino-$C_1$-$C_8$-alkyl" and "di($C_1$-$C_8$-alkyl)amino-$C_1$-$C_8$-alkoxy" denote di($C_1$-$C_8$-alkyl)amino as hereinbefore defined attached by a nitrogen atom to the carbon atom of a $C_1$-$C_8$-alkyl or a $C_1$-$C_8$-alkoxy group, respectively. Preferably, di($C_1$-$C_8$-alkyl)-amino-$C_1$-$C_8$-alkyl and di($C_1$-$C_8$-alkyl)amino-$C_1$-$C_8$-alkoxy are, respectively, di($C_1$-$C_4$-alkyl)-amino-$C_1$-$C_4$-alkyl and di($C_1$-$C_4$-alkyl)amino-$C_1$-$C_4$-alkoxy.

"4- to 10-membered heterocyclic group containing at least one ring heteroatom selected from the group consisting of nitrogen, oxygen and sulphur", as used herein, may be monocyclic or bicyclic, e.g., furan, tetrahydrofuran, pyrrole, pyrrolidine, pyrazole, imidazole, triazole, isotriazole, tetrazole, thiadiazole, isothiazole, oxadiazole, pyridine, oxazole, isoxazole, pyrazine, pyridazine, pyrimidine, piperidine, piperazine, morpholine, triazine, oxazine, thiazole, quinoline, isoquinoline, benzothiophene, benzoxazole, benzisoxazole, benzothiazole, benzisothiazole, benzofuran, indole, indazole or benzimidazole. Preferred heterocyclic groups include piperazine, morpholine, imidazole, isotriazole, pyrazole, pyridine, furan, oxazole, isoxazole, thiazole, tetrazole, benzothiophene, benzoxazole, benzothiazole and benzofuran. The 4- to 10-membered heterocyclic group can be unsubstituted or substituted. Preferred substituents include halo, cyano, oxo, hydroxy, carboxy, nitro, $C_1$-$C_8$-alkyl, $C_1$-$C_8$-alkylcarbonyl, hydroxy-$C_1$-$C_8$-alkyl, $C_1$-$C_8$-haloalkyl, amino-$C_1$-$C_8$-alkyl, amino(hydroxy)$C_1$-$C_8$-alkyl and $C_1$-$C_8$-alkoxy optionally substituted by aminocarbonyl. Especially preferred substituents include halo, oxo, $C_1$-$C_4$-alkyl, $C_1$-$C_4$-alkylcarbonyl, hydroxy-$C_1$-$C_4$-alkyl, $C_1$-$C_4$-haloalkyl, amino-$C_1$-$C_4$-alkyl and amino(hydroxy)$C_1$-$C_4$-alkyl.

Throughout this specification and in the claims that follow, unless the context requires otherwise, the word "comprise", or variations, such as "comprises" or "comprising", will be understood to imply the inclusion of a stated integer or step or group of integers or steps but not the exclusion of any other integer or step or group of integers or steps.

Where in formula (I), m or n are 2, the two substituents may be the same or different. Where m or n are 3, two or all of the substituents may be the same, or all three may be different.

In another aspect, the present invention provides compounds of formula (L) in free or salt form, wherein Q is a bond or a $C_1$-$C_{10}$-alkylene group optionally substituted by halogen;

$R^1$ and $R^2$ are, independently, H, halogen or $C_1$-$C_8$-alkyl, or $R^1$ and $R^2$, together with the carbon atom to which they are attached, form a divalent $C_3$-$C_8$-cycloaliphatic group;

$R^3$ is H, $C_1$-$C_8$-alkyl, a $C_3$-$C_{15}$-carbocyclic group, $C_1$-$C_8$-haloalkyl, alkoxy $C_1$-$C_8$ alkyl, $C_1$-$C_8$-hydroxyalkyl;

$R^4$ and $R^5$ are, independently, halogen, $C_1$-$C_8$-alkyl, $C_1$-$C_8$-haloalkyl, a $C_3$-$C_{15}$-carbocyclic group, nitro, cyano, $C_1$-$C_8$-alkylsulfonyl, $C_1$-$C_8$-alkylsulfinyl, $C_1$-$C_8$-alkylcarbonyl, $C_1$-$C_8$-alkoxycarbonyl, $C_1$-$C_8$-alkoxy, $C_1$-$C_8$-haloalkoxy, carboxy, carboxy-$C_1$-$C_8$-alkyl, amino, $C_1$-$C_8$-alkylamino, di($C_1$-$C_8$-alkyl)amino, $SO_2NH_2$, ($C_1$-$C_8$-alkylamino)sulfonyl, di($C_1$-$C_8$-alkyl)aminosulfonyl, aminocarbonyl, $C_1$-$C_8$-alkylaminocarbonyl, di($C_1$-$C_8$-alkyl)aminocarbonyl or a 4- to 10-membered heterocyclic group having one or more heteroatoms selected from the group consisting of oxygen, nitrogen and sulphur;

$R^6$ is H or $C_1$-$C_8$-alkyl;

W is a $C_6$-$C_{15}$-aromatic carbocyclic group or a 4- to 10-membered heterocyclic group containing at least one ring heteroatom selected from the group consisting of nitrogen, oxygen and sulphur;

X is —$SO_2$—, —$CH_2$—, —$CON(C_1$-$C_8$-alkyl)-, —$CH(C_1$-$C_8$-alkyl)- or a bond;

m and n are each, independently, an integer from 0-3; and p is 1.

In another aspect, the present invention provides compounds of formula (I) in free or salt form, wherein Q is a bond;

$R^1$ and $R^2$ are, independently, H or $C_1$-$C_8$-alkyl;

$R^3$ is $C_1$-$C_8$-alkyl;

$R^4$ and $R^5$ are, independently, halogen, $C_1$-$C_8$-alkyl, $C_1$-$C_8$-haloalkyl, a $C_3$-$C_{15}$-carbocyclic group, nitro, cyano, $C_1$-$C_8$-alkylsulfonyl, $C_1$-$C_8$-alkoxycarbonyl, $C_1$-$C_8$-alkoxy or $C_1$-$C_8$-haloalkoxy;

$R^6$ is H or $C_1$-$C_8$-alkyl;

W is a group of formula ($W_{a1}$) or ($W_{a2}$)

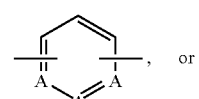

($W_{a1}$)

or

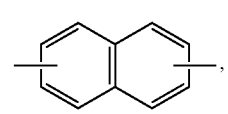

($W_{a2}$)

wherein A is, independently, C or N, or
W is a group of formula ($W_b$);

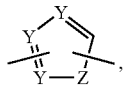  ($W_b$)

wherein
Y is, independently, C or N; and
Z is N, O or S, or
W is a group of formula ($W_c$)

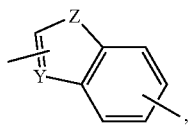  ($W_c$)

wherein
Y is, independently, C or N; and
Z is O or S;
X is —$SO_2$—, —$CH_2$—, —CH($C_1$-$C_8$-alkyl)-, —CON($C_1$-$C_8$-alkyl)- or a bond;
m and n are each, independently, an integer from 0-3; and
p is 1.

In yet another aspect, the present invention provides compounds of formula (I) in free or salt form, wherein
Q is a bond;
$R^1$ and $R^2$ are, independently, H or $C_1$-$C_4$-alkyl;
$R^3$ is $C_1$-$C_4$-alkyl;
$R^4$ and $R^5$ are, independently, halogen, $C_1$-$C_4$-alkyl, $C_1$-$C_4$-haloalkyl, cyano, $C_3$-$C_{10}$-carbocyclic group, $C_1$-$C_4$-alkoxycarbonyl, $C_1$-$C_4$-alkylsulfonyl, $C_1$-$C_4$-alkoxy or $C_1$-$C_4$-haloalkoxy;
$R^6$ is H or $C_1$-$C_4$-alkyl;
W is a group of formula ($W_{a1}$) or ($W_{a2}$)

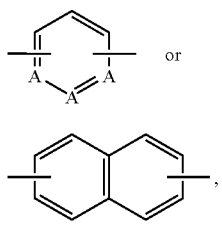  ($W_{a1}$) or ($W_{a2}$)

wherein
one A is C or N; and
the other two are each C, or
W is a group of formula ($W_b$)

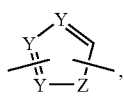  ($W_b$)

wherein
Y is, independently, C or N; and
Z is N, O or S;
X is —$SO_2$—, —$CH_2$— or —CH($C_1$-$C_4$-alkyl)-;
m and n are each, independently, an integer from 0-3; and
p is 1.

In a yet further aspect, the present invention provides for the use of a compound of formula (I) in any of the aforementioned embodiments, in free or salt form, for the manufacture of a medicament for the treatment of an inflammatory or allergic condition, particularly an inflammatory or obstructive airways disease.

Salts and Isomers

Many of the compounds represented by formula (I) are capable of forming acid addition salts, particularly pharmaceutically acceptable acid addition salts. Pharmaceutically acceptable acid addition salts of the compound of formula (I) include those of inorganic acids, e.g., hydrohalic acids, such as hydrochloric acid or hydrobromic acid; nitric acid; sulphuric acid; phosphoric acid; and organic acids, e.g., aliphatic monocarboxylic acids, such as formic acid, acetic acid, diphenylacetic acid, triphenylacetic acid, caprylic acid, dichloroacetic acid, trifluoroacetic acid, hippuric acid, propionic acid and butyric acid; aliphatic hydroxy acids, such as lactic acid, citric acid, gluconic acid, mandelic acid, tartaric acid or malic acid; dicarboxylic acids, such as adipic acid, aspartic acid, fumaric acid, glutamic acid, maleic acid, malonic acid, sebacic acid or succinic acid; aromatic carboxylic acids, such as benzoic acid, p-chlorobenzoic acid, or nicotinic acid; aromatic hydroxy acids, such as o-hydroxybenzoic acid, p-hydroxybenzoic acid, 1-hydroxynaphthalene-2-carboxylic acid or 3-hydroxynaphthalene-2-carboxylic acid; and sulfonic acids, such as ethanesulfonic acid, ethane-1,2-disulfonic acid, 2-hydroxyethane-sulfonic acid, methanesulfonic acid, (+)-camphor-10-sulfonic acid, benzenesulfonic acid, naphthalene-2-sulfonic acid, naphthalene-1,5-disulfonic acid or p-toluenesulfonic acid. These salts may be prepared from compounds of formula (I) by known salt-forming procedures.

Compounds of formula (I) which contain acidic, e.g., carboxyl, groups, are also capable of forming salts with bases, in particular, pharmaceutically acceptable bases, such as those well-known in the art; suitable such salts include metal salts, particularly, alkali metal or alkaline earth metal salts, such as sodium, potassium, magnesium, calcium or zinc salts; or salts with ammonia or pharmaceutically acceptable organic amines or heterocyclic bases, such as benethamine, benzathine, diethanolamine, ethanolamine, 4(2-hydroxy-ethyl)morpholine, 1-(2-hydroxyethyl)pyrrolidine, N-methyl glucamine, piperazine, triethanol-amine or tromethamine. These salts may be prepared from compounds of formula (I) by known salt-forming procedures.

In those compounds where there is an asymmetric carbon atom or an axis of chirality the compounds exist in individual optically active isomeric forms or as mixtures thereof, e.g., as racemic or diastereomeric mixtures. The present invention embraces both individual optically active R and S isomers, as well as mixtures, e.g., racemic or diastereomeric mixtures, thereof.

Specific preferred compounds of formula (I) are described hereinafter in the Examples.

The invention also provides a process for the preparation of compounds of formula (I), in free or salt form, which comprises the steps of:
(i) (A) for the preparation of compounds of formula (I), wherein $R^6$ is H, cleaving the ester group —$COOR^6$ in a compound of formula (I),

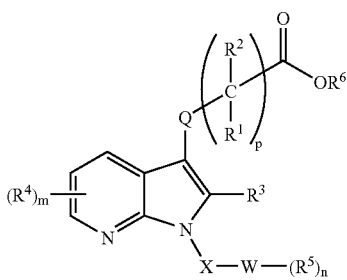

where $R^6$ is $C_1$-$C_8$-alkyl and Q, $R^1$, $R^2$, $R^3$, $R^4$, $R^5$, W, X, m, n and p are as hereinbefore defined; or (B) for the preparation of compounds of formula (I), wherein $R^6$ is $C_1$-$C_8$-alkyl, reacting a compound of formula (II)

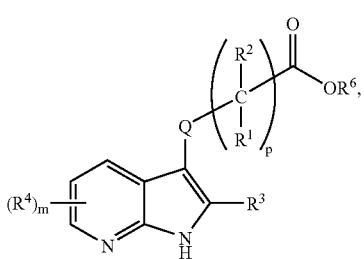

wherein
$R^6$ is $C_1$-$C_8$-alkyl; and
Q, $R^1$, $R^2$, $R^3$, $R^4$, m, n and p are as hereinbefore defined
with a compound of formula (III)

wherein
G is a leaving moiety, e.g., a halogen atom or an arylsulfonate group; and
$R^5$, W, X and n are as hereinbefore defined; or
(C) for the preparation of compounds of formula (I), wherein
$R^6$ is $C_1$-$C_8$-alkyl;
$R^1$ is H or $C_1$-$C_8$-alkyl;
$R^2$ is $C_1$-$C_8$-alkyl; and
p is 1, reacting a compound of formula (I),
where
$R^1$ is H or $C_1$-$C_8$-alkyl; and
$R^2$ is H, with a compound of formula $R^4$G,
where
$R^4$ is $C_1$-$C_8$-alkyl; and
G is as hereinbefore defined; and
(ii) recovering the resultant compound of formula (I) in free or salt form.

Process variant (A) may be carried out using known methods (or analogously as hereinafter described in the Examples) for cleavage of carboxylic ester groups and can be carried out in situ after preparation of a compound of formula (I), where $R^6$ is $C_1$-$C_8$-alkyl. For example, the compound of formula (I), where $R^6$ is $C_1$-$C_8$-alkyl, which is conveniently in solution in a polar organic solvent or a mixture thereof with water, may be reacted with an aqueous inorganic base, such as NaOH or LiOH to hydrolyse the ester group; where the base is NaOH, the reaction may be carried out at a temperature of 10-40° C., conveniently ambient temperature, while when the base is LiOH the reaction may be started at −5° C. to 5° C. and then continued at 10-40° C., conveniently ambient temperature. Alternatively, the compound of formula (I), where $R^6$ is $C_1$-$C_8$-alkyl, which is conveniently in solution in an organic solvent, such as $CH_2Cl_2$, may be reacted with a Lewis acid, such as boron tribromide to effect ester cleavage; the reaction may conveniently be carried out at 50-60° C., e.g., with the aid of microwave irradiation.

Process variant (B) may be carried out using known procedures or analogously as hereinafter described in the Examples. For example, the compound of formula (II) may be reacted with a sulfonyl halide of formula (III),
where
G is halogen;
X is —$SO_2$—; and
$R^5$, W and n are as hereinbefore defined, in the presence of an organic base, such as 2-tert-butylimino-1,3-dimethyl-2 lambda*5*-[1,3,2]diazaphosphinan-2-yl)-diethyl-amine (BEMP); the reaction may be carried out in an organic solvent, e.g., a polar aprotic solvent, such as N,N-dimethylformamide (DMF) and may be carried out at 10-40° C., conveniently at ambient temperature. In another example, the compound of formula (II) may be reacted with a compound of formula (III),
where
G is halogen;
X is —$CH_2$—; and
$R^5$, W and n are as hereinbefore defined, in the presence of an organic base, such as BEMP, e.g., in a polar aprotic solvent, such as N,N-DMF; the reaction may be carried out at 10-40° C., conveniently at ambient temperature. In a further example, the compound of formula (II) may be reacted with a compound of formula (III),
where
G is halogen;
X is —$CH_2$—;
W is of formula ($W_a$),
where
one A is N; and
the other two are C; and
$R^5$ and n are as hereinbefore defined, in the form of a salt, such as a hydrohalide, in the presence of an inorganic base, such as NaH or an organic base, such as BEMP, e.g., in a polar aprotic solvent, such as N,N-DMF; the reaction may be carried out at 10-40° C., conveniently at ambient temperature. In yet another example, the compound of formula (II) may be reacted with a compound of formula (III),
where
G is arylsulfonate;
X is —$CH_2$—; and
$R^5$, W and n are as hereinbefore defined, in the presence of an organic base, such as BEMP, e.g., in a mixture of a polar aprotic solvent, such as N,N-DMF and an ethereal solvent; the reaction may be carried out at 10-40° C., conveniently at ambient temperature. In a yet further example, the compound of formula (II) may be reacted with a compound of formula (III), where
G is halogen; X is a bond;
W is phenylene or naphthylene; and
$R^5$ and n are as hereinbefore defined, in the presence of a metal compound catalyst, e.g., a transition metal complex formed in situ from a metal salt, such as CuI and a diamine, and an inorganic base, such as sodium phosphate; the reaction is preferably carried out in an organic solvent, e.g., a polar aprotic solvent, such as dioxane; the reaction temperature may be from 140-180° C., preferably from 150-170° C.

Process variant (C) may be carried out using known procedures for α-alkylation of carboxylic esters, or analogously, e.g., as hereinafter described in the Examples. The reaction is conveniently carried out in the presence of an inorganic base, e.g., lithium diisopropyl amide, followed by addition of an alkyl iodide, e.g., methyl iodide. The reaction temperature may be from about −90° C. to about −60° C., but conveniently at −78° C.

Compounds of formula (II) are known or may be obtained by known methods, e.g., as described in U.S. Pat. No. 3,320,268, or analogously as hereinafter described in the Examples. Compounds of formula (III) are known or may be obtained by known methods, or analogously, as hereinafter described in the Examples.

The compounds of formula (I) in free form may be converted into salt form, and vice versa, in a conventional manner. The compounds in free or salt form can be obtained in the form of hydrates or solvates containing a solvent used for crystallisation. Compounds of formulae (I) and (II) can be recovered from reaction mixtures and purified in a conventional manner. Isomers, such as enantiomers, may be obtained in a conventional manner, e.g., by fractional crystallisation, chiral HPLC resolution or asymmetric synthesis from correspondingly asymmetrically substituted, e.g., optically active, starting materials.

Pharmaceutical Use and Assay

Compounds of formulae (I) and (II) and their pharmaceutically acceptable salts, hereinafter referred to alternatively as "agents of the invention", are useful as pharmaceuticals. In particular, the compounds have good CRTh2 receptor antagonist activity and may be tested in the following assays.

Filtration Binding Assay Protocol

The binding of CRTh2 antagonists is determined using membranes prepared from human CRTh2-expressing Chinese Hamster Ovary cells (CHO.K1-CRTh2). To produce cell membranes CHO.K1-CRTh2 cells cultured in roller bottles are harvested using cell dissociation buffer (Invitrogen). The cells are pelleted by centrifugation (167 g, 5 min). The cell pellet is incubated in hypotonic buffer (15 mM Tris-OH, 2 mM $MgCl_2$, 0.3 mM EDTA, 1 mM EGTA, 1× Complete™ tablet) at 4° C. for 30 min. At 4° C. cells are homogenized using a Polytron® (IKA Ultra Turrax T25) for 5 bursts of 1 second. The homogenate is centrifuged (Beckman Optima™ TL Ultracentrifuge, 48000 g, 30 min at 4° C.). The supernatant is discarded and the membrane pellet resuspended in homogenisation buffer (75 mM Tris-OH, 12.5 mM MgCl2, 0.3 mM EDTA, 1 mM EGTA, 250 mM Sucrose, 1× Complete™ tablet. Membrane preparations are aliquoted and stored at 80° C. The protein content is estimated using Bradford Protein Assay Dye (Bio Rad).

The binding of $[^3H]$-$PGD_2$ (157 Ci/mmol) to CHO.K1-CRTh2 membranes is determined in the absence (total binding) and presence (non-specific binding) of unlabelled $PGD_2$ (1 μM). Subtraction of the cpm (counts per minute) of $[^3H]$-$PGD_2$ binding in presence of excess unlabelled $PGD_2$ from that observed in the absence of excess unlabelled $PGD_2$ is defined as specific binding. Active CRTh2 antagonists are able to compete with $[^3H]$-$PGD_2$ for binding to the CRTh2 receptor and are identified in a decrease in the number of cpm bound.

The assay is performed in Greiner U-bottomed 96 well-plates, in a final volume of 100 μl per well. CHO.K1-CRTh2 membranes were diluted in assay buffer (10 mM HEPES-KOH (pH 7.4), 1 mM EDTA and 10 mM $MnCl_2$) and 10 μg are added to each well. $[^3H]$-$PGD_2$ is diluted in assay buffer and added to each well at a final concentration of 2.5 nM. To determine non-specific binding, $[^3H]$-$PGD_2$ binding to the CRTh2 receptor is competed with using unlabelled $PGD_2$ at a final well concentration of 1 μM. The experiment is done in triplicate, with reagents added to the wells as follows:

25 μL assay buffer for total binding or
25 μL $PGD_2$ to determine non-specific binding
25 μL $[^3H]PGD_2$
50 μL membranes
25 μL test compound in DMSO/assay buffer The plates are incubated at room temperature on a shaker for 1 hour, and then harvested (Tomtec Harvester 9600) onto GF/C filter plates using wash buffer (10 mM HEPES-KOH, pH 7.4). The plate is dried for 2 hours, prior to addition of Micro-Scint 20™ (50 μL) and sealing with TopSeal-S™. Plates are then counted using a Packard Top Count instrument, Plates are then read on the Packard Topcount with the 3H Scintillation program (1 min per well).

Ki (dissociation constant for the inhibition) values for the CRTh2 antagonists are reported.

Ki values are determined using Sigma Plot™ software, using the Cheng-Prussoff equation.

$$Ki = IC_{50}/1 + [S]/Kd$$

where S is the concentration of radioligand and Kd is the dissociation constant.

CRTH2 cAMP Functional Assay Protocol

This assay is conducted in CHO.K1-CRTh2 cells. cAMP is generated in the cell by stimulating cells with 5 μM forskolin, an adenylate cyclase activator. $PGD_2$ is added to activate the CRTh2 receptor which results in the attenuation of the forskolin-induced cAMP accumulation. Potential CRTh2 antagonists are tested for their ability to inhibit the $PGD_2$-mediated attenuation of the forskolin-induced cAMP accumulation in CHO.K1-CRTh2 cells.

For each concentration value on the dose-response curve, test compounds are prepared in assay stimulation buffer (HBSS, 5 mM HEPES, 10 μM IBMX±0.1% human serum albumin) containing DMSO (3% vol/vol) and 5 μL/well is added to an assay plate (384 well white optiplate).

CHO.K1-CRTh2 cultured in tissue culture flasks are washed with PBS and harvested with dissociation buffer. Cells are washed with PBS and resuspended in stimulation buffer to a concentration of $0.4×10^6$/mL and added to the assay plate (10 μL/well).

The assay plate is incubated at room temperature on a shaker for 15 minutes.

A mix of agonist (10 nM Prostaglandin $D_2$) and 5 μM forskolin is prepared in assay stimulation buffer and added to the assay plate (5 μL/well).

In addition, a cAMP standard is serially diluted in assay stimulation buffer and added to separate empty wells on the assay plate (20 μL/well). The cAMP standard allows for the quantification of cAMP generated in CHO.K1-CRTH2 cells.

The assay plate is incubated at room temperature on a shaker for 60 minutes.

Cell lysis buffer (Lysis buffer: Milli-Q $H_2O$, 5 mM HEPES, 0.3% Tween-20, 0.1% human serum albumin) is added to a bead mix (containing Alphascreen™ anti-cAMP acceptor beads 0.06 units/µL, Alphascreen™ streptavidin-coated donor beads 0.06 units/µL, biotinylated cAMP 0.06 units/mL, 10 µM IBMX) is prepared under darkened conditions 60 minutes prior to addition to the assay plate. The resulting lysis mix is added to all wells of the assay plate (40 µL/well).

The assay plate is sealed with Topseal-S™ and incubated in the dark at room temperature on a shaker for 45 minutes. The plate is then counted using a Packard Fusion™ instrument.

The resulting counts per minute are converted to nM cAMP by using the prepared cAMP standard curve. $IC_{50}$ values (concentration of CRTh2 antagonist required to inhibit 50% of the $PGD_2$-mediated attenuation of forskolin-induced cAMP accumulation in CHO.K1-CRTh2 cells) are then determined using Prism™ software.

Compounds of the Examples herein below generally have Ki values in the SPA binding assay below 1 µM. For example, the compounds of Examples 3, 18, 31, 54, 59, 84, 90, 92, 93, 94, 95, 96, 97, 99, 100, 102, 103, 105, 112, 115, 117, 119, 122, 125, 127, 129, 130, and 148 have Ki values of 0.048, 0.090, 0.122, 0.037, 0.033 0.10, 0.003, 0.022, 0.008, 0.007, 0.004, 0.029, 0.011, 0.012, 0.005, 0.056, 0.035, 0.098, 0.031, 0.045, 0.025, 0.029, 0.147, 0.027, 0.043, 0.043, 0.050, and 0.064 µM respectively.

Compounds of the Examples herein below generally have $IC_{50}$ values in the functional assay below 1 µM. For example, the compounds of Examples 3, 18, 31, 54, 59 and 84 have $IC_{50}$ values of 0.276, 0.171, 0.178, 0.168, 0.150, 0.084, 0.014, 0.040, 0.022, 0.016, 0.019, 0.021, 0.013, 0.019, 0.009, 0.091, 0.041, 0.046, 0.026, 0.080, 0.021, 0.064, 0.144, 0.095, 0.031, 0.143, 0.060, and 0.131 µM respectively.

Compounds of formulae (I) and (II), in free or salt form, are antagonists of the G-protein-coupled chemoattractant receptor CRTh2, expressed on Th2 cells, eosinophils and basophils. $PGD_2$ is the natural ligand for CRTh2. Thus, antagonists which inhibit the binding of CRTh2 and $PGD_2$ are useful in the treatment of allergic and anti-inflammatory conditions. Treatment in accordance with the invention may be symptomatic or prophylactic.

Accordingly, agents of the invention are useful in the treatment of inflammatory or obstructive airways diseases, resulting, e.g., in reduction of tissue damage, airways inflammation, bronchial hyperreactivity, remodelling or disease progression. Inflammatory or obstructive airways diseases to which the present invention is applicable include asthma of whatever type or genesis including both intrinsic (non-allergic) asthma and extrinsic (allergic) asthma, mild asthma, moderate asthma, severe asthma, bronchitis asthma, exercise-induced asthma, occupational asthma and asthma induced following bacterial infection. Treatment of asthma is also to be understood as embracing treatment of subjects, e.g., of less than 4 or 5 years of age, exhibiting wheezing symptoms and diagnosed or diagnosable as "wheezy infants", an established patient category of major medical concern and now often identified as incipient or early-phase asthmatics. (For convenience this particular asthmatic condition is referred to as "wheezy-infant syndrome".)

Prophylactic efficacy in the treatment of asthma will be evidenced by reduced frequency or severity of symptomatic attack, e.g., of acute asthmatic or bronchoconstrictor attack, improvement in lung function or improved airways hyperreactivity. It may further be evidenced by reduced requirement for other, symptomatic therapy, i.e., therapy for or intended to restrict or abort symptomatic attack when it occurs, e.g., anti-inflammatory (e.g., corticosteroid) or bronchodilatory. Prophylactic benefit in asthma may, in particular, be apparent in subjects prone to "morning dipping". "Morning dipping" is a recognised asthmatic syndrome, common to a substantial percentage of asthmatics and characterised by asthma attack, e.g., between the hours of about 4-6 a.m., i.e., at a time normally substantially distant from any previously administered symptomatic asthma therapy.

Other inflammatory or obstructive airways diseases and conditions to which the present invention is applicable include acute lung injury (ALI), adult respiratory distress syndrome (ARDS), chronic obstructive pulmonary, airways or lung disease (COPD, COAD or COLD), including chronic bronchitis or dyspnea associated therewith, emphysema, as well as exacerbation of airways hyperreactivity consequent to other drug therapy, in particular, other inhaled drug therapy. The invention is also applicable to the treatment of bronchitis of whatever type or genesis including, e.g., acute, arachidic, catarrhal, croupus, chronic or phthinoid bronchitis. Further inflammatory or obstructive airways diseases to which the present invention is applicable include pneumoconiosis (an inflammatory, commonly occupational, disease of the lungs, frequently accompanied by airways obstruction, whether chronic or acute, and occasioned by repeated inhalation of dusts) of whatever type or genesis including, e.g., aluminosis, anthracosis, asbestosis, chalicosis, ptilosis, siderosis, silicosis, tabacosis and byssinosis.

Having regard to their anti-inflammatory activity, in particular, in relation to inhibition of eosinophil activation, agents of the invention are also useful in the treatment of eosinophil related disorders, e.g., eosinophilia, in particular, eosinophils-related disorders of the airways, e.g., involving morbid eosinophilic infiltration of pulmonary tissues including hypereosinophilia as it effects the airways and/or lungs, as well as, e.g., eosinophil-related disorders of the airways consequential or concomitant to Löffler's syndrome; eosinophilic pneumonia; parasitic, in particular, metazoan, infestation including tropical eosinophilia; bronchopulmonary aspergillosis; polyarteritis nodosa including Churg-Strauss syndrome; eosinophilic granuloma; and eosinophil-related disorders affecting the airways occasioned by drug-reaction.

Agents of the invention are also useful in the treatment of inflammatory or allergic conditions of the skin, e.g., psoriasis, contact dermatitis, atopic dermatitis, alopecia areata, erythema multiforma, dermatitis herpetiformis, scleroderma, vitiligo, hypersensitivity angiitis, urticaria, bullous pemphigoid, lupus erythematosus, pemphisus, epidermolysis bullosa acquisita and other inflammatory or allergic conditions of the skin.

Agents of the invention may also be used for the treatment of other diseases or conditions, in particular, diseases or conditions having an inflammatory component, e.g., treatment of diseases and conditions of the eye, such as conjunctivitis, keratoconjunctivitis sicca and vernal conjunctivitis; diseases affecting the nose including allergic rhinitis; and inflammatory disease, in which autoimmune reactions are implicated or having an autoimmune component or aetiology, including autoimmune hematological disorders, e.g., hemolytic anemia, aplastic anaemia, pure red cell anaemia and idiopathic thrombocytopenia; systemic lupus erythematosus; polychondritis; sclerodoma; Wegener granulamatosis; dermatomyositis; chronic active hepatitis; myasthenia gravis; Steven-Johnson syndrome; idiopathic sprue; autoimmune inflammatory bowel disease, e.g., ulcerative colitis and Crohn's disease; endocrine ophthalmopathy; Grave's disease; sarcoidosis; alveolitis; chronic hypersensitivity pneumonitis; multiple sclerosis; primary billiary cirrhosis; uveitis (anterior and posterior); keratoconjunctivitis sicca and vernal keratoconjunctivitis; interstitial lung fibrosis; psoriatic arthritis; and glomerulonephritis, with and without nephrotic syndrome, e.g., including idiopathic nephrotic syndrome or minal change nephropathy.

Other diseases or conditions which may be treated with agents of the invention include septic shock; rheumatoid arthritis; osteoarthritis; proliferative diseases, such as cancer; atherosclerosis; allograft rejection following transplantation; stroke; obesity; restenosis; diabetes, e.g., diabetes mellitus type I (juvenile diabetes) and diabetes mellitus type II; diarrhoeal diseases; ischemia/reperfusion injuries; retinopathy, such as diabetic retinopathy or hyperbaric oxygen-induced retinopathy; and conditions characterised by elevated intraocular pressure or secretion of ocular aqueous humor, such as glaucoma.

The effectiveness of an agent of the invention in inhibiting inflammatory conditions, e.g., in inflammatory airways diseases, may be demonstrated in an animal model, e.g., a mouse or rat model, of airways inflammation or other inflammatory conditions, e.g., as described by Szarka et al., *J Immunol Methods*, Vol. 202, pp. 49-57 (1997); Renzi et al., *Am Rev Respir Dis*, Vol. 148, pp. 932-939 (1993); Tsuyuki et al., *J Clin Invest*, Vol. 96, pp. 2924-2931 (1995); Cernadas et al., *Am J Respir Cell Mol Biol*, Vol. 20, pp. 1-8 (1999); and Williams and Galli, *J Exp Med*, Vol. 192, pp. 455-462 (2000).

The agents of the invention are also useful as co-therapeutic agents for use in combination with other drug substances, such as anti-inflammatory, bronchodilatory or antihistamine drug substances, particularly in the treatment of obstructive or inflammatory airways diseases, such as those mentioned hereinbefore, e.g., as potentiators of therapeutic activity of such drugs or as a means of reducing required dosaging or potential side effects of such drugs. An agent of the invention may be mixed with the other drug substance in a fixed pharmaceutical composition or it may be administered separately, before, simultaneously with or after the other drug substance. Accordingly the invention includes a combination of an agent of the invention as hereinbefore described with an anti-inflammatory, bronchodilatory, antihistamine or anti-tussive drug substance, said agent of the invention and said drug substance being in the same or different pharmaceutical composition.

Such anti-inflammatory drugs include steroids, in particular, glucocorticosteroids, such as budesonide, beclamethasone dipropionate, fluticasone propionate, ciclesonide or mometasone furoate; or steroids, described in WO 02/88167, WO 02/12266, WO 02/100879, WO 02/00679 (especially those of Examples 3, 11, 14, 17, 19, 26, 34, 37, 39, 51, 60, 67, 72, 73, 90, 99 and 101), WO 03/035668, WO 03/048181, WO 03/062259, WO 03/064445 and WO 03/072592; non-steroidal glucocorticoid receptor agonists, such as those described in WO 00/00531, WO 02/10143, WO 03/082280, WO 03/082787, WO 03/104195 and WO 04/005229; LTB4 antagonists, such as those described in U.S. Pat. No. 5,451,700; LTD4 antagonists, such as montelukast and zafirlukast; PDE4 inhibitors, such as cilomilast (Ariflo® GlaxoSmithKline), Roflumilast (Byk Gulden), V-11294A (Napp), BAY19-8004 (Bayer), SCH-351591 (Schering-Plough), Arofylline (Almirall Prodesfarma), PD189659 (Parke-Davis), AWD-12-281 (Asta Medica), CDC-801 (Celgene), SelCID™ CC-10004 (Celgene), KW-4490 (Kyowa Hakko Kogyo), WO 03/104204, WO 03/104205, WO 04/000814, WO 04/000839 and WO 04/005258 (Merck), as well as those described in WO 98/18796 and WO 03/39544; A2a agonists, such as those described in EP 1052264, EP 1241176, EP 409595A2, WO 94/17090, WO 96/02543, WO 96/02553, WO 98/28319, WO 99/24449, WO 99/24450, WO 99/24451, WO 99/38877, WO 99/41267, WO 99/67263, WO 99/67264, WO 99/67265, WO 99/67266, WO 00/23457, WO 00/77018, WO 00/78774, WO 01/23399, WO 01/27130, WO 01/27131, WO 01/60835, WO 01/94368, WO 02/00676, WO 02/22630, WO 02/96462 and WO 03/086408; A2b antagonists, such as those described in WO 02/42298; and beta (β)-2-adrenoceptor agonists, such as albuterol (salbutamol), metaproterenol, terbutaline, salmeterol, fenoterol, procaterol, and especially, formoterol and pharmaceutically acceptable salts thereof, and compounds (in free or salt or solvate form) of formula (I) of WO 00/75114, which document is incorporated herein by reference, preferably compounds of the Examples thereof, especially a compound of formula

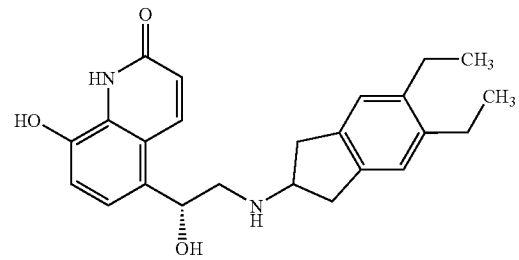

and pharmaceutically acceptable salts thereof, as well as compounds (in free or salt or solvate form) of formula (I) of WO 04/16601. Further β-2-adrenoreceptor agonists include compounds, such as those described in WO 99/64035, WO 01/42193, WO 01/83462, WO 02/066422, WO 02/070490, WO 02/076933, WO 2004/011416 and US 2002/0055651.

Such bronchodilatory drugs include anticholinergic or antimuscarinic agents, in particular, ipratropium bromide, oxitropium bromide, tiotropium salts and CHF 4226 (Chiesi), but also those described in WO 01/04118, WO 02/51841, WO 02/53564, WO 03/00840, WO 03/87094, WO 04/05285, WO 02/00652, WO 03/33495, WO 03/53966, EP 0424021, U.S. Pat. No. 5,171,744 and U.S. Pat. No. 3,714,357.

Such co-therapeutic antihistamine drug substances include cetirizine hydrochloride, acetaminophen, clemastine fumarate, promethazine, loratidine, desloratidine, diphenhydramine and fexofenadine hydrochloride.

Combinations of agents of the invention and steroids, β-2 agonists, PDE4 inhibitors or LTD4 antagonists may be used, e.g., in the treatment of COPD or, particularly, asthma. Combinations of agents of the invention and anticholinergic or antimuscarinic agents, PDE4 inhibitors, dopamine receptor agonists or LTB4 antagonists may be used, e.g., in the treatment of asthma or, particularly, COPD.

Other useful combinations of agents of the invention with anti-inflammatory drugs are those with antagonists of chemokine receptors, e.g., CCR-1, CCR-2, CCR-3, CCR-4, CCR-5, CCR-6, CCR-7, CCR-8, CCR-9, CCR-10, CXCR1, CXCR2, CXCR3, CXCR4 and CXCR5; particularly useful are CCR-3 antagonists, such as those described in WO 2002/026723, especially 4-{3-[(S)-4-(3,4-dichlorobenzyl)-morpholin-2-ylmethyl]-ureidomethyl}-benzamide and those described in WO 2003/077907, WO 2003/007939 and WO 2002/102775.

Also especially useful are CCR-5 antagonists, such as Schering-Plough antagonists SC-351125, SCH-55700 and SCH-D; Takeda antagonists, such as N-[[4-[[[6,7-dihydro-2-(4-methylphenyl)-5H-benzo-cyclohepten-8-yl]carbonyl]amino]phenyl]-methyl]tetrahydro-N,N-dimethyl-2H-pyran-4-aminium chloride (TAK-770); and CCR-5 antagonists, described in U.S. Pat. No. 6,166,037, WO 00/66558 and WO 00/66559.

The agents of the invention may be administered by any appropriate route, e.g., orally, e.g., in the form of a tablet or capsule; parenterally, e.g., intravenously; by inhalation, e.g., in the treatment of inflammatory or obstructive airways disease; intranasally, e.g., in the treatment of allergic rhinitis; topically to the skin, e.g., in the treatment of atopic dermatitis; or rectally, e.g., in the treatment of inflammatory bowel disease.

The present invention also provides a pharmaceutical composition comprising a compound of formula (I) in free form or in the form of a pharmaceutically acceptable salt, optionally together with a pharmaceutically acceptable diluent or carrier therefore. The composition may contain a co-therapeutic agent, such as an anti-inflammatory, bronchodilatory or antihistamine drug as hereinbefore described. Such compositions may be prepared using conventional diluents or excipients and techniques known in the galenic art. Thus oral dosage forms may include tablets and capsules. Formulations for topical administration may take the form of creams, ointments, gels or transdermal delivery systems, e.g., patches. Compositions for inhalation may comprise aerosol or other atomizable formulations or dry powder formulations.

When the composition comprises an aerosol formulation, it preferably contains, e.g., a hydro-fluoro-alkane (HFA) propellant, such as HFA134a or HFA227 or a mixture of these, and may contain one or more co-solvents known in the art, such as ethanol (up to 20% by weight); and/or one or more surfactants, such as oleic acid or sorbitan trioleate; and/or one or more bulking agents, such as lactose. When the composition comprises a dry powder formulation, it preferably contains, e.g., the compound of formula (I) having a particle diameter up to 10 microns, optionally together with a diluent or carrier, such as lactose, of the desired particle size distribution and a compound that helps to protect against product performance deterioration due to moisture. When the composition comprises a nebulised formulation, it preferably contains, e.g., the compound of formula (I) either dissolved, or suspended, in a vehicle containing water, a co-solvent, such as ethanol or propylene glycol and a stabilizer, which may be a surfactant.

The invention includes:
(a) an agent of the invention in inhalable form, e.g., in an aerosol or other atomizable composition or in inhalable particulate, e.g., micronised form;
(b) an inhalable medicament comprising an agent of the invention in inhalable form;
(c) a pharmaceutical product comprising such an agent of the invention in inhalable form in association with an inhalation device; and
(d) an inhalation device containing an agent of the invention in inhalable form.

Dosages of agents of the invention employed in practising the present invention will of course vary depending, e.g., on the particular condition to be treated, the effect desired and the mode of administration. In general, suitable daily dosages for oral administration are of the order of 0.01-100 mg/kg.

EXAMPLES

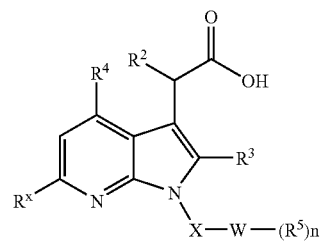

$R^2$=H except for Example 40, where $R^2=CH_3$.

$R^3=CH_3$ except for Example 81, where $R^3$=H and except for Example 87 and 153, where $R^3=CH_2CH_3$. $R^4$=H except for Example 62 and Example 89, where $R^4$=Cl.

$R^X$=H except for Example 99 and 100, where $R^6$=Cl

| Example | X—W—$(R^5)_n$ | MH⁺ |
|---------|---------------|-----|
| 1 | phenylsulfonyl | 331 |
| 2 | 4-chlorophenylsulfonyl | 365 |
| 3 | 4-nitrophenylsulfonyl | 376 |
| 4 | benzyl | 281 |
| 5 | 2-naphthylsulfonyl | 381 |
| 6 | 4-methylphenylsulfonyl | 345 |

-continued

| Example | X—W—(R⁵)ₙ | MH⁺ |
|---|---|---|
| 7 | 4-fluorophenylsulfonyl | 349 |
| 8 | 4-isopropylphenylsulfonyl | 373 |
| 9 | 3-bromophenylsulfonyl | 409 |
| 10 | 3-(trifluoromethyl)phenylsulfonyl | 399 |
| 11 | 4-(methylsulfonyl)phenylsulfonyl | 409 |
| 12 | 3-methoxyphenylsulfonyl | 361 |
| 13 | 4-biphenylsulfonyl | 407 |
| 14 | 3-fluorophenylsulfonyl | 349 |
| 15 | 2-fluorophenylsulfonyl | 349 |

-continued

| Example | X—W—(R⁵)ₙ | MH⁺ |
|---|---|---|
| 16 | 3,4-dichlorophenylsulfonyl | 399 |
| 17 | 4-methoxyphenylsulfonyl | 361 |
| 18 | 3,4-dichlorobenzyl | 349 |
| 19 | 2-methylbenzyl | 295 |
| 20 | (pyridin-3-yl)methyl | 282 |
| 21 | (pyridin-2-yl)methyl | 282 |
| 22 | (pyridin-4-yl)methyl | 282 |
| 23 | 4-chlorobenzyl | 315 |
| 24 | 3-cyanobenzyl | 306 |
| 25 | 3-chlorobenzyl | 315 |
| 26 | 4-cyanobenzyl | 306 |
| 27 | 3-methylbenzyl | 295 |

-continued

| Example | X—W—(R⁵)ₙ | MH⁺ |
|---|---|---|
| 28 | 3-(trifluoromethyl)benzyl | 349 |
| 29 | 4-fluorobenzyl | 299 |
| 30 | 2-chlorobenzyl | 315 |
| 31 | 4-(trifluoromethyl)benzyl | 349 |
| 32 | 3-fluorobenzyl | 299 |
| 33 | 4-(trifluoromethyl)phenylsulfonyl | 399 |
| 34 | 4-(difluoromethoxy)phenylsulfonyl | 397 |
| 35 | 3-chloro-2-methylphenylsulfonyl | 379 |
| 36 | 3-chloro-4-methylphenylsulfonyl | 379 |
| 37 | 2-chlorophenylsulfonyl | 365 |

-continued

| Example | X—W—(R⁵)ₙ | MH⁺ |
|---|---|---|
| 38 | 3-cyanophenylsulfonyl | 356 |
| 39 | 2,5-dichlorophenylsulfonyl | 399 |
| 40 | 3,4-dichlorophenylsulfonyl | 413 |
| 41 | 4-cyanophenylsulfonyl | [M − H]⁻ 354 |
| 42 | 2,4-dichlorophenylsulfonyl | 399 |
| 43 | 3-(trifluoromethoxy)phenylsulfonyl | [M − H]⁻ 413 |
| 44 | 2,5-difluorophenylsulfonyl | [M − H]⁻ 365 |
| 45 | 2-cyanophenylsulfonyl | [M − H]⁻ 354 |

-continued
| Example | X—W—(R⁵)ₙ | MH⁺ |
|---|---|---|
| 46 | 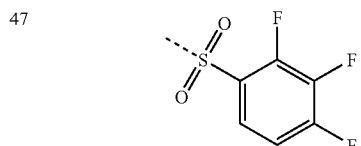 | 383 |
| 47 | 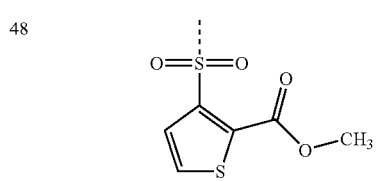 | [M − H]⁻ 383 |
| 48 | 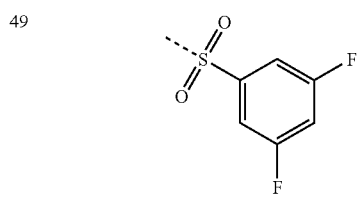 | 395 |
| 49 | 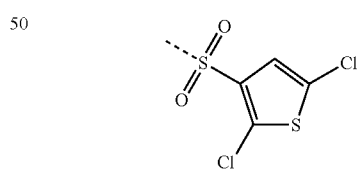 | 367 |
| 50 | 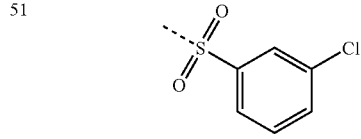 | 405 |
| 51 | 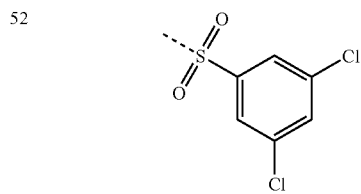 | 365 |
| 52 | 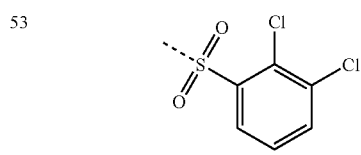 | 399 |
| 53 | 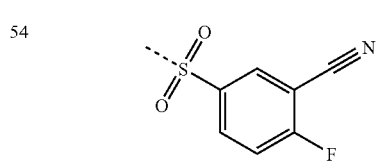 | 399 |
| 54 |  | 374 |
-continued
| Example | X—W—(R⁵)ₙ | MH⁺ |
|---|---|---|
| 55 | 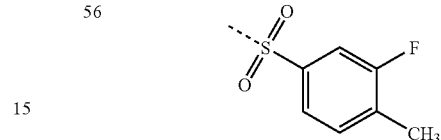 | 383 |
| 56 | 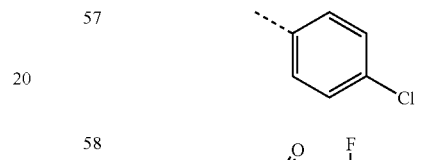 | 363 |
| 57 | 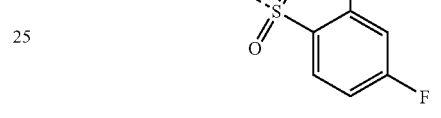 | 301 |
| 58 | 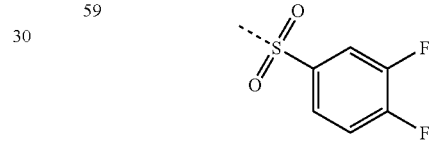 | 367 |
| 59 |  | 367 |
| 60 |  | 332 |
| 61 | 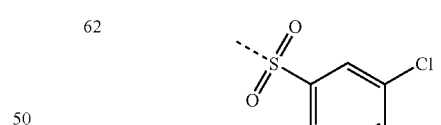 | 271 |
| 62 |  | 433 |
| 63 | 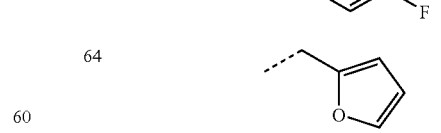 | 317 |
| 64 | 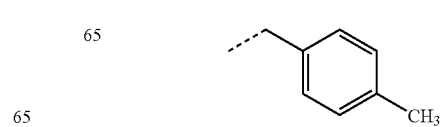 | 271 |
| 65 |  | 295 |

-continued
| Example | X—W—(R$^5$)$_n$ | MH$^+$ |
|---|---|---|
| 66 | 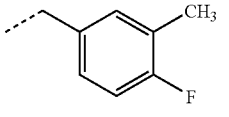 | 313 |
| 67 | 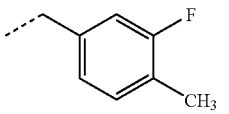 | 312 |
| 68 | 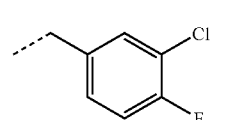 | 333 |
| 69 | 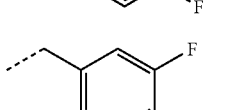 | 367 |
| 70 | 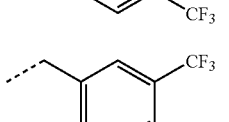 | 383 |
| 71 | 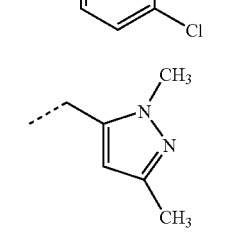 | 299 |
| 72 | 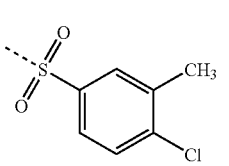 | 379/381 |
| 73 | 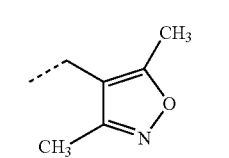 | 300 |
| 74 | 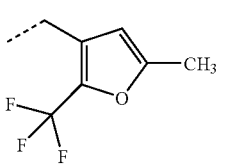 | 353 |
| 75 | 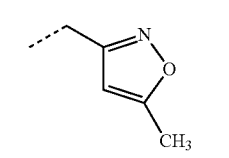 | 286 |
| 76 | 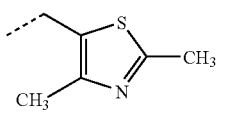 | 316 |
-continued
| Example | X—W—(R$^5$)$_n$ | MH$^+$ |
|---|---|---|
| 77 | 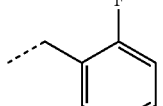 | 299 |
| 78 | 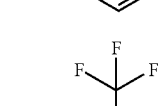 | 349 |
| 79 | 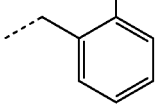 | 311 |
| 80 | 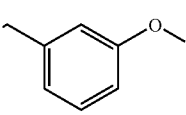 | 306 |
| 81 |  | 335 |
| 82 | 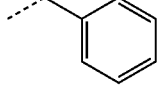 | 295 |
| 83 | 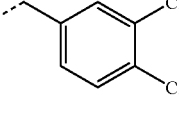 | 321 |
| 84 | 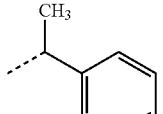 | 329 |
| 85 | 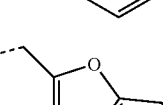 | 311 |
| 86 | 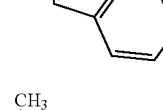 | 311 |

| Example | X—W—(R⁵)ₙ | MH⁺ |
|---|---|---|
| 87 | 4-(trifluoromethyl)benzyl | 363 |
| 88 | 4-(ethylsulfonyl)benzyl | 373 |
| 89 | 4-(methylsulfonyl)benzyl | 393 |
| 90 | 2-chloro-4-(methylsulfonyl)benzyl | 393 |
| 91 | 4-aminobenzyl | 296 |
| 92 | 4-(methylsulfonyl)-3-(trifluoromethyl)benzyl | 427 |
| 93 | 4-(ethylsulfonyl)-3-(trifluoromethyl)benzyl | 441 |
| 94 | 3-chloro-4-(ethylsulfonyl)benzyl | 407 |
| 95 | 3-(methylsulfonyl)-2-(trifluoromethyl)benzyl | 427 |

| Example | X—W—(R⁵)ₙ | MH⁺ |
|---|---|---|
| 96 | 4-(methylsulfonyl)benzyl | 359 |
| 97 | 1-[4-(methylsulfonyl)phenyl]ethyl, Enantiomer 1 | 373/373 |
| 98 | 4-(methylsulfinyl)benzyl | 343 |
| 99 | 4-(methylsulfonyl)benzyl | 393 |
| 100 | 4-(methylsulfonyl)-2-(trifluoromethyl)benzyl | 461 |
| 101 | 1-methyl-1H-benzotriazol-5-yl | 336 |
| 102 | 4-fluoro-3-methoxyphenylsulfonyl | 379 |
| 103 | 3-cyano-4-chlorophenylsulfonyl | 390 |
| 104 | 4-(trifluoromethylsulfonyl)benzyl | 413 |

-continued
| Example | X—W—(R⁵)ₙ | MH⁺ |
|---|---|---|
| 105 | 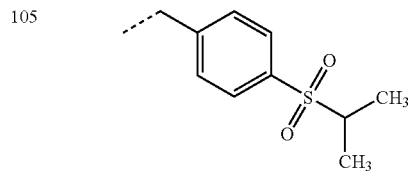 | 387 |
| 106 | 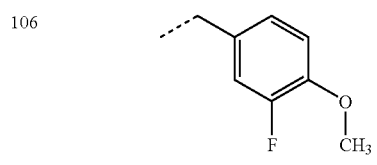 | 329 |
| 107 | 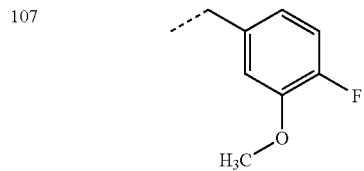 | 329 |
| 108 | 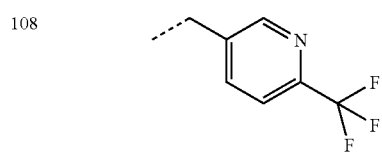 | 350 |
| 109 | 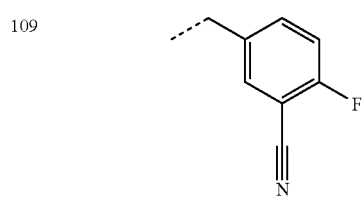 | 324 |
| 110 | 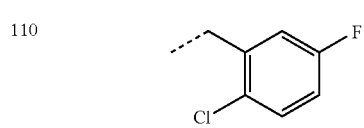 | 333 |
| 111 | 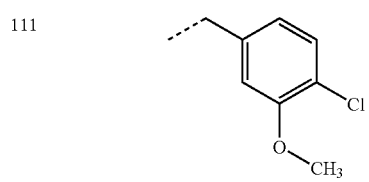 | 345 |
| 112 | 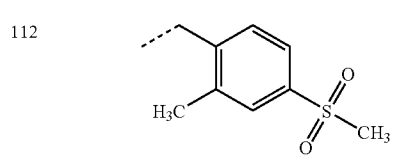 | 373 |
| 113 | 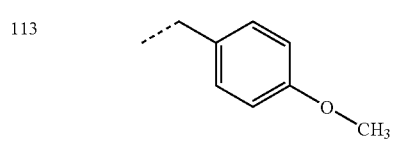 | 311 |
-continued
| Example | X—W—(R⁵)ₙ | MH⁺ |
|---|---|---|
| 114 |  | 311 |
| 115 | 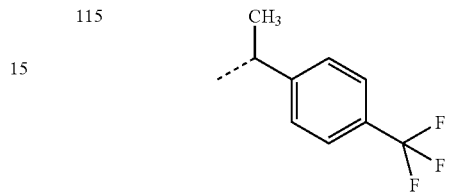 | 363 |
| 116 | 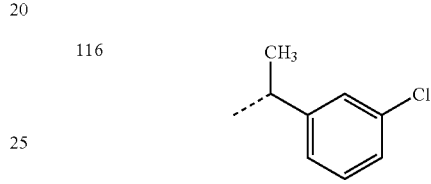 | 329 |
| 117 | 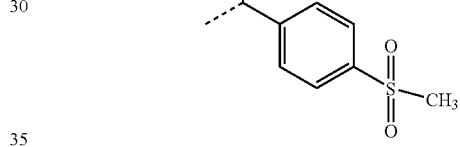 | 373 |
| 118 | 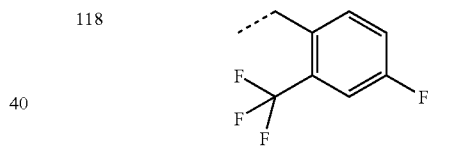 | 367 |
| 119 | 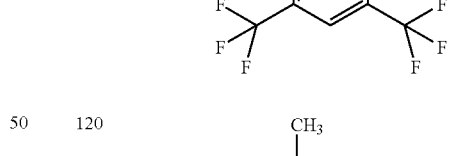 | 417 |
| 120 | 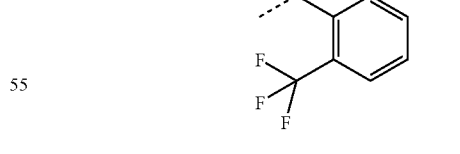 | 363 |
| 121 | 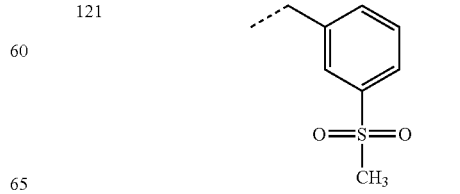 | 359 |

-continued
| Example | X—W—(R⁵)ₙ | MH⁺ |
|---|---|---|
| 122 | 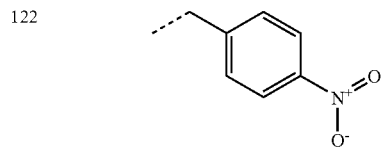 | 326 |
| 123 |  | 359 |
| 124 | 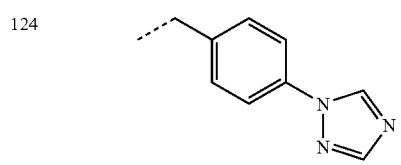 | 348 |
| 125 | 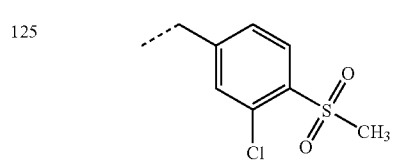 | 393 |
| 126 | 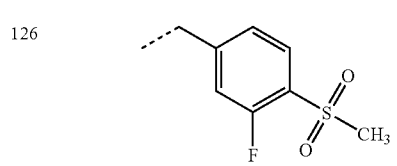 | 377 |
| 127 | 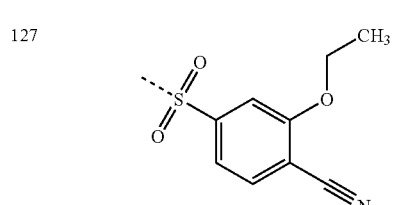 | 400 |
| 128 | 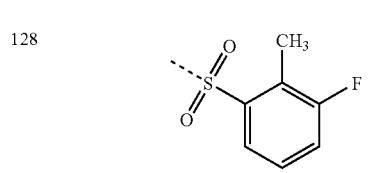 | 363 |
| 129 | 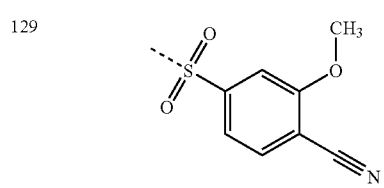 | 386 |
| 130 | 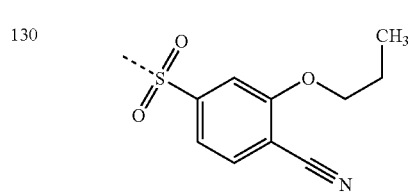 | 414 |
-continued
| Example | X—W—(R⁵)ₙ | MH⁺ |
|---|---|---|
| 131 | 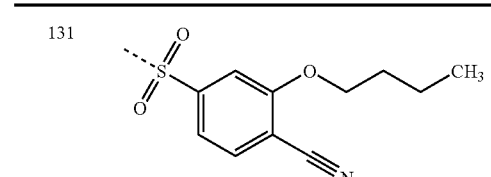 | 428 |
| 132 | 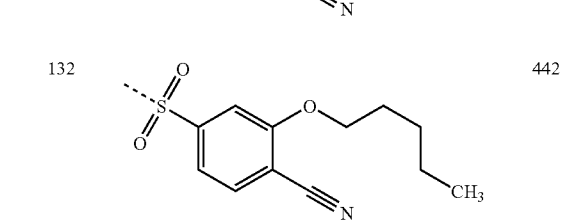 | 442 |
| 133 | 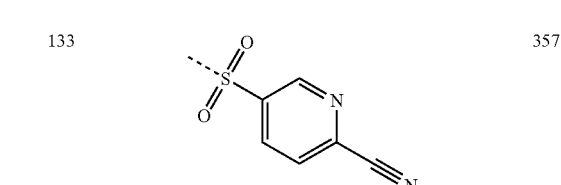 | 357 |
| 134 | 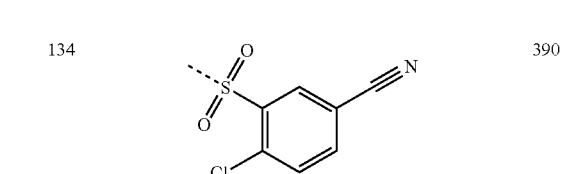 | 390 |
| 135 | 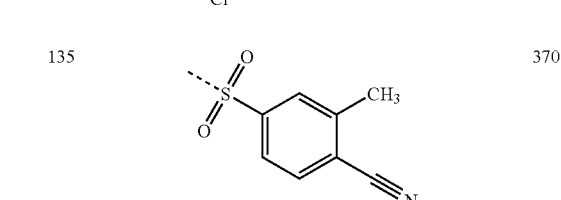 | 370 |
| 136 | 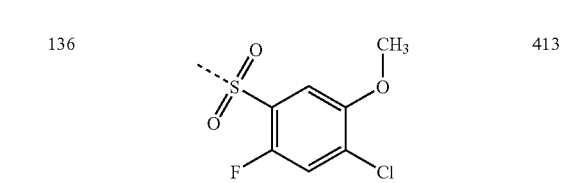 | 413 |
| 137 | 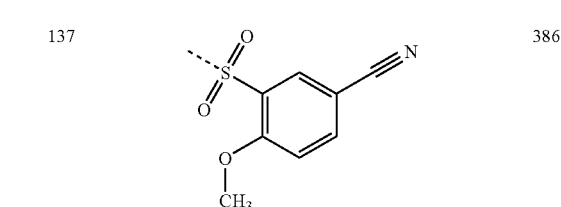 | 386 |
| 138 | 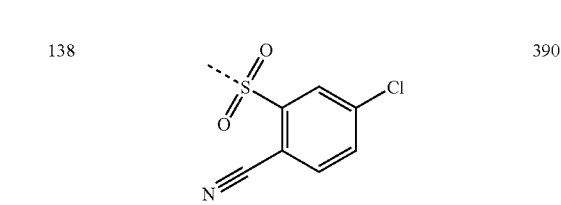 | 390 |

-continued

| Example | X—W—(R⁵)ₙ | MH⁺ |
|---------|-----------|-----|
| 139 | 3-chloro-4-sulfonyl-benzonitrile | 390 |
| 140 | 2-chloro-5-methoxy-sulfonylbenzene | 395 |
| 141 | 2-methoxy-5-chloro-sulfonylbenzene | 395 |
| 142 | 2-thiophenesulfonyl | 337 |
| 143 | 4-cyano-3-trifluoromethyl-sulfonylbenzene | 424 |
| 144 | 2-chloro-4-sulfonyl-benzonitrile | 390 |
| 145 | 3-fluoro-4-chloro-sulfonylbenzene | 383 |
| 146 | 3-chloro-4-trifluoromethyl-sulfonylbenzene | 433 |

-continued

| Example | X—W—(R⁵)ₙ | MH⁺ |
|---------|-----------|-----|
| 147 | 3-fluoro-4-trifluoromethyl-sulfonylbenzene | 417 |
| 148 | 3-methoxy-4-chloro-sulfonylbenzene | 395 |
| 149 | 3,4-dicyano-sulfonylbenzene | 381 |
| 150 | 3-trifluoromethyl-4-chloro-sulfonylbenzene | 433 |
| 151 | 3-cyano-4-morpholino-sulfonylbenzene | 441 |
| 152 | 3-fluoro-4-morpholino-sulfonylbenzene | 434 |
| 153 | 3-cyano-4-chloro-sulfonylbenzene | 404 |

Preparation of Specific Examples

General Experimental Conditions

NMR are recorded at 400 MHz in CDCl₃, unless otherwise noted. LCMS are recorded on an Agilent 1100 LC system with a Waters Xterra MS C18 4.6×100 5 μM column, eluting with 5-95% 10 mM aqueous ammonium bicarbonate in acetonitrile over 10 minutes, with negative ion electrospray ionization or 5-95% water+0.1% TFA in acetonitrile with positive ion electrospray ionization. MH⁺ and [M-H]⁻ refer to monoisotopic molecular weights.

The Emrys™ Optimiser microwave instrument (Personal-Chemistry AB) is used in the standard configuration as delivered.

Example 4

(1-Benzyl-2-methyl-1H-pyrrolo[2,3-b]pyridin-3-yl)-acetic acid

4a) BEMP (182 µL, 0.63 mmol) is added to a stirring solution of (2-methyl-1H-pyrrolo[2,3-b]pyridin-3-yl)-acetic acid methyl ester prepared as described in U.S. Pat. No. 3,320,268 (80 mg, 0.39 mmol) in DMF (2.4 mL). After 30 minutes, benzyl bromide (75 µL, 0.63 mmol) is added and the reaction stirred for 3 days, before partitioning between water and 1:1 EtOAc/ether. The organic layer is washed with brine then reduced in vacuo. The residue is purified by flash column chromatography (3:1 iso-hexane/EtOAc elution) to furnish (1-benzyl-2-methyl-1H-pyrrolo[2,3-b]pyridin-3-yl)-acetic acid methyl ester; MH⁺=295.

4b) 1M Aqueous NaOH (364 µL, 0.364 mmol) is added to a stirring solution of (1-benzyl-2-methyl-1H-pyrrolo[2,3-b]pyridin-3-yl)-acetic acid methyl ester (65 mg, 0.22 mmol) in 5:1 THF/MeOH (2.4 mL). After 5.5 hours, the reaction is evaporated, and partitioned between water and EtOAc. The aqueous layer is acidified to pH 3, and the resulting precipitate collected by filtration to furnish 1-benzyl-2-methyl-1H-pyrrolo[2,3-b]pyridin-3-yl)-acetic acid; MH⁺=281.

Examples 18, 19, 23-32, 63, 65-70, 77-80, 82 and 85-86

These examples, namely, [1-(3,4-Dichloro-benzyl)-2-methyl-1H-pyrrolo[2,3-b]pyridin-3-yl]-acetic acid; [2-Methyl-1-(2-methyl-benzyl)-1H-pyrrolo[2,3-b]pyridin-3-yl]-acetic acid; [1-(4-Chloro-benzyl)-2-methyl-1H-pyrrolo[2,3-b]pyridin-3-yl]-acetic acid; [1-(3-Cyano-benzyl)-2-methyl-1H-pyrrolo[2,3-b]pyridin-3-yl]-acetic acid; [1-(3-Chloro-benzyl)-2-methyl-1H-pyrrolo[2,3-b]pyridin-3-yl]-acetic acid; [1-(4-Cyano-benzyl)-2-methyl-1H-pyrrolo[2,3-b]pyridin-3-yl]-acetic acid; [2-Methyl-1-(3-methyl-benzyl)-1H-pyrrolo[2,3-b]pyridin-3-yl]-acetic acid; [2-Methyl-1-(3-trifluoromethyl-benzyl)-1H-pyrrolo[2,3-b]pyridin-3-yl]-acetic acid; [1-(4-Fluoro-benzyl)-2-methyl-1H-pyrrolo[2,3-b]pyridin-3-yl]-acetic acid; [1-(2-Chloro-benzyl)-2-methyl-1H-pyrrolo[2,3-b]pyridin-3-yl]-acetic acid; [2-Methyl-1-(4-trifluoromethyl-benzyl)-1H-pyrrolo[2,3-b]pyridin-3-yl]-acetic acid; [1-(3-Fluoro-benzyl)-2-methyl-1H-pyrrolo[2,3-b]pyridin-3-yl]-acetic acid; [1-(3,4-Difluoro-benzyl)-2-methyl-1H-pyrrolo[2,3-b]pyridin-3-yl]-acetic acid; [2-Methyl-1-(4-methyl-benzyl)-1H-pyrrolo[2,3-b]pyridin-3-yl]-acetic acid; [1-(4-Fluoro-3-methyl-benzyl)-2-methyl-1H-pyrrolo[2,3-b]pyridin-3-yl]-acetic acid; [1-(3-Fluoro-4-methyl-benzyl)-2-methyl-1H-pyrrolo[2,3-b]pyridin-3-yl]-acetic acid; [1-(3-Chloro-4-fluoro-benzyl)-2-methyl-1H-pyrrolo[2,3-b]pyridin-3-yl]-acetic acid; [1-(3-Fluoro-4-trifluoromethyl-benzyl)-2-methyl-1H-pyrrolo[2,3-b]pyridin-3-yl]-acetic acid; [1-(4-Chloro-3-trifluoromethyl-benzyl)-2-methyl-1H-pyrrolo[2,3-b]pyridin-3-yl]-acetic acid; [1-(2-Fluoro-benzyl)-2-methyl-1H-pyrrolo[2,3-b]pyridin-3-yl]-acetic acid; [2-Methyl-1-(2-trifluoromethyl-benzyl)-1H-pyrrolo[2,3-b]pyridin-3-yl]-acetic acid; [1-(3-Methoxy-benzyl)-2-methyl-1H-pyrrolo[2,3-b]pyridin-3-yl]-acetic acid; [1-(2-Cyano-benzyl)-2-methyl-1H-pyrrolo[2,3-b]pyridin-3-yl]-acetic acid; [2-Methyl-1-(1-phenyl-ethyl)-1H-pyrrolo[2,3-b]pyridin-3-yl]-acetic acid; [1-(4-Methoxy-benzyl)-2-methyl-1H-pyrrolo[2,3-b]pyridin-3-yl]-acetic acid; and [1-(2-Methoxy-benzyl)-2-methyl-1H-pyrrolo[2,3-b]pyridin-3-yl]-acetic acid, are prepared by the same process as that described for Example 4, using the appropriate benzyl halide.

Example 6

[2-Methyl-1-(toluene-4-sulfonyl)-1H-pyrrolo[2,3-b]pyridin-3-yl]-acetic acid

A solution of BEMP (90 µL, 0.31 mmol) in DMF (400 µL) is added to a solution of (2-methyl-1H-pyrrolo[2,3-b]pyridin-3-yl)-acetic acid methyl ester (40 mg, 0.20 mmol) in DMF (400 µL). After 40-50 minutes, a solution of 4-methyl-benzenesulfonyl chloride (60 mg, 0.31 mmol) in DMF (400 µL) is added. After a further 30 minutes, 1M aqueous NaOH (800 µL) is added, and the reaction is shaken mechanically for 105 minutes, then 1M aqueous HCl (800 µL) is added. The reaction is partitioned between water and CH₂Cl₂. The organic phase is loaded directly onto a pre-packed Isolute™ silica column and eluted with EtOAc to give crude product which is triturated with water to afford [2-methyl-1-(toluene-4-sulfonyl)-1H-pyrrolo[2,3-b]pyridin-3-yl]-acetic acid; MH⁺=345.

Examples 3, 5, 7-15, 17, 34, 35 and 37-39

These examples, namely, 2-Methyl-1-(4-nitro-benzenesulfonyl)-1H-pyrrolo[2,3-b]pyridin-3-yl]acetic acid; [2-Methyl-1-(naphthalene-2-sulfonyl)-1H-pyrrolo[2,3-b]pyridin-3-yl]acetic acid; [1-(4-Fluoro-benzenesulfonyl)-2-methyl-1H-pyrrolo[2,3-b]pyridin-3-yl]acetic acid; [1-(4-Isopropyl-benzenesulfonyl)-2-methyl-1H-pyrrolo[2,3-b]pyridin-3-yl]acetic acid; [1-(3-Bromo-benzenesulfonyl)-2-methyl-1H-pyrrolo[2,3-b]pyridin-3-yl]acetic acid, [2-Methyl-1-(3-trifluoromethyl-benzenesulfonyl)-1H-pyrrolo[2,3-b]pyridin-3-yl]acetic acid; [1-(4-Methane-sulfonyl-benzenesulfonyl)-2-methyl-1H-pyrrolo[2,3-b]pyridin-3-yl]acetic acid; [1-(3-Methoxy-benzenesulfonyl)-2-methyl-1H-pyrrolo[2,3-b]pyridin-3-yl]acetic acid; [1-(Biphenyl-4-sulfonyl)-2-methyl-1H-pyrrolo[2,3-b]pyridin-3-yl]acetic acid; [1-(3-Fluoro-benzenesulfonyl)-2-methyl-1H-pyrrolo[2,3-b]pyridin-3-yl]acetic acid; [1-(2-Fluoro-benzenesulfonyl)-2-methyl-1H-pyrrolo[2,3-b]pyridin-3-yl]acetic acid; [1-(4-Methoxy-benzenesulfonyl)-2-methyl-1H-pyrrolo[2,3-b]pyridin-3-yl]acetic acid; [1-(4-Difluoromethoxy-benzenesulfonyl)-2-methyl-1H-pyrrolo[2,3-b]pyridin-3-yl]-acetic acid; [1-(3-Chloro-2-methyl-benzenesulfonyl)-2-methyl-1H-pyrrolo[2,3-b]pyridin-3-yl]-acetic acid; [1-(2-Chloro-benzenesulfonyl)-2-methyl-1H-pyrrolo[2,3-b]pyridin-3-yl]-acetic acid; [1-(3-Cyano-benzenesulfonyl)-2-methyl-1H-pyrrolo[2,3-b]pyridin-3-yl]-acetic acid; and 1-(2,5-Dichloro-benzenesulfonyl)-2-methyl-1H-pyrrolo[2,3-b]pyridin-3-yl]-acetic acid, are prepared using the same process as that described for Example 6, using the appropriate benzenesulfonyl halide.

Example 16

[1-(3,4-Dichloro-benzenesulfonyl)-2-methyl-1H-pyrrolo[2,3-b]pyridin-3-yl]-acetic acid 16a) To an ice-cooled stirring suspension of NaH (60% dispersion in mineral oil; 63 mg, 1.6 mmol) in THF (3 mL) is added a solution of (2-methyl-1H-pyrrolo[2,3-b]pyridin-3-yl)-acetic acid methyl ester (200 mg, 1 mmol) in 3:1 THF/DMF (4 mL). After 45 minutes, a solution of 3,4-dichlorobenzenesulfonyl chloride (214 μL, 1.4 mmol) in THF (3 mL) is added. After 10 minutes, the reaction mixture is added to ice/water and extracted with EtOAc. The organic layer is washed with brine and evaporated. The crude product is purified by flash chromatography (3:1 iso-hexane/EtOAc elution), to afford [1-(3,4-dichloro-benzenesulfonyl)-2-methyl-1H-pyrrolo[2,3-b]pyridin-3-yl]-acetic acid methyl ester; $MH^+$=413.

16b) 1M Aqueous NaOH (1.5 mL) is added to a solution of [1-(3,4-dichloro-benzenesulfonyl)-2-methyl-1H-pyrrolo[2,3-b]pyridin-3-yl]-acetic acid methyl ester (218 mg, 0.53 mmol) in 1:1 THF/MeOH (6 mL). After 18 hours, the reaction is evaporated and the residue dissolved in water. The aqueous solution is acidified to pH 1, and the resulting precipitate is collected by filtration to afford [1-(3,4-dichloro-benzenesulfonyl)-2-methyl-1H-pyrrolo[2,3-b]pyridin-3-yl]-acetic acid; $MH^+$=399.

Examples 1 and 2

These examples, namely, (1-Benzenesulfonyl-2-methyl-1H-pyrrolo[2,3-b]pyridin-3-yl)acetic acid; and [1-(4-Chloro-benzenesulfonyl)-2-methyl-1H-pyrrolo[2,3-b]pyridin-3-yl]-acetic acid, are prepared by the same process as that described for Example 16, using the appropriate benzenesulfonyl halide.

Example 20

(2-Methyl-1-pyridin-3-ylmethyl-1H-pyrrolo[2,3-b]pyridin-3-yl)-acetic acid

20a) NaH (60% dispersion in mineral oil; 17 mg, 0.43 mmol) is added to a stirring, ice-cooled solution of 3-(bromomethyl)pyridine hydrobromide (109 mg, 0.43 mmol) in DMF (1.2 mL). After 20 minutes, a solution of (2-methyl-1H-pyrrolo[2,3-b]pyridin-3-yl)-acetic acid methyl ester (80 mg, 0.39 mmol) and BEMP (125 μL, 0.43 mmol) in 1.2 mL DMF is added dropwise. After 1 hour and 40 minutes, reaction is added to 25 mL water and extracted with EtOAc. The EtOAc layer is washed with water then brine, dried ($MgSO_4$) and evaporated.

The crude product is purified using flash chromatography (EtOAc elution) to give (2-methyl-1-pyridin-3-ylmethyl-1H-pyrrolo[2,3-b]pyridin-3-yl)-acetic acid methyl ester; $MH^+$=296.

20b) 1M Aqueous NaOH (0.5 mL) is added to a stirring solution of (2-methyl-1-pyridin-3-ylmethyl-1H-pyrrolo[2,3-b]pyridin-3-yl)-acetic acid methyl ester (35 mg, 0.12 mmol) in 1:1 THF/MeOH (2 mL). After 2 hours, the reaction is evaporated and the residue dissolved in water. The aqueous solution is acidified to pH 3-4, and the resulting precipitate collected by filtration to furnish (2-methyl-1-pyridin-3-ylmethyl-1H-pyrrolo[2,3-b]pyridin-3-yl)-acetic acid; $MH^+$=282.

Examples 21 and 22

These examples, namely, (2-Methyl-1-pyridin-2-ylmethyl-1H-pyrrolo[2,3-b]pyridin-3-yl)-acetic acid; and (2-Methyl-1-pyridin-4-ylmethyl-1H-pyrrolo[2,3-b]pyridin-3-yl)-acetic acid, are prepared by the same process as that described for Example 20, using the appropriate (bromomethyl)pyridine hydrobromide.

Example 36

1-(3-Chloro-4-methyl-benzenesulfonyl)-2-methyl-1H-pyrrolo[2,3-b]pyridin-3-yl]-acetic acid 36a) To a solution of (2-methyl-1H-pyrrolo[2,3-b]pyridin-3-yl)-acetic acid methyl ester (0.06 g, 0.294 mmol) in DMF (0.5 mL) is added a solution of BEMP (0.136 mL, 0.47 mmol) in DMF (0.5 mL). After 1 hour, a solution of 3-chloro-4-methyl-benzenesulfonyl chloride (0.105 g, 0.47 mmol) in DMF (0.5 mL) is added. The reaction mixture is stirred at room temperature overnight, then concentrated under reduced pressure to a minimum volume. The residue is loaded on a pre-packed Isolute™ silica column and eluted using a gradient eluent from 100% iso-hexane to 30% ethyl acetate in iso-hexane to afford [1-(3-chloro-4-methyl-benzenesulfonyl)-2-methyl-1H-pyrrolo[2,3-b]pyridin-3-yl]-acetic acid methyl ester; $MH^+$=393.

36b) 1M Aqueous NaOH (0.25 mL) is added to a stirring solution of [1-(3-chloro-4-methyl-benzenesulfonyl)-2-methyl-1H-pyrrolo[2,3-b]pyridin-3-yl]-acetic acid methyl ester (80 mg, 0.20 mmol) in 1:1 dioxane/water (2 mL). After 2.5 hours, the reaction mixture is acidified to pH 1 with 1M HCl which leads to the formation of a precipitate. The solid is isolated by filtration, washed with water and dried to afford [1-(3-chloro-4-methyl-benzenesulfonyl)-2-methyl-1H-pyrrolo[2,3-b]pyridin-3-yl]-acetic acid; $MH^+$=379.

Examples 33 and 46

These examples, namely, [2-Methyl-1-(4-trifluoromethyl-benzenesulfonyl)-1H-pyrrolo[2,3-b]pyridin-3-yl]-acetic acid; and 1-(2-Chloro-4-fluoro-benzenesulfonyl)-2-methyl-1H-pyrrolo[2,3-b]pyridin-3-yl]-acetic acid, are prepared by the same process as that described for Example 36, using the appropriate benzenesulfonyl halide.

Example 40

2-[1-(3,4-Dichloro-benzenesulfonyl)-2-methyl-1H-pyrrolo[2,3-b]pyridin-3-yl]-propionic acid 40a) To a stirring solution of diisopropylamine (34 μL, 0.24 mmol) in THF (1 mL), at −78° C., is added a 2.5M solution of n-BuLi in hexanes (105 μL, 0.26 mmol). After 20 minutes, a solution of [1-(3,4-dichloro-benzenesulfonyl)-2-methyl-1H-pyrrolo[2,3-b]pyridin-3-yl]-acetic acid methyl ester (Method B; 100 mg, 0.24 mmol) and MeI (15.2 μL, 0.24 mmol) in THF (1 mL) is added. The reaction is continued for 30 minutes, then allowed to warm to room temperature. The reaction mixture is evaporated to dryness and purified by flash chromatography (4:1 iso-hexane/EtOAc elution), to afford 2-[1-(3,4-dichloro-benzenesulfonyl)-2-methyl-1H-pyrrolo[2,3-b]pyridin-3-yl]-propionic acid methyl ester; $MH^+$=427.

40b) 1M Aqueous NaOH (0.25 mL) is added to a stirring solution of 2-[1-(3,4-dichloro-benzenesulfonyl)-2-methyl-1H-pyrrolo[2,3-b]pyridin-3-yl]-propionic acid methyl ester (17 mg, 0.04 mmol) in 1:1 THF/MeOH (1 mL). After 4 hours, the reaction is evaporated and the residue dissolved in water. The aqueous solution is acidified to pH 1, and resulting solid is collected by filtration. The crude product is purified by flash chromatography (10:1 EtOAc/MeOH), followed by trituration with iso-hexane, to afford 2-[1-(3,4-dichloro-benzenesulfonyl)-2-methyl-1H-pyrrolo[2,3-b]pyridin-3-yl]-propionic acid; $MH^+$=413.

Example 54

[1-(3-Cyano-4-fluoro-benzenesulfonyl)-2-methyl-1H-pyrrolo[2,3-b]pyridin-3-yl]-acetic acid 54a) To a solution of (2-methyl-1H-pyrrolo[2,3-b]pyridin-3-yl)-acetic acid methyl ester (0.5 g, 2.45 mmol) in DMF (3 mL) is added BEMP (1.13 mL, 3.92 mmol). After 1 hour, a solution of 3-cyano-4-fluoro-benzenesulfonyl chloride (0.86 g, 3.92 mmol) in DMF (3 mL) is added. The reaction mixture is stirred at room temperature overnight, then concentrated under reduced pressure to a minimum volume. The residue is loaded onto a pre-packed Isolute™ silica column and eluted using a gradient eluent from 100% iso-hexane to 50% EtOAc in iso-hexane to afford [1-(3-cyano-4-fluoro-benzenesulfonyl)-2-methyl-1H-pyrrolo[2,3-b]pyridin-3-yl]-acetic acid methyl ester; $MH^+=388$.

54b) 1M $BBr_3$ in $CH_2Cl_2$ (7.66 mL, 7.66 mmol) is added to a solution of [1-(3-cyano-4-fluoro-benzenesulfonyl)-2-methyl-1H-pyrrolo[2,3-b]pyridin-3-yl]-acetic acid methyl ester (0.495 g, 1.27 mmol) in $CH_2Cl_2$ (2 mL). The reaction mixture is exposed to microwave irradiation at 60° C. for 45 minutes. Water is added to the reaction mixture which is stirred for further 20 minutes. The organic layer is isolated using the Isolute™ phase separator cartridge and evaporated. The residue is loaded on a pre-packed Isolute™ silica column and eluted using a gradient eluent from 100% $CH_2Cl_2$ to 5% methanol in $CH_2Cl_2$ to afford the title compound; $MH^+=374$.

Examples 41-45, 47-53, 55, 56, 58 and 60

These examples, namely, [1-(4-Cyano-benzenesulfonyl)-2-methyl-1H-pyrrolo[2,3-b]pyridin-3-yl]-acetic acid; [1-(2,4-Dichloro-benzenesulfonyl)-2-methyl-1H-pyrrolo[2,3-b]pyridin-3-yl]-acetic acid; [2-Methyl-1-(3-trifluoromethoxy-benzenesulfonyl)-1H-pyrrolo[2,3-b]pyridin-3-yl]acetic acid; [1-(2,5-Difluoro-benzenesulfonyl)-2-methyl-1H-pyrrolo[2,3-b]pyridin-3-yl]-acetic acid; [1-(2-Cyano-benzenesulfonyl)-2-methyl-1H-pyrrolo[2,3-b]pyridin-3-yl]-acetic acid; [2-Methyl-1-(2,3,4-trifluoro-benzenesulfonyl)-1H-pyrrolo[2,3-b]pyridin-3-yl]-acetic acid; 3-(3-Carboxymethyl-2-methyl-pyrrolo[2,3-b]pyridine-1-sulfonyl)-thiophene-2-carboxylic acid methyl ester; [1-(3,5-Difluoro-benzenesulfonyl)-2-methyl-1H-pyrrolo[2,3-b]pyridin-3-yl]-acetic acid; [1-(2,5-Dichloro-thiophene-3-sulfonyl)-2-methyl-1H-pyrrolo[2,3-b]pyridin-3-yl]-acetic acid; [1-(3-Chloro-benzenesulfonyl)-2-methyl-1H-pyrrolo[2,3-b]pyridin-3-yl]-acetic acid; [1-(3,5-Dichloro-benzenesulfonyl)-2-methyl-1H-pyrrolo[2,3-b]pyridin-3-yl]-acetic acid; [1-(2,3-Dichloro-benzenesulfonyl)-2-methyl-1H-pyrrolo[2,3-b]pyridin-3-yl]-acetic acid; [1-(3-Chloro-4-fluoro-benzenesulfonyl)-2-methyl-1H-pyrrolo[2,3-b]pyridin-3-yl]-acetic acid; [1-(3-Fluoro-4-methyl-benzenesulfonyl)-2-methyl-1H-pyrrolo[2,3-b]pyridin-3-yl]-acetic acid; [1-(2,4-Difluoro-benzenesulfonyl)-2-methyl-1H-pyrrolo[2,3-b]pyridin-3-yl]-acetic acid; and [2-Methyl-1-(pyridine-3-sulfonyl)-1H-pyrrolo[2,3-b]pyridin-3-yl]-acetic acid, are made by the same process as that described for Example 54, using the appropriate benzenesulfonyl halide.

Example 57

1-(4-Chloro-phenyl)-2-methyl-1H-pyrrolo[2,3-b]pyridin-3-yl)-acetic acid

57a) A mixture of (2-methyl-1H-pyrrolo[2,3-b]pyridin-3-yl)-acetic acid methyl ester (100 mg, 0.49 mmol), 1-chloro-4-iodo-benzene (117 mg, 0.49 mmol), CuI (5 mg, 0.03 mmol), cyclohexane-1,2-diamine (6 µL, 0.05 mmol), potassium phosphate (218 mg, 1.0 mmol) and 1,4-dioxane (0.5 mL) is heated at 160° C. for 140 minutes. The reaction is cooled, diluted with EtOAc, filtered through silica and evaporated to dryness. The residue is purified by flash column chromatography (5:1 iso-hexane/EtOAc elution) to furnish [1-(4-chloro-phenyl)-2-methyl-1H-pyrrolo[2,3-b]pyridin-3-yl]-acetic acid methyl ester; $MH^+=315$.

57b) 1M Aqueous NaOH (0.5 mL) is added to a stirring solution of [1-(4-chloro-phenyl)-2-methyl-1H-pyrrolo[2,3-b]pyridin-3-yl]-acetic acid methyl ester (4 mg, 0.013 mmol) in 1:1 THF/MeOH (2 mL). After 18 hours, the reaction is evaporated and the residue dissolved in water. The aqueous solution is acidified to pH 1, and extracted with ethyl acetate. The organic layer is washed with water then brine, dried ($MgSO_4$) then evaporated, to give [1-(4-chloro-phenyl)-2-methyl-1H-pyrrolo[2,3-b]pyridin-3-yl]-acetic acid; $MH^+=301$.

Example 59

[1-(3,4-Difluoro-benzenesulfonyl)-2-methyl-1H-pyrrolo[2,3-b]pyridin-3-yl]-acetic acid 59a) To a solution of (2-methyl-1H-pyrrolo[2,3-b]pyridin-3-yl)-acetic acid methyl ester (0.8 g, 3.92 mmol) in DMF (3 mL) is added BEMP (1.81 mL, 6.27 mmol). After 1 hour, the reaction mixture is cooled to 0° C. and a solution of 3,4-difluoro-benzenesulfonyl chloride (0.83 mL, 6.27 mmol) in DMF (3 mL) is added. The reaction mixture is allowed to warm to room temperature, stirred at room temperature overnight, then concentrated under reduced pressure to a minimum volume. The residue is loaded on a pre-packed Isolute™ silica column and eluted using a gradient eluent from 100% iso-hexane to 30% EtOAc in iso-hexane to afford [1-(3,4-difluoro-benzenesulfonyl)-2-methyl-1H-pyrrolo[2,3-b]pyridin-3-yl]-acetic acid methyl ester; $MH^+=381$.

59b) 1M Aqueous LiOH (0.52 mL) is added at 0° C. to a stirring solution of [1-(3,4-difluoro-benzenesulfonyl)-2-methyl-1H-pyrrolo[2,3-b]pyridin-3-yl]-acetic acid methyl ester (200 mg, 0.526 mmol) in 1:1 dioxane/water (4 mL). The reaction mixture is stirred at 0° C. for 15 minutes, then allowed to warm to room temperature. After 2.5 hours, the reaction mixture is neutralised to pH 7 with 1M HCl and the solvent is removed under reduced pressure. The residue is loaded on a pre-packed Isolute™ silica column and eluted using a gradient eluent from 100% $CH_2Cl_2$ to 5% methanol in $CH_2Cl_2$ to afford [1-(3,4-difluoro-benzenesulfonyl)-2-methyl-1H-pyrrolo[2,3-b]pyridin-3-yl]-acetic acid; $MH^+=367$.

Example 72

[1-(4-Chloro-3-methyl-benzenesulfonyl)-2-methyl-1H-pyrrolo[2,3-b]pyridin-3-yl]-acetic acid This Example, is prepared by the same method as Example 59, using the appropriate benzenesulfonyl halide.

Example 61

(1-Furan-3-ylmethyl-2-methyl-1H-pyrrolo[2,3-b]pyridin-3-yl)-acetic acid

61a) BEMP (182 µL, 0.63 mmol) is added to a stirring solution of (2-methyl-1H-pyrrolo[2,3-b]pyridin-3-yl)-acetic acid methyl ester (80 mg, 0.39 mmol) in DMF (1.2 ml). After 30 minutes, a solution of toluene-4-sulfonic acid furan-3-ylmethyl ester in THF (1.4 ml, 0.45 mmol) is added. After 18 hours, the reaction is partitioned between water and ether. The organic layer is washed with brine then reduced in vacuo. The residue is purified by flash column chromatography (3:1 iso-hexane/EtOAc elution) to furnish (1-furan-3-ylmethyl-2-methyl-1H-pyrrolo[2,3-b]pyridin-3-yl)-acetic acid methyl ester; $MH^+$=285.

61b) 1M Aqueous NaOH (0.25 mL) is added to a stirring solution of (1-furan-3-ylmethyl-2-methyl-1H-pyrrolo[2,3-b]pyridin-3-yl)-acetic acid methyl ester (7.5 mg, 0.026 mmol) in 1:1 THF/MeOH (1 mL). After 18 hours, the reaction is evaporated and the residue dissolved in water. The aqueous solution is acidified to pH 3-4, and extracted with EtOAc. The organic layer is washed with water then brine, dried ($MgSO_4$), then evaporated to furnish (1-furan-3-ylmethyl-2-methyl-1H-pyrrolo[2,3-b]pyridin-3-yl)-acetic acid; $MH^+$=271.

Example 64

This example, namely, (1-furan-2-ylmethyl-2-methyl-1H-pyrrolo[2,3-b]pyridin-3-yl)-acetic acid is made by the same process as that described for Example 61, using the appropriate furan methyl ester.

Example 62

[4-Chloro-1-(3,4-dichloro-benzenesulfonyl)-2-methyl-1H-pyrrolo[2,3-b]pyridin-3-yl]-acetic acid 62a) m-Chloroperoxybenzoic acid (1.35 g, 7.8 mmol) is added to a solution of (2-methyl-1H-pyrrolo[2,3-b]pyridin-3-yl)-acetic acid methyl ester (1 g, 4.9 mmol) in 1,2-dimethoxyethane (15 mL) and is stirred at ambient temperature for 1.5 hours. The reaction mixture is poured into water and basified to pH 9-10 with aqueous saturated potassium carbonate. The precipitate is filtered off and the filtrate is extracted with $CH_2Cl_2$ then dried ($Na_2SO_4$) and evaporated to dryness in vacuo. The residue obtained is purified by column chromatography on silica gel using 10:1 $CH_2Cl_2$/MeOH as the eluent affording (2-methyl-7-oxy-1H-pyrrolo[2,3-b]pyridin-3-yl)-acetic acid methyl ester; $MH^+$=221.

62b) To (2-methyl-7-oxy-1H-pyrrolo[2,3-b]pyridin-3-yl)-acetic acid methyl ester (250 mg, 1.14 mmol) is added an excess of $POCl_3$ (20 mL) with cooling in an ice bath. The reaction mixture is heated at reflux for 5 hours. The $POCl_3$ is removed in vacuo. The residue is dissolved in $CH_2Cl_2$, washed with water, brine then dried ($Na_2SO_4$) and concentrated to dryness in vacuo. The crude product is purified by column chromatography on silica gel using 10:1 $CH_2Cl_2$/MeOH as the eluent, furnishing (4-chloro-2-methyl-1H-pyrrolo[2,3-b]pyridin-3-yl)-acetic acid methyl ester; $MH^+$=239.

62c) To a solution of (4-chloro-2-methyl-1H-pyrrolo[2,3-b]pyridin-3-yl)-acetic acid methyl ester (58 mg, 0.24 mmol) in DMF (1.2 mL) is added BEMP (113 μL, 0.39 mmol). The reaction mixture is stirred at ambient temperature for 40 minutes. 3,4-Dichloro-benzenesulfonyl chloride (60 μL, 0.39 mmol) is added and the reaction mixture is stirred for 10 minutes at ambient temperature. The reaction mixture is poured into ice cold water, extracted with EtOAc, washed with brine, dried ($Na_2SO_4$) and evaporated. The crude product is purified by column chromatography on silica gel using 1:8 EtOAc/iso-hexane as the eluent, furnishing [4-chloro-1-(3,4-dichloro-benzenesulfonyl)-2-methyl-1H-pyrrolo[2,3-b]pyridine-3-yl]-acetic acid methyl ester; $MH^+$=449.

62d) To a solution of [4-chloro-1-(3,4-dichloro-benzenesulfonyl)-2-methyl-1H-pyrrolo[2,3-b]pyridine-3-yl]-acetic acid methyl ester (40 mg, 0.09 mmol) in $CH_2Cl_2$ (1 mL), is added 1M $BBr_3$ in $CH_2Cl_2$ (536 μL, 0.54 mmol). The solution is subjected to microwave irradiation in a sealed reaction vessel with stirring at 60° C. over 45 minutes. The reaction mixture is evaporated to dryness in vacuo. Water is added and the suspension sonicated then filtered, washed with water and dried in vacuo, furnishing [4-chloro-1-(3,4-dichloro-benzenesulfonyl)-2-methyl-1H-pyrrolo[2,3-b]pyridine-3-yl]-acetic acid; $MH^+$=433.

Example 71

[1-(2,5-Dimethyl-2H-pyrazol-3-ylmethyl)-2-methyl-1H-pyrrolo[2,3-b]pyridin-3-yl]-acetic acid 71a) To a stirring solution of (2,5-dimethyl-2H-pyrazol-3-yl)-methanol (100 mg, 0.79 mmol) in diethyl ether (3 mL) is added $PBr_3$ (25 μL, 0.26 mmol). The reaction is stirred at room temperature for 18 hours, then water is added. The diethyl ether layer is separated and stored over solid NaOH and used in Step 71b without further characterization.

71b) BEMP (137 μL, 0.47 mmol) is added to a solution of (2-methyl-1H-pyrrolo[2,3-b]pyridin-3-yl)-acetic acid methyl ester (60 mg, 0.29 mmol) in DMF (0.8 mL). After 35 minutes, the diethyl ether layer from Step 71a (1.8 mL) is added. After 3 days, the reaction is partitioned between water and 1:1 EtOAc/ether. The organic layer is washed with brine then evaporated. The residue is purified by flash column chromatography (49:1 EtOAc/MeOH elution) to furnish [1-(2,5-dimethyl-2H-pyrazol-3-ylmethyl)-2-methyl-1H-pyrrolo[2,3-b]pyridin-3-yl]-acetic acid methyl ester; $MH^+$=313.

71c) 1M Aqueous NaOH (0.5 mL) is added to a stirring solution of [1-(2,5-dimethyl-2H-pyrazol-3-ylmethyl)-2-methyl-1H-pyrrolo[2,3-b]pyridin-3-yl]-acetic acid methyl ester (29 mg, 0.09 mmol) in 1:1 THF/MeOH (2 mL). After 18 hours, the reaction is evaporated and the residue dissolved in water. The aqueous solution is acidified to pH 1, and the resulting precipitate collected by filtration to furnish [1-(2,5-dimethyl-2H-pyrazol-3-ylmethyl)-2-methyl-1H-pyrrolo[2,3-b]pyridin-3-yl]-acetic acid; $MH^+$=299.

Examples 73-76 and 83-84

These examples, namely, [1-(3,5-Dimethyl-isoxazol-4-ylmethyl)-2-methyl-1H-pyrrolo[2,3-b]pyridin-3-yl]-acetic acid; [2-Methyl-1-(5-methyl-2-trifluoromethyl-furan-3-ylmethyl)-1H-pyrrolo[2,3-b]pyridin-3-yl]-acetic acid; [2-Methyl-1-(5-methyl-isoxazol-3-ylmethyl)-1H-pyrrolo[2,3-b]pyridin-3-yl]-acetic acid; [1-(2,4-Dimethyl-thiazol-5-ylmethyl)-2-methyl-1H-pyrrolo[2,3-b]pyridin-3-yl]-acetic acid; (1-Benzofuran-2-ylmethyl-2-methyl-1H-pyrrolo[2,3-b]pyridin-3-yl)-acetic acid; and {1-[1-(4-Chloro-phenyl)-ethyl]-2-methyl-1H-pyrrolo[2,3-b]pyridin-3-yl}-acetic acid, are made by the same process as that described for Example 71, using the appropriate heterocyclic methanol.

Example 81

[1-(3,4-Dichloro-benzyl)-1H-pyrrolo[2,3-b]pyridin-3-yl]-acetic acid 81a) 1H-Pyrrolo[2,3-b]pyridine (0.500 g, 4.2 mmol) is added to a stirred suspension of aluminium chloride (2.8 g, 21 mmol) in $CH_2Cl_2$ (100 mL) at 25° C. The suspension is stirred at 25° C. for 1 hour. Methyl oxalyl chloride (1.93 mL, 21 mmol) is added dropwise to the reaction mixture and the resulting suspension is stirred at 25° C. for 72 hours. The reaction mixture is cooled to 0° C. in an ice bath. MeOH (20 mL) is added dropwise then the reaction mixture is evaporated to dryness in vacuo. The crude material is triturated with 10:1 EtOAc/MeOH and filtered. The solid collected is further triturated with water and dried in vacuo to afford oxo-(1H-pyrrolo[2,3-b]pyridine-3-yl)-acetic acid methyl ester; $MH^+$=335.

81b) A mixture of oxo-(1H-pyrrolo[2,3-b]pyridine-3-yl)-acetic acid methyl ester (0.300 g, 1.47 mmol) is refluxed in hydrazine monohydrate (10 mL) for 1 hour to give a solution. KOH pellets (0.300 g, 5.35 mmol) are added and reflux is continued for 1 hour. The reaction mixture is evaporated to dryness in vacuo. To the residue is added dry MeOH (10 mL) and the solution is cooled in an ice bath. Concentrated $H_2SO_4$ (0.5 mL) is carefully added and the reaction mixture is refluxed at 80° C. for 1 hour. The reaction mixture is evaporated to dryness in vacuo, then partitioned between saturated $NaHCO_3$ aqueous and EtOAc. The EtOAc layer is separated and the aqueous phase is extracted with a further portion of EtOAc. The organics are combined, dried ($Na_2SO_4$) and evaporated in vacuo. The crude product is purified by flash chromatography with a pre-packed Isolute™ silica column, eluting with 1:8 EtOAc/iso-hexane-neat EtOAc gradient to afford (1H-pyrrolo[2,3-b]pyridine-3-yl)-acetic acid methyl ester; $MH^+$=191.

81c) To an ice cold solution of (1H-pyrrolo[2,3-b]pyridine-3-yl)-acetic acid methyl ester (50 mg, 0.26 mmol) in DMF (1 mL), is added BEMP (0.122 mL, 0.42 mmol). The reaction mixture is stirred at ambient temperature for 40 minutes, then 3,4-dichlorobenzyl bromide (0.101 g, 0.42 mmol) is added and the reaction mixture is stirred for 16 hours at ambient temperature. The reaction mixture is poured into ice cold water (40 mL) and extracted with EtOAc, washed with brine, dried ($Na_2SO_4$), filtered and evaporated in vacuo. The crude product is purified by column chromatography on silica gel using a pre-packed Isolute™ silica column (2 g) eluting with 1:20 EtOAc/iso-hexane, furnishing [1-(3,4-dichloro-benzyl)-1H-pyrrolo[2,3-b]pyridine-3-yl]-acetic acid methyl ester; $MH^+$=349.

81d) To a solution of [1-(3,4-dichloro-benzyl)-1H-pyrrolo[2,3-b]pyridine-3-yl]-acetic acid methyl ester (23 mg, 0.066 mmol) in MeOH (0.5 mL), is added 4N NaOH (0.25 mL). The reaction mixture is stirred at 25° C. for 5 minutes. The reaction mixture is evaporated in vacuo, to remove MeOH then cooled in an ice bath and acidified with concentrated HCl. The resultant solid is collected by filtration and triturated in $CHCl_3$ to afford [1-(3,4-dichloro-benzyl)-1H-pyrrolo[2,3-b]pyridine-3-yl]-acetic acid; $MH^+$=335.

Example 87

[2-Ethyl-1-(4-trifluoromethyl-benzyl)-1H-pyrrolo[2,3-b]pyridin-3-yl]-acetic acid 87a) 2-Ethyl-1H-pyrrolo[2,3-b]pyridine To a solution of 2-methyl-7-azaindole (1.32 g, 10 mmol) in dry diethyl ether (60 ml) at room temperature under an inert atmosphere is added n-BuLi (18.8 ml of a 1.6 M solution in hexanes, 30 mmol) followed by t-BuOK (2.24 g, 20 mmol). The reaction mixture is stirred at room temperature for 40 minutes and then cooled to −70° C. whereupon methyl iodide (1.25 ml, 20 mmol) is added dropwise. Stirring continues for a further 2 hours after which time, the reaction mixture is quenched with water (2 ml) and is allowed to slowly warm to room temperature. The cooled solution is poured onto water (200 ml), neutralized with 1N HCl and then extracted with diethyl ether (80 ml). The organic portion is washed with water (2×60 ml), dried ($Na_2SO_4$) and concentrated in vacuo to yield the titled compound as orange crystals. [$MH+CH_3CN$]+ =188)

87b) (2-Ethyl-1H-pyrrolo[2,3-b]pyridin-3-yl)-oxo-acetic acid methyl ester

A suspension of aluminium chloride (1.87 g, 14 mmol) in DCM (100 ml) under an inert atmosphere at room temperature is treated with 2-ethyl-1H-pyrrolo[2,3-b]pyridine (0.415 g, 14 mmol). After stirring at room temperature for 1 hour, methyl oxalyl chloride (1.29 ml, 14 mmol) is added dropwise to the reaction mixture and stirring continued overnight. The reaction mixture is cooled in an ice bath and methanol is added dropwise. The mixture is then poured onto ice-water (200 ml) and stirred. The organic portion is separated, dried ($Na_2SO_4$) and concentrated in vacuo. The resulting crude is triturated with ice cold water (20 ml) and sonicated. The solid is filtered and dried under vacuum at 50° C. to yield the titled compound. (MH+ 233)

87c) (2-Ethyl-1H-pyrrolo[2,3-b]pyridin-3-yl)-acetic acid methyl ester

To a solution of triethylsilane (818 µl, 5.12 mmol) in TFA (1.6 ml) at −10° C. is added portion wise (2-ethyl-1H-pyrrolo[2,3-b]pyridin-3-yl)-oxo-acetic acid methyl ester (0.34 g, 1.46 mmol). After stirring at room temperature overnight, the solvent is removed in vacuo and the resulting residue is neutralized with saturated sodium bicarbonate solution. The solution is extracted with DCM (3×20 ml) and the organic portions are combined, dried ($Na_2SO_4$) and concentrated in vacuo. The residue is loaded on a pre-packed Isolute™ silica column and eluted with DCM/MeOH (100:0 increasing to 98:2) to yield the titled compound as a yellow powder. (MH+ 219)

87d) [2-Ethyl-1-(4-trifluoromethyl-benzyl)-1H-pyrrolo[2,3-b]pyridin-3-yl]-acetic acid methyl ester To an ice-cooled stirring solution of (2-ethyl-1H-pyrrolo[2,3-b]pyridin-3-yl)-acetic acid methyl ester (80 mg, 0.37 mmol) in DMF (1 ml) is added BEMP (171 µl, 0.59 mmol). The solution is stirred at room temperature for 40 minutes and then re-cooled. 4-(Trifluoromethyl)benzyl bromide ((91 µl, 0.59 mmol) is added and stirring continues while the reaction mixture gradually warmed up to room temperature overnight. The resulting mixture is poured into water (30 ml) and extracted with 1:1 EtOAc/ether. The organic layer is washed with brine, dried ($Na_2SO_4$) and concentrated in vacuo. The residue is loaded on a pre-packed Isolute™ silica column and eluted with DCM to yield the titled compound as a pale yellow oil. (MH+ 377)

87e) [2-Ethyl-1-(4-trifluoromethyl-benzyl)-1H-pyrrolo[2,3-b]pyridin-3-yl]-acetic acid 0.5 M Aqueous NaOH (1.0 ml) is added to a solution of [2-ethyl-1-(4-trifluoromethyl-benzyl)-1H-pyrrolo[2,3-b]pyridin-3-yl]-acetic acid methyl ester (48 mg, 0.13 mmol) in 1:1 THF/MeOH (1 ml). After 3 hours the reaction is concentrated in vacuo, and the residue dissolved in water. The aqueous solution is cooled in an ice-bath and acidified to pH 2 using concentrated HCl. The resulting precipitate is filtered and dried under high vacuum at 50° C. to yield the titled compound as a white powder. (MH+ 363)

Example 88

[1-(4-Ethanesulfonyl-benzyl)-2-methyl-1H-pyrrolo[2,3-b]pyridin-3-yl]-acetic acid 88a) BEMP (182 µl, 0.64 mmol) is added to a stirring solution of (2-methyl-1H-pyrrolo[2,3-b]pyridin-3-yl)-acetic acid methyl ester (prepared as described in U.S. Pat. No. 3,320,268, 82 mg, 0.40 mmol) in DMF (2.6 ml). After 80 minutes, 1-bromomethyl-4-ethanesulfonyl-benzene (75 µl, 0.63 mmol) is added and the reaction stirred for 2 hours before partitioning between water and 1:1 EtOAc/diethyl ether. The organic layer is washed with brine then reduced in vacuo. The residue is purified by flash column chromatography (1:1 isohexane/EtOAc elution) to furnish [1-(4-ethanesulfonyl-benzyl)-2-methyl-1H-pyrrolo[2,3-b]pyridin-3-yl]-acetic acid methyl ester as a solid.

88b) 1M Aqueous NaOH (1 ml) is added to a stirring solution of [1-(4-ethanesulfonyl-benzyl)-2-methyl-1H-pyrrolo[2,3-b]pyridin-3-yl]-acetic acid methyl ester (89 mg, 0.23 mmol) in 1:1 THF/MeOH (4 ml). After 1 hour the reaction is evaporated and the resulting oil is dissolved in water (8 ml) and acidified to pH 3. The resulting precipitate is collected by filtration and dried in vacuo to afford [1-(4-ethanesulfonyl-benzyl)-2-methyl-1H-pyrrolo[2,3-b]pyridin-3-yl]-acetic acid (MH+ 373)

Example 89

[4-Chloro-1-(4-methanesulfonyl-benzyl)-2-methyl-1H-pyrrolo[2,3-b]pyridin-3-yl]-acetic acid 89a) (2-Methyl-7-oxy-1H-pyrrolo[2,3-b]pyridin-3-yl)-acetic acid methyl ester A stirred suspension of (2-methyl-1H-pyrrolo[2,3-b]pyridin-3-yl)-acetic acid methyl ester (5 g, 24.5 mmol) in 1,2-dimethoxyethane (100 ml) at room temperature under an inert atmosphere of Argon is treated portionwise with m-chloroperoxybenzoic acid (9.7 g, of a 77% w/w solid, 39.2 mmol). The reaction temperature is maintained at room temperature using an ice-bath due to the exothermic nature of the acid addition. The reaction mixture is stirred at room temperature for 3 hours and then poured onto water (400 ml) and basified to pH 9-10 using saturated potassium carbonate solution. The aqueous is extracted with DCM (2×100 ml) and the organic portions are combined, dried (Na$_2$SO$_4$) and concentrated in vacuo to yield (2-methyl-7-oxy-1H-pyrrolo[2,3-b]pyridin-3-yl)-acetic acid methyl ester. (MH+ 221)

89b) (4-Chloro-2-methyl-1H-pyrrolo[2,3-b]pyridin-3-yl)-acetic acid methyl ester

A suspension of (2-methyl-7-oxy-1H-pyrrolo[2,3-b]pyridin-3-yl)-acetic acid methyl ester (360 mg, 1.63 mmol) in phosphorus oxychloride (5 ml) is stirred and heated using microwave radiation in a Personal Chemistry Emrys™ Optimizer microwave reactor at 160° C. for 5 minutes. After standing at room temperature overnight, the reaction mixture is poured carefully onto ice water and extracted with DCM (3×40 ml). The organic portions are combined, washed with brine, dried (Na$_2$SO$_4$) and concentrated in vacuo. The resulting dark brown residue is loaded on a pre-packed Isolute™ silica column and eluted with DCM:methanol (10:1) to yield the titled compound as a cream solid. (MH+ 239)

89c) [4-Chloro-1-(4-methanesulfonyl-benzyl)-2-methyl-1H-pyrrolo[2,3-b]pyridin-3-yl]-acetic acid methyl ester To a cooled (0° C.) stirred solution of (4-chloro-2-methyl-1H-pyrrolo[2,3-b]pyridin-3-yl)-acetic acid methyl ester (0.1 g, 0.42 mmol) in dry DMF (2.5 ml) is added sodium hydride (0.019 g of a 60% dispersion in mineral oil, 0.47 mmol). After stirring at room temperature for 5 hours, the reaction mixture is re-cooled to 0° C. and treated with 4-methylsulfonylbenzyl bromide (0.105 g, 0.42 mmol). The resulting mixture is stirred and allowed to warm to room temperature overnight. The reaction mixture is diluted with water (3 ml) and extracted with ether (3×15 ml). The organic portions are combined, washed with water, dried (Na$_2$SO$_4$) and concentrated in vacuo. The resulting crude residue is loaded on a pre-packed Isolute™ silica column and eluted with iso-hexane:ethyl acetate (1:8) to yield the titled compound as a white powder. (MH+ 407).

89d) 1M Aqueous NaOH (0.5 ml) is added to a stirring solution of [4-chloro-1-(4-methanesulfonyl-benzyl)-2-methyl-1H-pyrrolo[2,3-b]pyridin-3-yl]-acetic acid methyl ester (38 mg, 0.093 mmol) in 1:1 THF/MeOH (1 ml). After stirring at room temperature for 4 hours, the reaction mixture is filtered to remove any undissolved material and is evaporated to dryness. The resulting oil is dissolved in water (1 ml) and acidified to pH 2. The resulting precipitate collected by filtration and dried in vacuo to afford [4-chloro-1-(4-methanesulfonyl-benzyl)-2-methyl-1H-pyrrolo[2,3-b]pyridin-3-yl]-acetic acid. (MH+ 393)

Example 90

[1-(2-Chloro-4-methanesulfonyl-benzyl)-2-methyl-1H-pyrrolo[2,3-b]pyridin-3-yl]-acetic acid 90a) 2-Chloro-4-methanesulfonyl-benzaldehyde A suspension of 2-chloro-4-fluorobenzaldehyde (24.9 g, 0.16 mol) and dry sodium methanesulfinate (17.9 g, 0.175 mmol) in dry DMSO (60 ml) is stirred at 90° C. overnight. The reaction mixture is allowed to cool to room temperature and then poured onto ice-water (400 ml). The resulting precipitated is collected by filtration and dried under high vacuum to yield the titled compound as a yellow powder.

90b) (2-Chloro-4-methanesulfonyl-phenyl)-methanol

To a stirred dispersion of 2-chloro-4-methanesulfonyl-benzaldehyde (25 g, 0.11 mol) in absolute ethanol (120 ml) is added sodium borohydride (4.6 g, 0.12 mol) whilst cooling with an ice-bath to maintain room temperature. After stirring at room temperature for 3 hours, the reaction mixture is poured carefully onto ice-water (600 ml) and acidified to pH 1-2 with 1N HCl. The resulting suspension is extracted with ethyl acetate (400 ml) and the organic portions are combined, washed with brine, dried (MgSO$_4$) and concentrated in vacuo. The resulting crude product is dried in a vacuum oven at 40° C. overnight to yield the titled product which is used crude in the next step.

90c) 1-Bromomethyl-2-chloro-4-methanesulfonyl-benzene

A cooled (0° C.), stirred suspension of (2-chloro-4-methanesulfonyl-phenyl)-methanol (19.1 g, 0.087 mol) in diethyl ether (250 ml) under an inert atmosphere, is treated with phosphorus tribromide (5.2 ml, 0.029 mol) and allowed to stir and warm to room temperature overnight. The resulting mixture is diluted with water (100 ml) and the organic portion is separated and dried over NaOH pellets for 5 minutes. The solvent is removed in vacuo and the resulting crude residue is loaded on a pre-packed Isolute™ silica column and eluted with iso-hexane/ethyl acetate (4:1) to yield the titled compound as a white powder.

90d) [1-(2-Chloro-4-methanesulfonyl-benzyl)-2-methyl-1H-pyrrolo[2,3-b]pyridin-3-yl]-acetic acid methyl ester To an ice cooled (0° C.) stirred solution of (2-methyl-1H-pyrrolo[2,3-b]pyridin-3-yl)-acetic acid methyl ester ((2.25 g, 1.1 mmol) in dry DMF (15 ml) is added sodium hydride (0.484 g of a 60% dispersion in mineral oil, 12.1 mmol). After stirring at room temperature for 3 hours, the reaction mixture is re-cooled to 0° C. and treated with 1-bromomethyl-2-chloro-4-methanesulfonyl-benzene (5.0 g, 17.6 mmol) and sodium iodide (2.64 g, 17.6 mmol). The resulting mixture is stirred and allowed to warm to room temperature overnight. The reaction mixture is poured onto water (300 ml) and extracted with 1:1 ethyl acetate/diethyl ether. The organic portions are washed with brine, dried ($Na_2SO_4$) and concentrated in vacuo and the resulting crude is purified by chromatography on silica eluting with ethyl acetate/iso-hexane (1:4 increasing to 1:2) to yield the titled product. (MH+ 407)

90e) [1-(2-Chloro-4-methanesulfonyl-benzyl)-2-methyl-1H-pyrrolo[2,3-b]pyridin-3-yl]-acetic acid 1M Aqueous NaOH (15 ml) is added to a stirring suspension of [1-(2-chloro-4-methanesulfonyl-benzyl)-2-methyl-1H-pyrrolo[2,3-b]pyridin-3-yl]-acetic acid methyl ester (2.6 g, 6.39 mmol) in 1:1 THF/MeOH (40 ml). After stirring at 45° C. for 1 hour, the reaction mixture is filtered to remove any undissolved material and is evaporated to dryness. The resulting solid is dissolved in water (30 ml) and acidified to pH 2-3 using concentrated HCl. The resulting suspension is collected by filtration and dried in vacuo at 50° C. to yield a solid which is purified by recrystallisation from IPA/water (1:3) to afford the titled product. (MH+ 393)

Example 91

[1-(4-Amino-benzyl)-2-methyl-1H-pyrrolo[2,3-b]pyridin-3-yl]-acetic acid

91a) [2-Methyl-1-(4-nitro-benzyl)-1H-pyrrolo[2,3-b]pyridin-3-yl]-acetic acid methyl ester To a stirred solution of (2-methyl-1H-pyrrolo[2,3-b]pyridin-3-yl)-acetic acid methyl ester (0.78 g, 3.8 mmol) in dry DMF (10 ml) is added dropwise, BEMP (1.21 ml, 4.2 mmol) over two minutes. After stirring at room temperature for 1 hour, the resulting solution is treated with 4-nitrobenzyl bromide (1.0 g, 4.6 mmol) in one portion and stirring continues overnight. The reaction is concentrated in vacuo with toluene and the resulting oil is purified by chromatography on silica eluting with iso-hexane/ethyl acetate (3:1) to yield [2-methyl-1-(4-nitro-benzyl)-1H-pyrrolo[2,3-b]pyridin-3-yl]-acetic acid methyl ester. (MH+ 340)

91b) [2-Methyl-1-(4-nitro-benzyl)-1H-pyrrolo[2,3-b]pyridin-3-yl]-acetic acid

1M Aqueous NaOH (1.18 ml) is added to a stirring suspension of [2-methyl-1-(4-nitro-benzyl)-1H-pyrrolo[2,3-b]pyridin-3-yl]-acetic acid methyl ester (0.2 g, 0.54 mmol) in 4:1 THF/MeOH (5 ml). The reaction mixture is allowed to stir at room temperature for 4 hours and then the solvent is removed in vacuo. The crude residue is dissolved in 1:1 THF/water and acidified to pH 3-4 using 6M HCl. After stirring for 30 minutes the resulting suspension is filtered and dried in vacuo at 110° C. to yield the titled product as a yellow solid. (MH+ 326)

91c) [1-(4-Amino-benzyl)-2-methyl-1H-pyrrolo[2,3-b]pyridin-3-yl]-acetic acid

[2-Methyl-1-(4-nitro-benzyl)-1H-pyrrolo[2,3-b]pyridin-3-yl]-acetic acid: is dissolved in 25:3 methanol/acetic acid under an inert atmosphere of Argon and then treated with palladium on carbon (10% w/w). The resulting suspension is stirred under an atmosphere of hydrogen for 4 hours and then filtered. The solvent is removed in vacuo to yield the titled product as a yellow solid. (MH+ 296)

Example 92

[1-(4-Methanesulfonyl-3-trifluoromethyl-benzyl)-2-methyl-1H-pyrrolo[2,3-b]pyridin-3-yl]-acetic acid 92a) 1-Bromomethyl-4-methanesulfonyl-3-trifluoromethyl-benzene The titled compound is prepared analogously to 1-bromomethyl-2-chloro-4-methanesulfonyl-benzene by replacing 2-chloro-4-fluorobenzaldehyde (step 90a) with 4-fluoro-3-trifluoromethylbenzaldehyde.

92b) 1-(4-Methanesulfonyl-3-trifluoromethyl-benzyl)-2-methyl-1H-pyrrolo[2,3-b]pyridin-3-yl]-acetic acid methyl ester To a stirred solution of (2-methyl-1H-pyrrolo[2,3-b]pyridin-3-yl)-acetic acid methyl ester ((12.8 g, 62.8 mmol) in dry DMF (200 ml) under an inert atmosphere of Argon is added dropwise, BEMP (19.9 ml, 69.1 mmol) over five minutes. After stirring at room temperature for 1 hour, the resulting solution is added dropwise to a stirred solution of 1-bromomethyl-4-methanesulfonyl-3-trifluoromethyl-benzene (23.9 g, 75.4 mmol) and stirred for 18 hours. The reaction is concentrated in vacuo with toluene and the resulting oil is purified by chromatography on silica eluting with iso-hexane/acetone (15:1). The crude is further purified by dissolving in hot ethyl acetate and refluxing in the presence of charcoal for 5 minutes. The solution is filtered and the solvent is removed in vacuo. The resulting solid is re-crystallized from ethyl acetate/iso-hexane to yield the titled product as a white solid. (MH+ 441)

92c) [1-(4-Methanesulfonyl-3-trifluoromethyl-benzyl)-2-methyl-1H-pyrrolo[2,3-b]pyridin-3-yl]-acetic acid 1-(4-Methanesulfonyl-3-trifluoromethyl-benzyl)-2-methyl-1H-pyrrolo[2,3-b]pyridin-3-yl]-acetic acid methyl ester (14.1 g, 32 mmol) in THF (150 ml) is treated dropwise with 1M NaOH (64 ml) at room temperature and after heating to 50° C., the suspension is treated with methanol (50 ml). The reaction mixture is stirred at 50° C. for 2 hours and then the solvent is removed in vacuo. The crude is triturated with ethyl acetate (200 ml) and the resulting solid is filtered and dissolved in water/dioxane (250 ml of a 2:1 mixture). The solution acidified to pH 3-4 using concentrated HCl and the resulting suspension is filtered, washed with water and then dried in vacuo. Further purification of the solid by recrystallisation from IPA/water (1:3) affords the titled product. (MH+ 427)

Example 93

[1-(4-Ethanesulfonyl-2-trifluoromethyl-benzyl)-2-methyl-1H-pyrrolo[2,3-b]pyridin-3-yl]-acetic acid 93a) 1-Bromomethyl-4-ethanesulfonyl-2-trifluoromethyl-benzene The titled compound is prepared analogously to 1-bromomethyl-2-chloro-4-methanesulfonyl-benzene by replacing 2-chloro-4-fluorobenzaldehyde (step 90a) with 4-fluoro-3-trifluoromethylbenzaldehyde and by replacing sodium methanesulfinate with sodium ethanesulfinate.

93b) [1-(4-Ethanesulfonyl-2-trifluoromethyl-benzyl)-2-methyl-1H-pyrrolo[2,3-b]pyridin-3-yl]-acetic acid methyl ester To a stirred solution of (2-methyl-1H-pyrrolo[2,3-b]pyridin-3-yl)-acetic acid methyl ester ((0.77 g, 3.78 mmol) in dry DMF (12 ml) under an inert atmosphere of Argon is added dropwise, BEMP (1.75 ml, 6.04 mmol). The mixture was allowed to stir at room temperature for 1 hour and then treated with 1-bromomethyl-4-ethanesulfonyl-2-trifluoromethyl-benzene (2 g, 6.04 mmol). Stirring continues for a further 2 hours after which time, the reaction mixture is partitioned between ethyl acetate/diethyl ether (80 ml of a 1:1 mixture) and water (100 ml). The organic portion is separated and washed with brine and concentrated in vacuo. Purification of the crude by chromatography on silica eluting with iso-hexane/ethyl acetate (3:1 increasing to 2:1) yields the titled product. (MH+ 455)

93c) [1-(4-Ethanesulfonyl-2-trifluoromethyl-benzyl)-2-methyl-1H-pyrrolo[2,3-b]pyridin-3-yl]-acetic acid To a stirred solution of [1-(4-ethanesulfonyl-2-trifluoromethyl-benzyl)-2-methyl-1H-pyrrolo[2,3-b]pyridin-3-yl]-acetic acid methyl ester (0.6 g, 1.32 mmol) in methanol/THF (8 ml of a 1:1 mixture) is added 1M NaOH (3 ml). After stirring at room temperature for 1.5 hours, the solvent is removed in vacuo and the residue is dissolved in water (3 ml). The solution is acidified to pH1 using 6M HCl and the resulting suspension is filtered and dried to yield the titled product. (MH+ 441)

Example 94

[1-(2-Chloro-4-ethanesulfonyl-benzyl)-2-methyl-1H-pyrrolo[2,3-b]pyridin-3-yl]-acetic acid 94a) 1-Bromomethyl-2-chloro-4-ethanesulfonyl-benzene The titled compound is prepared analogously to 1-bromomethyl-2-chloro-4-methanesulfonyl-benzene by replacing sodium methanesulfinate with sodium ethanesulfinate.

94b) [1-(2-Chloro-4-ethanesulfonyl-benzyl)-2-methyl-1H-pyrrolo[2,3-b]pyridin-3-yl]-acetic acid methyl ester To an ice cooled (0° C.) stirred solution of (2-methyl-1H-pyrrolo[2,3-b]pyridin-3-yl)-acetic acid methyl ester ((2.68 g, 13.1 mmol) in dry DMF (95 ml) is added sodium hydride (577 mg of a 60% dispersion in mineral oil, 14.41 mmol). After stirring at room temperature for 1.5 hours, the reaction mixture is re-cooled to 0° C. and treated with 1-bromomethyl-2-chloro-4-ethanesulfonyl-benzene (6.6 g, 22.2 mmol) and sodium iodide (3.3 g, 22.2 mmol). The resulting mixture is stirred and allowed to warm to room temperature overnight. The reaction mixture is poured onto water (600 ml) and extracted with 1:1 ethyl acetate/diethyl ether (4×300 ml). The organic portions are washed with brine, dried (MgSO$_4$) and concentrated in vacuo and the resulting crude is purified by chromatography on silica eluting with ethyl acetate/iso-hexane (1:8 increasing to 1:2) to yield the titled product. (MH+ 421)

94c) [1-(2-Chloro-4-ethanesulfonyl-benzyl)-2-methyl-1H-pyrrolo[2,3-b]pyridin-3-yl]-acetic acid To a stirred solution of [1-(2-chloro-4-ethanesulfonyl-benzyl)-2-methyl-1H-pyrrolo[2,3-b]pyridin-3-yl]-acetic acid methyl ester: (3.32 g, 7.89 mmol) in methanol/THF (30 ml of a 1:1 mixture) is added 1M NaOH (15 ml). After stirring at room temperature overnight, the solvent is removed in vacuo and the residue is dissolved in water (20 ml). The solution is acidified to pH1 using 6M HCl and the resulting suspension is filtered and recrystallised from IPA/water to yield the titled product. (MH+ 407)

Example 95

[1-(4-Methanesulfonyl-2-trifluoromethyl-benzyl)-2-methyl-1H-pyrrolo[2,3-b]pyridin-3-yl]-acetic acid 95a) 1-Bromomethyl-4-methanesulfonyl-2-trifluoromethyl-benzene The titled compound is prepared analogously to 1-bromomethyl-2-chloro-4-methanesulfonyl-benzene by replacing 2-chloro-4-fluorobenzaldehyde (step 90a) with 4-fluoro-2-trifluoromethylbenzaldehyde.

95b) [1-(4-Methanesulfonyl-2-trifluoromethyl-benzyl)-2-methyl-1H-pyrrolo[2,3-b]pyridin-3-yl]-acetic acid methyl ester To an ice-cooled solution of (2-methyl-1H-pyrrolo[2,3-b]pyridin-3-yl)-acetic acid methyl ester (12.8 g, 62.8 mmol) in dry DMF (400 ml) under an inert atmosphere of Argon is added dropwise, BEMP (18.1 ml, 62.8 mmol) over two minutes. After stirring at 10° C. for 40 minutes, the resulting solution is treated dropwise with 1-bromomethyl-4-methanesulfonyl-2-trifluoromethyl-benzene (23.8 g, 75.4 mmol) and allowed to warm to room temperature while stirring overnight. The reaction is concentrated in vacuo with toluene azeotroping and the resulting oil is partitioned between water (400 ml) and DCM (500 ml) and extracted with DCM (500 ml). The organic portions are combined and washed with water (2×200 ml). The resulting suspension is filtered and concentrated in vacuo with toluene azeotroping. The crude is purified by chromatography on silica eluting with iso-hexane/acetone (16:4) to yield the titled product. (MH+ 441)

95c) [1-(4-Methanesulfonyl-2-trifluoromethyl-benzyl)-2-methyl-1H-pyrrolo[2,3-b]pyridin-3-yl]-acetic acid To a mixture comprising [1-(4-methanesulfonyl-2-trifluoromethyl-benzyl)-2-methyl-1H-pyrrolo[2,3-b]pyridin-3-yl]-acetic acid methyl ester: (11.8 g, 26.8 mmol) in water (100 ml) and THF (250 ml) is added dropwise NaOH (53.6 ml of a 1M aqueous solution) at room temperature and the two phase suspension is allowed to stir overnight. The solvent is removed in vacuo and the crude is triturated with diethyl ether, DCM and ethyl acetate. The resulting solid is dissolved in hot water (150 ml) and adjusted to pH 3-4 using 6M HCl. The suspension that forms is filtered and is further purified by dissolving in hot IPA (250 ml) and refluxing in the presence of charcoal for 5 minutes. The solution is filtered and the titled product is recrystallised from water/IPA as a white/pale green crystals. (MH+ 427)

Example 96

1-(4-Methanesulfonyl-benzyl)-2-methyl-1H-pyrrolo[2,3-b]pyridin-3-yl]-acetic acid

96a) [1-(4-Methanesulfonyl-benzyl)-2-methyl-1H-pyrrolo[2,3-b]pyridin-3-yl]-acetic acid methyl ester A solution of (2-methyl-1H-pyrrolo[2,3-b]pyridin-3-yl)-acetic acid methyl ester ((6.8 g, 33.5 mmol) in dry DMF (150 ml) under an inert atmosphere of Argon is treated with BEMP (10.5 ml, 36.5 mmol) dropwise, over two minutes. The solution is stirred at room temperature for 1 hour and then a solution of 4-methylsulphonyl benzyl bromide (10.0 g, 40.2 mmol) in DMF (60 ml) is added dropwise over 5 minutes. After stirring at room temperature overnight, the solvent is removed in vacuo and azeotroped with toluene (200 ml). The resulting crude is purified by chromatography on silica eluting with ethyl acetate/iso-hexane (20-100% ethyl acetate) to yield the titled compound as a green oil. (MH+ 373)

96b) 1-(4-Methanesulfonyl-benzyl)-2-methyl-1H-pyrrolo[2,3-b]pyridin-3-yl]-acetic acid To a solution of [1-(4-methanesulfonyl-benzyl)-2-methyl-1H-pyrrolo[2,3-b]pyridin-3-yl]-acetic acid methyl ester (6.54 g, 17.6 mmol) in THF (100 ml) is added dropwise, 1M NaOH (35.2 ml). The turbid solution is heated to 40° C. and methanol (10 ml) is added to afford a clear solution. After stirring at room temperature for a 4 hours, the solvent is removed in vacuo and the crude is triturated with ethyl acetate. The resulting solid is filtered and dissolved in water/THF (200 ml of a 3:1 mixture) and then acidified to pH 3. The solvent is removed in vacuo and the resulting solid is recrystallised from ethanol/water to yield the titled product. (MH+ 359)

Example 97

{1-[1-(4-Methanesulfonyl-phenyl)-ethyl]-2-methyl-1H-pyrrolo[2,3-b]pyridin-3-yl}-acetic acid—Enantiomer 1 and 2

97a) {1-[1-(4-Methanesulfonyl-phenyl)-ethyl]-2-methyl-1H-pyrrolo[2,3-b]pyridin-3-yl}-acetic acid methyl ester A solution of (2-methyl-1H-pyrrolo[2,3-b]pyridin-3-yl)-acetic acid methyl ester ((2.37 g, 11.12 mmol) in dry DMF (38 ml) at room temperature is treated with BEMP (4.39 ml, 15.19 mmol) dropwise. The reaction mixture is stirred at room temperature for 35 minutes and then 1-(1-bromo-ethyl)-4-methanesulfonyl-benzene (4.00 g, 15.18 mmol) and sodium iodide (12.29 g, 15.28 mmol) is added. After stirring at 60° C. for 1 hour, the reaction mixture is allowed to cool to room temperature and then diluted with ethyl acetate/ether (200 ml of a 1:1 mixture) and water (150 ml). The organic portion is washed with brine, dried ($Na_2SO_4$) and concentrated in vacuo and the resulting crude is purified by chromatography on silica eluting with ethyl acetate/iso-hexane (2:3 increasing to 1:1 ethyl acetate) to yield the titled product as a racemic mixture. The enantiomers are resolved using a chiralcel OD column eluting with 30% IPA in hexanes to afford enantiomer A (retention time=14.33 minutes) and enantiomer B (retention time=17.68 minutes)

97b) {1-[1-(4-Methanesulfonyl-phenyl)-ethyl]-2-methyl-1H-pyrrolo[2,3-b]pyridin-3-yl}-acetic acid—Enantiomer 1

A solution of {1-[1-(4-methanesulfonyl-phenyl)-ethyl]-2-methyl-1H-pyrrolo[2,3-b]pyridin-3-yl}-acetic acid methyl ester (Enantiomer A) (22 mg, 0.05 mmol) in THF (0.5 ml) and methanol (0.5 ml) is treated with 2M lithium hydroxide (0.2 ml) and stirred at room temperature for 30 minutes. The solvent is removed in vacuo and the crude is dissolved in water (10 ml) and acidified to pH1 using concentrated HCl. The mixture is then extracted with ethyl acetate (2×10 ml) and the organic portions are washed with brine, dried ($MgSO_4$) and concentrated in vacuo to yield the titled product as a colourless glassy solid. (MH+ 373) The enantiomer of the titled compound (Enantiomer 2) is prepared analogously using the procedure described above by replacing Enantiomer A with Enantiomer B. (MH+ 373)

Example 98

[1-(4-Methanesulfinyl-benzyl)-2-methyl-1H-pyrrolo[2,3-b]pyridin-3-yl]-acetic acid

98a) [1-(4-Methanesulfinyl-benzyl)-2-methyl-1H-pyrrolo[2,3-b]pyridin-3-yl]-acetic acid methyl ester A solution of (2-methyl-1H-pyrrolo[2,3-b]pyridin-3-yl)-acetic acid methyl ester ((0.512 g, 2.51 mmol) in dry DMF (5.6 ml) at room temperature is treated with BEMP (1.17 ml, 4.01 mmol) dropwise. The reaction mixture is stirred at room temperature for 80 minutes and then treated with 1-bromomethyl-4-methanesulfinyl-benzene (0.934 g, 4.01 mmol). After stirring at room temperature for a further 2 hours, the reaction mixture is partitioned between ethyl acetate/ether (300 ml of a 1:1 mixture) and water (30 ml). The organic portion is separated and washed with brine, dried ($Na_2SO_4$) and concentrated in vacuo. The resulting crude is purified by chromatography on silica eluting with DCM/methanol (10:1) to yield the titled product. (MH+ 357)

98b) [1-(4-Methanesulfinyl-benzyl)-2-methyl-1H-pyrrolo[2,3-b]pyridin-3-yl]-acetic acid To a stirred solution of [1-(4-methanesulfinyl-benzyl)-2-methyl-1H-pyrrolo[2,3-b]pyridin-3-yl]-acetic acid methyl ester (0.340 g, 0.95 mmol) in THF/MeOH (8 ml of a 1:1 mixture) is added 1M NaOH (2 ml) and the reaction mixture is stirred for 2 hours. The solvent is removed in vacuo and the resulting oil is dissolved in water and acidified to pH2 using

Example 99

[6-Chloro-1-(4-methanesulfonyl-benzyl)-2-methyl-1H-pyrrolo[2,3-b]pyridin-3-yl]-acetic acid 99a) 2-Methyl-1H-pyrrolo[2,3-b]pyridine 7-oxide To a cooled (0° C.) solution of 2-methyl-7-azaindole (5 g, 37.8 mmol) in 1,2-dimethoxyethane (40 ml) is added m-chloroperoxybenzoic acid (10.4 g, of a 77% w/w solid, 46.6 mmol). The reaction mixture is stirred at 0° C. for 30 minutes, at room temperature for 3 hours and then poured into water (400 ml). The solution is basified to pH 9-10 using saturated potassium carbonate solution. The aqueous is extracted with DCM (2×100 ml) and the organic portions are combined, dried (MgSO$_4$) and concentrated in vacuo. Purification of the resulting crude by chromatography on silica eluting firstly with neat ethyl acetate followed by DCM/MeOH (10:1) yields the titled compound as a yellow powder. (MH+ 297 appears as a dimer)

99b) 6-Chloro-2-methyl-pyrrolo[2,3-b]pyridine-1-carboxylic acid methyl ester

To a solution of 2-methyl-1H-pyrrolo[2,3-b]pyridine 7-oxide: (0.89 g, 6 mmol) in THF (20 ml) under an inert atmosphere of Argon is added HMDS (1.25 ml, 6 mmol) at room temperature. The solution is cooled (0° C.) and treated with methyl chloroformate (1.16 ml, 15 mmol). The reaction mixture is stirred at room temperature overnight and the solvent is then removed in vacuo. The residue is dissolved in ethyl acetate (30 ml) and washed with saturated sodium hydrogencarbonate solution. The aqueous is back-extracted with ethyl acetate (2×20 ml) and the organic portions are combined, dried (MgSO$_4$) and concentrated in vacuo. Purification of the resulting crude by chromatography on silica eluting with ethyl acetate/iso-hexane (1:8) yields the titled product. (MH+ 225).

99c) 6-Chloro-2-methyl-1H-pyrrolo[2,3-b]pyridine

6-Chloro-2-methyl-pyrrolo[2,3-b]pyridine-1-carboxylic acid methyl ester (0.225 g, 1 mmol) is dissolved in methanol (30 ml) and 1M NaOH (10 ml) and stirred at room temperature overnight. The methanol is removed in vacuo and the resulting white suspension is extracted with chloroform (3×20 ml), dried (MgSO$_4$) and concentrated in vacuo to yield a white powder which is dried under high vacuum to yield the titled product. (MH+ 167).

99d) (6-Chloro-2-methyl-1H-pyrrolo[2,3-b]pyridin-3-yl)-oxo-acetic acid methyl ester A stirred suspension of aluminium chloride (0.56 g, 4.2 mmol) in DCM (10 ml) at room temperature under an inert atmosphere of Argon is treated with a solution of 6-chloro-2-methyl-1H-pyrrolo[2,3-b]pyridine: (0.14 g, 0.84 mmol) and stirred for 1 hour. Methyl oxalyl chloride (0.386 ml, 4.2 mmol) is added and the resulting suspension is stirred at room temperature overnight. The reaction mixture is cooled (0° C.) and quenched dropwise with methanol (10 ml). The resulting solution is poured into ice-water (100 ml) and the organic layer is separated, dried (Na$_2$SO$_4$) and concentrated in vacuo. The resulting crude is triturated with ice-cold water, sonicated and then filtered to afford a solid which, after drying under high vacuum, yields the titled compound. (MH+ 253).

99e) (6-Chloro-2-methyl-1H-pyrrolo[2,3-b]pyridin-3-yl)-acetic acid methyl ester

To a solution of triethylsilane (0.343 ml, 2.15 mmol) in TFA (2 ml) cooled to −10° C. is added portionwise (6-chloro-2-methyl-1H-pyrrolo[2,3-b]pyridin-3-yl)-oxo-acetic acid methyl ester (0.155 g, 0.61 mmol). The reaction mixture is stirred at −10° C. for 1 hour and the solvent is removed in vacuo. The residue is washed with saturated sodium hydrogen carbonate solution and this aqueous portion is extracted with DCM (3×10 ml). The organics are combined, dried (Na$_2$SO$_4$) and concentrated in vacuo and the resulting crude is purified by chromatography on silica eluting with methanol/DCM (0-0.5% methanol) to yield the titled product as an off-white powder. (MH+ 239).

99f) 6-Chloro-1-(4-methanesulfonyl-benzyl)-2-methyl-1H-pyrrolo[2,3-b]pyridin-3-yl]-acetic acid methyl ester To a stirred, ice-cooled solution of (6-chloro-2-methyl-1H-pyrrolo[2,3-b]pyridin-3-yl)-acetic acid methyl ester (0.045 g, 0.19 mmol) in DMF (1.5 ml) under an inert atmosphere of Argon is added sodium hydride (0.008 g of a 60% dispersion in mineral oil, 0.21 mmol). After stirring at 0° C. for 30 minutes, the reaction mixture is stirred at room temperature for two hours and then re-cooled to 0° C. 4-Methylsulphonylbenzyl bromide (0.076 g, 0.3 mmol) in DMF (1.5 ml) is added followed by sodium iodide (0.076 g, 0.30 mmol) and the resulting solution is stirred at room temperature overnight. The reaction mixture is poured onto water (20 ml) and extracted with 1:1 ethyl acetate/diethyl ether. The organic portions are washed with brine, dried (MgSO$_4$) and concentrated in vacuo. The resulting crude is purified by chromatography on silica eluting with ethyl acetate/iso-hexane (1:8 increasing to 1:4) to yield the titled product. (MH+ 407)

99g) [6-Chloro-1-(4-methanesulfonyl-benzyl)-2-methyl-1H-pyrrolo[2,3-b]pyridin-3-yl]-acetic acid 1M Aqueous NaOH (0.25 ml) is added to a stirring suspension of (6-chloro-2-methyl-1H-pyrrolo[2,3-b]pyridin-3-yl)-acetic acid methyl ester (0.018 g, 0.044 mmol) in 1:1 THF/MeOH (1 ml). After stirring at room temperature for 20 minutes the reaction mixture is evaporated to dryness. The resulting solid is dissolved in water (1 ml) and extracted with ethyl acetate to remove any residual 4-methylsulphonylbenzyl bromide. The aqueous phase is acidified to pH 2-3 using 2M HCl and extracted with ethyl acetate. The organic portion is concentrated in vacuo and the resulting crude is purified on silica eluting with DCM/MeOH (20:1) to yield the titled compound. (MH+ 393)

Example 100

[6-Chloro-1-(4-methanesulfonyl-2-trifluoromethyl-benzyl)-2-methyl-1H-pyrrolo[2,3-b]pyridin-3-yl]-acetic acid 100a) [6-Chloro-1-(4-methanesulfonyl-2-trifluoromethyl-benzyl)-2-methyl-1H-pyrrolo[2,3-b]pyridin-3-yl]-acetic acid methyl ester To a stirred, ice-cooled solution of (6-chloro-2-methyl-1H-pyrrolo[2,3-b]pyridin-3-yl)-acetic acid methyl ester (Example 99e) (0.03 g, 0.13 mmol) in DMF (1.0 ml) under an inert atmosphere of Argon is added sodium hydride (0.006 g of a 60% dispersion in mineral oil, 0.14 mmol). The reaction mixture is stirred at 0° C. for 45 minutes and then treated with 1-bromomethyl-4-methanesulfonyl-2-trifluoromethyl-benzene (Example 95a) (0.067 g, 0.21 mmol) followed by sodium iodide (0.031 g, 0.21 mmol). Stirring is continued at 0° C. for 2 hours and then the reaction mixture is poured onto water (15 ml) and extracted with DCM (5 ml). The organic portion is separated and concentrated in vacuo. The resulting crude is purified by chromatography on silica eluting with ethyl acetate/iso-hexane (1:8 increasing to 1:4) to yield the product which was further purified by trituration with ethyl acetate/iso-hexane to afford the titled product. (MH+ 475).

100b) [6-Chloro-1-(4-methanesulfonyl-2-trifluoromethyl-benzyl)-2-methyl-1H-pyrrolo[2,3-b]pyridin-3-yl]-acetic acid 1M Aqueous NaOH (0.25 ml) is added to a stirring suspension of [6-chloro-1-(4-methanesulfonyl-2-trifluoromethyl-benzyl)-2-methyl-1H-pyrrolo[2,3-b]pyridin-3-yl]-acetic acid methyl ester: (0.01 g, 0.021 mmol) in 1:1 THF/MeOH (0.5 ml). The resulting suspension is sonicated and allowed to stir at room temperature overnight. The solvent is removed in vacuo and the crude solid is dissolved in water (0.5 ml) and acidified to pH 2-3 using 1 N HCl. The suspension which forms is filtered, washed with water (0.5 ml) and dried under high vacuum to yield the titled compound. (MH+ 461)

Example 101

[2-Methyl-1-(3-methyl-3H-benzotriazol-5-ylmethyl)-1H-pyrrolo[2,3-b]pyridin-3-yl]-acetic acid 101a) 5-Bromomethyl-1-methyl-1H-benzotriazole Phosphorus tribromide (0.230 ml, 2.45 mmol) is added to a stirred solution of (1-methyl-1H-1,2,3-benzotriazole-5-yl) methanol (0.4 g, 2.45 mmol) in diethyl ether (25 ml) under an inert atmosphere of Argon. After stirring overnight at room temperature, the reaction mixture is diluted with water (5 ml) and stirred vigorously for 10 minutes. The organic portion is separated, washed with water (2×5 ml), brine (2×5 ml) and concentrated in vacuo to yield the titled product which is used crude in the next step. (MH+ 226).

101b) [2-Methyl-1-(3-methyl-3H-benzotriazol-5-ylmethyl)-1H-pyrrolo[2,3-b]pyridin-3-yl]-acetic acid methyl ester To a solution of (2-methyl-1H-pyrrolo[2,3-b]pyridin-3-yl)-acetic acid methyl ester ((0.025 g, 0.122 mmol) in dry DMF (1 ml) under an inert atmosphere of Argon is added dropwise, BEMP (56.6 μl, 0.196 mmol). The mixture is agitated at room temperature for 1 hour before cooling to 0° C. with an ice-bath. A solution of 5-bromomethyl-1-methyl-1H-benzotriazole (0.044 g, 0.196 mmol) in DMF (1 ml) is added to the cooled solution and the resulting mixture is agitated at room temperature for 2 days. The solvent is removed in vacuo and purification of the crude by chromatography on silica eluting with iso-hexane/ethyl acetate (0%-20% ethyl acetate) yields the titled product. (MH+ 350).

101c) [2-Methyl-1-(3-methyl-3H-benzotriazol-5-ylmethyl)-1H-pyrrolo[2,3-b]pyridin-3-yl]-acetic acid 1M Lithium hydroxide (116 μl) is added to a cooled (0° C.) solution of [2-methyl-1-(3-methyl-3H-benzotriazol-5-ylmethyl)-1H-pyrrolo[2,3-b]pyridin-3-yl]-acetic acid methyl ester (0.041 g, 0.116 mmol) in THF/water (4 ml of a 1:1 mixture). After stirring at room temperature for 4 hours, the reaction mixture is diluted with DCM (3 ml) and stirred vigorously for 10 minutes. The resulting mixture is passed through a phase separation cartridge and the aqueous portion is acidified to pH 1-3 with 1M HCl. This portion is extracted with DCM (2×3 ml) and the organic extracts are combined and concentrated in vacuo to yield the titled compound as a white solid. (MH+ 336)

Example 102

[1-(4-Fluoro-3-methoxy-benzenesulfonyl)-2-methyl-1H-pyrrolo[2,3-b]pyridin-3-yl]-acetic acid 102a) 4-Fluoro-3-methoxy-benzenesulfonyl chloride 4-Fluoro-3-methoxyaniline (0.5 g, 3.55 mmol) in suspension in glacial acetic acid (15 ml) is treated with a concentrated HCl (5 ml). The resulting solution is then cooled approximately to 0° C. and treated dropwise with a solution of sodium nitrite (0.245 g, 3.55 mmol) in water (2 ml). After 10 minutes the reaction mixture is added to a stirred solution of $SO_2$/AcOH/$CuCl_2$/$H_2O$ (40 ml) (the preparation of the reagent is described below). The reaction mixture is allowed to warm to room temperature and is stirred overnight. The reaction mixture is then poured into water (250 ml) and extracted with ethyl acetate (3×100 ml). The combined organic layers are washed with water (2×100 ml) followed by brine (100 ml) and dried over $MgSO_4$. After filtration the solvent is removed in vacuo to give the titled product which is used crude in the next step.

Preparation of the Reagent $SO_2$/AcOH/$CuCl_2$/$H_2O$:

According to the reported procedure (E. E. Gilbert, Synthesis 1969, 1-10, p 6), glacial acetic acid (100 ml), vigorously stirred at room temperature, is treated by bubbling $SO_2$ gas. Once a saturated solution is achieved (approximately 10 g per 100 ml), the solution is treated with copper (II) chloride (4 g) in water (5 ml). The resulting mixture is allowed to settle to give a green solution.

102b) [1-(4-Fluoro-3-methoxy-benzenesulfonyl)-2-methyl-1H-pyrrolo[2,3-b]pyridin-3-yl]-acetic acid methyl ester To a stirred, ice-cooled (0° C.) solution of sodium hydride (0.026 g of a 60% dispersion in mineral oil, 0.686 mmol) in THF (3 ml) under an inert atmosphere of Argon is added dropwise (2-methyl-1H-pyrrolo[2,3-b]pyridin-3-yl)-acetic acid methyl ester ((0.1 g, 0.49 mmol) in dry THF (3 ml). The reaction mixture is stirred at 0° C. for 1 hour and then treated with 4-fluoro-3-methoxy-benzenesulfonyl chloride (0.154 g, 0.686 mmol) in dry THF (3 ml). Stirring continued at 0° C. for 30 minutes and then the reaction mixture is poured onto water (100 ml) and extracted with ethyl acetate (3×50 ml). The organic portions are separated and washed with water (2×50 ml), brine (50 ml), dried ($MgSO_4$) and concentrated in vacuo. The resulting crude is purified by chromatography on silica eluting with iso-hexane/ethyl acetate (0%-20% ethyl acetate) yields the titled product. (MH+ 392).

102c) [1-(4-Fluoro-3-methoxy-benzenesulfonyl)-2-methyl-1H-pyrrolo[2,3-b]pyridin-3-yl]-acetic acid 1M Lithium hydroxide (119 μl) is added dropwise to a cooled (0° C.) solution of [1-(4-fluoro-3-methoxy-benzenesulfonyl)-2-methyl-1H-pyrrolo[2,3-b]pyridin-3-yl]-acetic acid methyl ester (0.044 g, 0.119 mmol) in THF/water (4 ml of a 1:1 mixture). After stirring at room temperature for 4 hours, the reaction mixture is diluted with DCM. The resulting mixture is passed through a phase separation cartridge and the aqueous portion is acidified to pH 1-3 with 1M HCl. This portion is extracted with DCM and the organic extracts are combined and concentrated in vacuo to yield the titled compound as a pale yellow solid. (MH+ 379)

Example 103

[1-(4-Chloro-3-cyano-benzenesulfonyl)-2-methyl-1H-pyrrolo[2,3-b]pyridin-3-yl]-acetic acid 103a) 4-Chloro-3-cyano-benzenesulfonyl chloride A suspension of 2-chloro-5-aminobenzonitrile (0.405 g, 2.66 mmol) in glacial acetic acid (20 ml) is treated with concentrated HCl (5 ml). The solution is cooled to below 5° C. and treated dropwise with sodium nitrite (0.183 g, 2.66 mmol) in water (2 ml). After 20 minutes the reaction mixture is added to a stirred solution of $SO_2$/AcOH/$CuCl_2$/$H_2O$ (40 ml) (the preparation of the reagent is described herein). The reaction mixture is allowed to warm to room temperature and is stirred overnight. The reaction mixture is then poured into water (150 ml) and extracted with ethyl acetate (3×100 ml). The combined organic layers are washed with water (2×100 ml) followed by brine (100 ml) and dried over MgSO4. After filtration the solvent is removed in vacuo to give the titled product which is used crude in the next step.

103b) 1-(4-Chloro-3-cyano-benzenesulfonyl)-2-methyl-1H-pyrrolo[2,3-b]pyridin-3-yl]-acetic acid methyl ester To a stirred, ice-cooled (0° C.) suspension of sodium hydride (15.8 mg of a 60% dispersion in mineral oil, 0.411 mmol) in dry THF (2 ml) under an inert atmosphere of Argon is added dropwise (2-methyl-1H-pyrrolo[2,3-b]pyridin-3-yl)-acetic acid methyl ester ((0.06 g, 0.294 mmol) in THF/DMF (4 ml of a 3:1 mixture). The reaction mixture is stirred at 0° C. for 45 minutes and then treated with 4-chloro-3-cyano-benzenesulfonyl chloride (97.1 mg, 0.411 mmol) in dry THF (3 ml). Stirring continued at 0° C. for 15 minutes and then the reaction mixture is poured onto water (30 ml) and extracted with ethyl acetate (100 ml). The organic portion is separated and washed brine (50 ml), dried (MgSO$_4$) and concentrated in vacuo. The resulting crude is purified by chromatography on silica eluting with iso-hexane/ethyl acetate (0%-20% ethyl acetate) to yield the titled product. (MH+ 404)

103c) [1-(4-Chloro-3-cyano-benzenesulfonyl)-2-methyl-1H-pyrrolo[2,3-b]pyridin-3-yl]-acetic acid 1M Lithium hydroxide (76 μl) is added dropwise to a cooled (0° C.) solution of 1-(4-chloro-3-cyano-benzenesulfonyl)-2-methyl-1H-pyrrolo[2,3-b]pyridin-3-yl]-acetic acid methyl ester (0.026 g, 0.064 mmol) in THF/water (4 ml of a 1:1 mixture). After stirring at 0° C. for 10 minutes, the reaction mixture is allowed to warm to room temperature overnight and then diluted with DCM (3 ml). The resulting mixture is passed through a phase separation cartridge and the aqueous portion is acidified to pH 1-3 with 1M HCl. This portion is extracted with DCM (2×3 ml) and the organic extracts are combined, passed through a phase separation cartridge, and concentrated in vacuo to yield the titled compound as an off-white solid. (MH+ 390)

Examples 104-105

These Examples, namely
[2-Methyl-1-(4-trifluoromethanesulfonyl-benzyl)-1H-pyrrolo[2,3-b]pyridin-3-yl]-acetic acid (Example 104) and
{2-Methyl-1-[4-(propane-2-sulfonyl)-benzyl]-1H-pyrrolo[2,3-b]pyridin-3-yl}-acetic acid (Example 105) are prepared analogously to Example 90 using the appropriate benzyl halide. The preparation of these benzyl halides is described herein.

Examples 106-111

These Examples, namely
[1-(3-Fluoro-4-methoxy-benzyl)-2-methyl-1H-pyrrolo[2,3-b]pyridin-3-yl]-acetic acid (Example 106),
[1-(4-Fluoro-3-methoxy-benzyl)-2-methyl-1H-pyrrolo[2,3-b]pyridin-3-yl]-acetic acid (Example 107),
[2-Methyl-1-(6-trifluoromethyl-pyridin-3-ylmethyl)-1H-pyrrolo[2,3-b]pyridin-3-yl]-acetic acid (Example 108),
[1-(3-Cyano-4-fluoro-benzyl)-2-methyl-1H-pyrrolo[2,3-b]pyridin-3-yl]-acetic acid (Example 109),
[1-(2-Chloro-5-fluoro-benzyl)-2-methyl-1H-pyrrolo[2,3-b]pyridin-3-yl]-acetic acid (Example 110) and
[1-(4-Chloro-3-methoxy-benzyl)-2-methyl-1H-pyrrolo[2,3-b]pyridin-3-yl]-acetic acid (Example 111), are prepared analogously to Example 96 using the appropriate benzyl halide. The benzyl halides that are used to prepare these Examples are either commercially available or are prepared by methods described herein.

Examples 112-126

These examples, namely
[1-(4-Methanesulfonyl-2-methyl-benzyl)-2-methyl-1H-pyrrolo[2,3-b]pyridin-3-yl]-acetic acid (Example 112),
[1-(4-Methoxy-benzyl)-2-methyl-1H-pyrrolo[2,3-b]pyridin-3-yl]-acetic acid (Example 113),
[1-(2-Methoxy-benzyl)-2-methyl-1H-pyrrolo[2,3-b]pyridin-3-yl]-acetic acid (Example 114),
{2-Methyl-1-[1-(4-trifluoromethyl-phenyl)-ethyl]-1H-pyrrolo[2,3-b]pyridin-3-yl}-acetic acid (Example 115),
{1-[1-(3-Chloro-phenyl)-ethyl]-2-methyl-1H-pyrrolo[2,3-b]pyridin-3-yl}-acetic acid (Example 116),
{1-[1-(4-Methanesulfonyl-phenyl)-ethyl]-2-methyl-1H-pyrrolo[2,3-b]pyridin-3-yl}-acetic acid (Example 117),
1-(4-Fluoro-2-trifluoromethyl-benzyl)-2-methyl-1H-pyrrolo[2,3-b]pyridin-3-yl]-acetic acid (Example 118),
[1-(2,4-Bis-trifluoromethyl-benzyl)-2-methyl-1H-pyrrolo[2,3-b]pyridin-3-yl]-acetic acid (Example 119),
{2-Methyl-1-[1-(2-trifluoromethyl-phenyl)-ethyl]-1H-pyrrolo[2,3-b]pyridin-3-yl}-acetic acid (Example 120),
[1-(3-Methanesulfonyl-benzyl)-2-methyl-1H-pyrrolo[2,3-b]pyridin-3-yl]-acetic acid (Example 121),
[2-Methyl-1-(4-nitro-benzyl)-1H-pyrrolo[2,3-b]pyridin-3-yl]-acetic acid (Example 122),
[1-(4-Bromo-benzyl)-2-methyl-1H-pyrrolo[2,3-b]pyridin-3-yl]-acetic acid (Example 123),
[2-Methyl-1-(4-[1,2,4]triazol-1-yl-benzyl)-1H-pyrrolo[2,3-b]pyridin-3-yl]-acetic acid (Example 124),
[1-(3-Chloro-4-methanesulfonyl-benzyl)-2-methyl-1H-pyrrolo[2,3-b]pyridin-3-yl]-acetic acid (Example 125) and
[1-(3-Fluoro-4-methanesulfonyl-benzyl)-2-methyl-1H-pyrrolo[2,3-b]pyridin-3-yl]-acetic acid (Example 126)

are prepared analogously to Example 91 using the appropriate benzyl halide. The benzyl halides that are used to prepare these Examples are either commercially available or are prepared by methods described herein.

4-Bromomethyl-2-fluoro-1-methanesulfonyl-benzene a) 3-Fluoro-4-methanesulfonyl-benzaldehyde Methane sulfinic acid sodium salt (20.1 g, 200 mmol) is added to a stirred solution of 3,4-difluorobenzaldehyde (22.5 g, 158 mmol) in dry DMSO (200 ml) at 75° C. After 2 hours the reaction is poured onto ice-water (200 ml). The precipitate is filtered, washed with water and dissolved in chloroform (400 ml). The organic extract is washed with water (2×200 ml), dried over MgSO4 and the solvent is removed in vacuo to give the titled compound as a white solid.

b) (3-Fluoro-4-methanesulfonyl-phenyl)-methanol

To an ice-cooled suspension of 3-fluoro-4-methanesulfonyl-benzaldehyde (1.3 g, 6.44 mmol) in ethanol (5 ml) under an inert atmosphere of Argon is added sodium borohydride (0.275 g, 7.27 mmol) portionwise over 2-3 minutes. After stirring for 4 hours, the reaction mixture is poured carefully onto ice-cold water and acidified to pH 1 using 1M HCl. The product is extracted into ethyl acetate (80 ml) and this organic portion is washed with brine, dried over MgSO4 and the solvent is removed in vacuo to give an oil which solidifies on drying to yield the titled compound.

c) 4-Bromomethyl-2-fluoro-1-methanesulfonyl-benzene

To a stirred suspension of (3-fluoro-4-methanesulfonyl-phenyl)-methanol (0.269 g, 1.31 mmol) in diethyl ether (5 ml) under an inert atmosphere of Argon is added dropwise phosphorus tribromide (46 μl, 0.434 mmol). After stirring at room temperature overnight, the reaction mixture is diluted with water (2 ml) and the diethyl ether layer separated. This organic portion is placed over NaOH pellets and after 20 minutes, is used as a reagent in solution in diethyl ether.

1-Bromomethyl-4-methanesulfonyl-2-methyl-benzene

The titled compound is prepared analogously to 4-bromomethyl-2-fluoro-1-methanesulfonyl-benzene by replacing 3,4-difluorobenzaldehyde with 4-fluoro-2-methyl-benzaldehyde.

1-Bromomethyl-4-trifluoromethanesulfonyl-benzene

The titled compound is prepared analogously to 4-bromomethyl-2-fluoro-1-methanesulfonyl-benzene by replacing 3-fluoro-4-methanesulfonyl-benzaldehyde with 4-trifluoromethanesulfonyl-benzaldehyde.

4-Bromomethyl-2-chloro-1-methanesulfonyl-benzene

The titled compound is prepared analogously to 4-bromomethyl-2-fluoro-1-methanesulfonyl-benzene by replacing 3,4-difluorobenzaldehyde with 3-chloro-4-fluoro-benzaldehyde.

1-Bromomethyl-4-(propane-2-sulfonyl)-benzene

The titled compound is prepared analogously to 4-bromomethyl-2-fluoro-1-methanesulfonyl-benzene by replacing 3,4-difluorobenzaldehyde with 4-fluorobenzaldehyde and by replacing methane sulfinic acid sodium salt with 2-propane sulfinic acid sodium salt.

Examples 127

[1-(4-Cyano-3-ethoxy-benzenesulfonyl)-2-methyl-1H-pyrrolo[2,3-b]pyridin-3-yl]-acetic acid 127a) 2-Ethoxy-4-nitro-benzonitrile To a solution of 2-hydroxy-4-nitrobenzonitrile (0.5 g, 3.04 mmol) in DMF (5 ml) is added potassium carbonate (0.631 g, 4.56 mmol) followed by bromoethane (0.238 ml, 3.19 mmol) and the reaction mixture is stirred at room temperature for 5 days. The solvent is removed in vacuo and the crude is partitioned between ethyl acetate (100 ml) and water (100 ml). The organic layer is separated, washed with water (2×100 ml), saturated sodium hydrogen carbonate solution (100 ml) and concentrated in vacuo to afford the titled compound as a pale yellow solid which is used crude in the next step.

127b) 4-Amino-2-ethoxy-benzonitrile

To a suspension of 2-ethoxy-4-nitro-benzonitrile (0.49 g, 2.54 mmol) in ethanol (50 ml) is added tin (II) chloride dihydrate (2.87 g, 12.7 mmol) and the suspension is stirred at 70° C. for 2 hours and at room temperature overnight. The reaction mixture is poured onto ice-water and the pH of the solution is adjusted to pH 7-8 by addition of sodium hydrogen carbonate solution (5% solution in water). The aqueous emulsion is filtered under vacuum and the product is extracted with ethyl acetate (2×150 ml). The organic portions are combined, washed with brine (100 ml), dried (MgSO$_4$) and concentrated in vacuo to yield the titled product as a pale yellow solid which is used in the next step without further purification.

127c) 4-Cyano-3-ethoxy-benzenesulfonyl chloride

The titled compound is prepared analogously to 4-fluoro-3-methoxy-benzenesulfonyl chloride (Intermediate 102a) by replacing 4-fluoro-3-methoxyaniline with 4-amino-2-ethoxy-benzonitrile.

127d) [1-(4-Cyano-3-ethoxy-benzenesulfonyl)-2-methyl-1H-pyrrolo[2,3-b]pyridin-3-]-acetic acid methyl ester To a stirred, ice-cooled (0° C.) suspension of sodium hydride (26.3 mg of a 60% dispersion in mineral oil, 0.686 mmol) in dry THF (10 ml) under an inert atmosphere of Argon is added dropwise (2-methyl-1H-pyrrolo[2,3-b]pyridin-3-yl)-acetic acid methyl ester ((0.1 g, 0.49 mmol) in THF/DMF (4 ml of a 3:1 mixture). The reaction mixture is stirred at 0° C. for 1 hour and then treated with 4-cyano-3-ethoxy-benzenesulfonyl chloride (168 mg, 0.686 mmol) in dry THF (1 ml). Stirring continued at 0° C. for 10 minutes and at room temperature for 10 minutes and then the reaction mixture is poured onto water (50 ml). The mixture is extracted with ethyl acetate (2×50 ml) and the organic portions are combined, washed brine (50 ml), dried (MgSO$_4$) and concentrated in vacuo. The resulting crude is purified by chromatography on silica eluting with iso-hexane/ethyl acetate (0%-20% ethyl acetate) to yield the titled product. (MH+ 414).

127 e) [1-(4-Cyano-3-ethoxy-benzenesulfonyl)-2-methyl-1H-pyrrolo[2,3-b]pyridin-3-yl]-acetic acid 1M Lithium hydroxide (57 µl) is added dropwise to a cooled (0° C.) solution of [1-(4-cyano-3-ethoxy-benzenesulfonyl)-2-methyl-1H-pyrrolo[2,3-b]pyridin-3-yl]-acetic acid methyl ester (0.024 g, 0.057 mmol) in THF/water (4 ml of a 1:1 mixture). After stirring at 0° C. for 10 minutes, the reaction mixture is stirred at room temperature for 2.5 hours and then diluted with DCM (4 ml). The resulting mixture is passed through a phase separation cartridge and the aqueous portion is acidified to pH 4 with 1M HCl. This portion is extracted with DCM (2×4 ml) and the organic extracts are combined, passed through a phase separation cartridge, and concentrated in vacuo. The resulting solid is dissolved in ethyl acetate (2 ml) and triturated with iso-hexane (7 ml) to yield the titled compound as a white solid. (MH+ 400)

Examples 128-150

These Examples, namely
[1-(3-Fluoro-2-methyl-benzenesulfonyl)-2-methyl-1H-pyrrolo[2,3-b]pyridin-3-yl]-acetic acid (Example 128),
[1-(4-Cyano-3-methoxy-benzenesulfonyl)-2-methyl-1H-pyrrolo[2,3-b]pyridin-3-yl]-acetic acid (Example 129),
[1-(4-Cyano-3-propoxy-benzenesulfonyl)-2-methyl-1H-pyrrolo[2,3-b]pyridin-3-yl]-acetic acid (Example 130),
[1-(3-Butoxy-4-cyano-benzenesulfonyl)-2-methyl-1H-pyrrolo[2,3-b]pyridin-3-yl]-acetic acid (Example 131),
[1-(4-Cyano-3-pentyloxy-benzenesulfonyl)-2-methyl-1H-pyrrolo[2,3-b]pyridin-3-yl]-acetic acid (Example 132),
[1-(6-Cyano-pyridine-3-sulfonyl)-2-methyl-1H-pyrrolo[2,3-b]pyridin-3-yl]-acetic acid (Example 133),
[1-(2-Chloro-5-cyano-benzenesulfonyl)-2-methyl-1H-pyrrolo[2,3-b]pyridin-3-yl]-acetic acid (Example 134),
[1-(4-Cyano-3-methyl-benzenesulfonyl)-2-methyl-1H-pyrrolo[2,3-b]pyridin-3-yl]-acetic acid (Example 135),
[1-(4-Chloro-2-fluoro-5-methoxy-benzenesulfonyl)-2-methyl-1H-pyrrolo[2,3-b]pyridin-3-yl]-acetic acid (Example 136),
[1-(5-Cyano-2-methoxy-benzenesulfonyl)-2-methyl-1H-pyrrolo[2,3-b]pyridin-3-yl]-acetic acid (Example 137),
[1-(5-Chloro-2-cyano-benzenesulfonyl)-2-methyl-1H-pyrrolo[2,3-b]pyridin-3-yl]-acetic acid (Example 138),
[1-(2-Chloro-4-cyano-benzenesulfonyl)-2-methyl-1H-pyrrolo[2,3-b]pyridin-3-yl]-acetic acid (Example 139),
[1-(2-Chloro-5-methoxy-benzenesulfonyl)-2-methyl-1H-pyrrolo[2,3-b]pyridin-3-yl]-acetic acid (Example 140),
[1-(5-Chloro-2-methoxy-benzenesulfonyl)-2-methyl-1H-pyrrolo[2,3-b]pyridin-3-yl]-acetic acid (Example 141),
[2-Methyl-1-(thiophene-2-sulfonyl)-1H-pyrrolo[2,3-b]pyridin-3-yl]-acetic acid (Example 142),
[1-(4-Cyano-3-trifluoromethyl-benzenesulfonyl)-2-methyl-1H-pyrrolo[2,3-b]pyridin-3-yl]-acetic acid (Example 143),
[1-(3-Chloro-4-cyano-benzenesulfonyl)-2-methyl-1H-pyrrolo[2,3-b]pyridin-3-yl]-acetic acid (Example 144),
[1-(4-Chloro-3-fluoro-benzenesulfonyl)-2-methyl-1H-pyrrolo[2,3-b]pyridin-3-yl]-acetic acid (Example 145),
[1-(3-Chloro-4-trifluoromethyl-benzenesulfonyl)-2-methyl-1H-pyrrolo[2,3-b]pyridin-3-yl]-acetic acid (Example 146),
[1-(3-Fluoro-4-trifluoromethyl-benzenesulfonyl)-2-methyl-1H-pyrrolo[2,3-b]pyridin-3-yl]-acetic acid (Example 147),
[1-(4-Chloro-3-methoxy-benzenesulfonyl)-2-methyl-1H-pyrrolo[2,3-b]pyridin-3-yl]-acetic acid (Example 148),
[1-(3,4-Dicyano-benzenesulfonyl)-2-methyl-1H-pyrrolo[2,3-b]pyridin-3-yl]-acetic acid (Example 149) and
[1-(4-Chloro-3-trifluoromethyl-benzenesulfonyl)-2-methyl-1H-pyrrolo[2,3-b]pyridin-3-yl]-acetic acid (Example 150) are prepared analogously to Example 127 using the appropriate sulphonyl chloride. The sulphonyl chlorides that are used to prepare these Examples are either commercially available or are prepared by methods described herein.

4-Cyano-3-methoxy-benzenesulfonyl chloride

The titled compound was prepared analogously to 4-cyano-3-ethoxy-benzenesulfonyl chloride (Intermediate 127c) by replacing 2-ethoxy-4-nitro-benzonitrile with 2-methoxy-4-nitro-benzonitrile.

4-Cyano-3-propoxy-benzenesulfonyl chloride

The titled compound was prepared analogously to 4-cyano-3-ethoxy-benzenesulfonyl chloride (Intermediate 127c) by replacing bromoethane with 1-bromopropane.

3-Butoxy-4-cyano-benzenesulfonyl chloride

The titled compound was prepared analogously to 4-cyano-3-ethoxy-benzenesulfonyl chloride (Intermediate 127c) by replacing bromoethane with 1-bromobutane.

4-Cyano-3-pentyloxy-benzenesulfonyl chloride

The titled compound was prepared analogously to 4-cyano-3-ethoxy-benzenesulfonyl chloride (Intermediate 127c) by replacing bromoethane with 1-bromopentane.

6-Cyano-pyridine-3-sulfonyl chloride

The titled compound is prepared analogously to 4-fluoro-3-methoxy-benzenesulfonyl chloride (Intermediate 102a) by replacing 4-fluoro-3-methoxyaniline with 5-amino-pyridine-2-carbonitrile.

2-Chloro-5-cyano-benzenesulfonyl chloride

The titled compound is prepared analogously to 4-fluoro-3-methoxy-benzenesulfonyl chloride (Intermediate 102a) by replacing 4-fluoro-3-methoxyaniline with 3-amino-4-chloro-benzonitrile.

4-Cyano-3-methyl-benzenesulfonyl chloride

The titled compound was prepared analogously to 4-cyano-3-ethoxy-benzenesulfonyl chloride (Intermediate 127c) by replacing 2-ethoxy-4-nitro-benzonitrile with 2-methyl-4-nitro-benzonitrile.

4-Chloro-2-fluoro-5-methoxy-benzenesulfonyl chloride

The titled compound was prepared analogously to 4-cyano-3-ethoxy-benzenesulfonyl chloride (Intermediate 127c) by replacing 2-ethoxy-4-nitro-benzonitrile with 1-chloro-5-fluoro-2-methoxy-4-nitro-benzene.

5-Cyano-2-methoxy-benzenesulfonyl chloride

The titled compound was prepared analogously to 4-cyano-3-ethoxy-benzenesulfonyl chloride (Intermediate 127c) by replacing 2-ethoxy-4-nitro-benzonitrile with 4-methoxy-3-nitro-benzonitrile.

5-Chloro-2-cyano-benzenesulfonyl chloride

The titled compound is prepared analogously 4-fluoro-3-methoxy-benzenesulfonyl chloride (Intermediate 102a) by replacing 4-fluoro-3-methoxyaniline with 2-amino-4-chloro-benzonitrile.

2-Chloro-5-methoxy-benzenesulfonyl chloride

The titled compound is prepared analogously to 4-fluoro-3-methoxy-benzenesulfonyl chloride (Intermediate 102a) by replacing 4-fluoro-3-methoxyaniline with 2-chloro-5-methoxy-phenylamine.

4-Cyano-3-trifluoromethyl-benzenesulfonyl chloride

The titled compound is prepared analogously to 4-fluoro-3-methoxy-benzenesulfonyl chloride (Intermediate 102a) by replacing 4-fluoro-3-methoxyaniline with 4-amino-2-trifluoromethyl-benzonitrile.

3-Chloro-4-cyano-benzenesulfonyl chloride

The titled compound is prepared analogously to 4-fluoro-3-methoxy-benzenesulfonyl chloride (Intermediate 102a) by replacing 4-fluoro-3-methoxyaniline with 4-amino-2-chloro-benzonitrile.

4-Chloro-3-fluoro-benzenesulfonyl chloride

The titled compound is prepared analogously to 4-fluoro-3-methoxy-benzenesulfonyl chloride (Intermediate 102a) by replacing 4-fluoro-3-methoxyaniline with 4-chloro-3-fluoro-phenylamine.

3-Chloro-4-trifluoromethyl-benzenesulfonyl chloride

The titled compound is prepared analogously to 4-fluoro-3-methoxy-benzenesulfonyl chloride (Intermediate 102a) by replacing 4-fluoro-3-methoxyaniline with 3-chloro-4-trifluoromethyl-phenylamine.

3-Fluoro-4-trifluoromethyl-benzenesulfonyl chloride

The titled compound is prepared analogously to 4-fluoro-3-methoxy-benzenesulfonyl chloride (Intermediate 102a) by replacing 4-fluoro-3-methoxyaniline with 3-fluoro-4-trifluoromethyl-phenylamine.

4-Chloro-3-methoxy-benzenesulfonyl chloride

The titled compound is prepared analogously to 4-fluoro-3-methoxy-benzenesulfonyl chloride (Intermediate 102a) by replacing 4-fluoro-3-methoxyaniline with 4-chloro-3-methoxy-phenylamine.

4-Chloro-3-trifluoromethyl-benzenesulfonyl chloride

The titled compound is prepared analogously to 4-fluoro-3-methoxy-benzenesulfonyl chloride (Intermediate 102a) by replacing 4-fluoro-3-methoxyaniline with 4-chloro-3-trifluoromethyl-phenylamine.

3,4-Dicyano-benzenesulfonyl chloride

The titled compound is prepared analogously to 4-fluoro-3-methoxy-benzenesulfonyl chloride (Intermediate 102a) by replacing 4-fluoro-3-methoxyaniline with 4-amino-phthalonitrile.

Example 151

[1-(3-Cyano-4-morpholin-4-yl-benzenesulfonyl)-2-methyl-1H-pyrrolo[2,3-b]pyridin-3-yl]-acetic acid 151a) [1-(3-Cyano-4-morpholin-4-yl-benzenesulfonyl)-2-methyl-1H-pyrrolo[2,3-b]pyridin-3-yl]-acetic acid methyl ester To a solution of [1-(3-cyano-4-fluoro-benzenesulfonyl)-2-methyl-1H-pyrrolo[2,3-b]pyridin-3-yl]-acetic acid methyl ester (Example 54a) (60.7 mg, 0.157 mmol) in acetonitrile (3 ml) is added potassium carbonate (43.3 mg, 0.314 mmol) followed by morpholine (27.6 µl, 0.314 mmol). The reaction mixture is stirred at room temperature for 2 hours and then filtered and concentrated in vacuo to yield the titled compound as an orange oil which is used crude in the next step. (MH+ 455).

151b) [1-(3-Cyano-4-morpholin-4-yl-benzenesulfonyl)-2-methyl-1H-pyrrolo[2,3-b]pyridin-3-yl]-acetic acid The titled compound is prepared analogously to [1-(4-fluoro-3-methoxy-benzenesulfonyl)-2-methyl-1H-pyrrolo[2,3-b]pyridin-3-yl]-acetic acid (Example 102) by replacing [1-(4-fluoro-3-methoxy-benzenesulfonyl)-2-methyl-1H-pyrrolo[2,3-b]pyridin-3-yl]-acetic acid methyl ester with [1-(3-cyano-4-morpholin-4-yl-benzenesulfonyl)-2-methyl-1H-pyrrolo[2,3-b]pyridin-3-yl]-acetic acid methyl ester. (MH+ 441)

Example 152

[1-(3-Fluoro-4-morpholin-4-yl-benzenesulfonyl)-2-methyl-1H-pyrrolo[2,3-b]pyridin-3-yl]-acetic acid The titled compound is prepared analogously to [1-(3-cyano-4-morpholin-4-yl-benzenesulfonyl)-2-methyl-1H-pyrrolo[2,3-b]pyridin-3-yl]-acetic acid methyl ester (Intermediate 151b) by replacing [1-(3-cyano-4-fluoro-benzenesulfonyl)-2-methyl-1H-pyrrolo[2,3-b]pyridin-3-yl]-acetic acid methyl ester with [1-(3,4-difluoro-benzenesulfonyl)-2-methyl-1H-pyrrolo[2,3-b]pyridin-3-yl]-acetic acid (Example 59) and by heating using microwave radiation in a Personal Chemistry Emrys™ Optimizer microwave reactor at 60-80° C. for 4 hours. (MH+ 434)

Example 153

[1-(4-Chloro-3-cyano-benzenesulfonyl)-2-ethyl-1H-pyrrolo[2,3-b]pyridin-3-yl]-acetic acid The titled compound is prepared analogously to [1-(4-chloro-3-cyano-benzenesulfonyl)-2-methyl-1H-pyrrolo[2,3-b]pyridin-3-yl]-acetic acid (Example 103) by replacing (2-methyl-1H-pyrrolo[2,3-b]pyridin-3-yl)-acetic acid methyl ester with (2-ethyl-1H-pyrrolo[2,3-b]pyridin-3-yl)-acetic acid methyl ester (Intermediate 87c). (MH+ 404)

The invention claimed is:
1. A compound of formula (I)

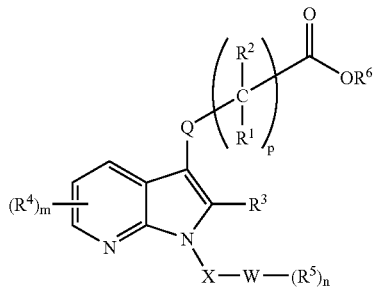

in free or salt form,
wherein
Q is a bond;
$R^1$ and $R^2$ are, independently, H, or $C_1$-$C_8$-alkyl;
$R^3$ is $C_1$-$C_8$-alkyl;
$R^4$ and $R^5$ are, independently, halogen, $C_1$-$C_8$-alkyl, $C_1$-$C_8$-haloalkyl, a $C_3$-$C_{15}$-carbocyclic group, nitro, cyano, $C_1$-$C_8$-alkylsulfonyl, $C_1$-$C_8$-alkoxycarbonyl, $C_1$-$C_8$-alkoxy, $C_1$-$C_8$-haloalkoxy;
$R^6$ is H or $C_1$-$C_8$-alkyl;
W is a group of formula ($W_{a1}$) or ($W_{a2}$)

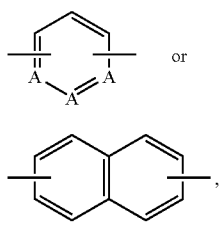

wherein A is, independently, C or N, or
W is a group of formula ($W_b$);

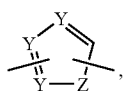

wherein
Y is, independently, C or N; and
Z is N, O or S, or
W is a group of formula ($W_c$)

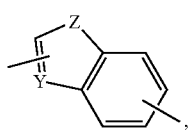

wherein
Y is, independently, C or N; and
Z is O or S;

X is —$CH_2$—, —$CON(C_1$-$C_8$-alkyl)-, —$CH(C_1$-$C_8$-alkyl)- or a bond;
m and n are each, independently, an integer from 0-3; and
p is 1.

2. The compound of formula (I) according to claim 1, in free or salt form
wherein
Q is a bond;
$R^1$ and $R^2$ are, independently, H or $C_1$-$C_4$-alkyl;
$R^3$ is $C_1$-$C_4$-alkyl;
$R^4$ and $R^5$ are, independently, halogen, $C_1$-$C_4$-alkyl, $C_1$-$C_4$-haloalkyl, a $C_3$-$C_{10}$-carbocyclic group, cyano, $C_1$-$C_4$-alkylsulfonyl, $C_1$-$C_4$-alkoxycarbonyl, $C_1$-$C_4$-alkoxy or $C_1$-$C_4$-haloalkoxy;
$R^6$ is H or $C_1$-$C_4$-alkyl;
W is a group of formula ($W_{a1}$) or ($W_{a2}$)

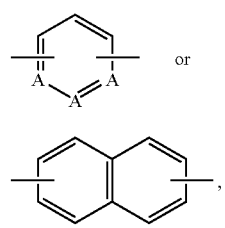

wherein A is, independently, C or N, or
W is a group of formula ($W_b$);

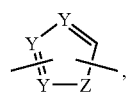

wherein
Y is, independently, C or N; and
Z is N, O or S;
X is —$CH_2$—, or —$CH(C_1$-$C_4$-alkyl);
m and n are each, independently, an integer from 0-3; and
p is 1.

3. A pharmaceutical composition, comprising:
the compound according to claim 1 and
pharmaceutically acceptable carrier.

4. The compound of claim 1 selected from:
[1-(3,4-Dichloro-benzyl)-2-methyl-1H-pyrrolo[2,3-b]pyridin-3-yl]-acetic acid;
[2-Methyl-1-(2-methyl-benzyl)-1H-pyrrolo[2,3-b]pyridin-3-yl]-acetic acid;
2-Methyl-1-pyridin-3-ylmethyl-1H-pyrrolo[2,3-b]pyridin-3-yl)-acetic acid;
(2-Methyl-1-pyridin-2-ylmethyl-1H-pyrrolo[2,3-b]pyridin-3-yl)-acetic acid;
(2-Methyl-1-pyridin-4-ylmethyl-1H-pyrrolo[2,3-b]pyridin-3-yl)-acetic acid;
[1-(4-Chloro-benzyl)-2-methyl-1H-pyrrolo[2,3-b]pyridin-3-yl]-acetic acid;
[1-(3-Cyano-benzyl)-2-methyl-1H-pyrrolo[2,3-b]pyridin-3-yl]-acetic acid;
[1-(3-Chloro-benzyl)-2-methyl-1H-pyrrolo[2,3-b]pyridin-3-yl]-acetic acid;
[1-(4-Cyano-benzyl)-2-methyl-1H-pyrrolo[2,3-b]pyridin-3-yl]-acetic acid;

[2-Methyl-1-(3-methyl-benzyl)-1H-pyrrolo[2,3-b]pyridin-3-yl]-acetic acid;
[2-Methyl-1-(3-trifluoromethyl-benzyl)-1H-pyrrolo[2,3-b]pyridin-3-yl]-acetic acid;
[1-(4-Fluoro-benzyl)-2-methyl-1H-pyrrolo[2,3-b]pyridin-3-yl]-acetic acid;
[1-(2-Chloro-benzyl)-2-methyl-1H-pyrrolo[2,3-b]pyridin-3-yl]-acetic acid;
[2-Methyl-1-(4-trifluoromethyl-benzyl)-1H-pyrrolo[2,3-b]pyridin-3-yl]-acetic acid;
[1-(3-Fluoro-benzyl)-2-methyl-1H-pyrrolo[2,3-b]pyridin-3-yl]-acetic acid;
[1-(4-Chloro-phenyl)-2-methyl-1H-pyrrolo[2,3-b]pyridin-3-yl]-acetic acid;
(1-Furan-3-ylmethyl-2-methyl-1H-pyrrolo[2,3-b]pyridin-3-yl)-acetic acid;
[1-(3,4-Difluoro-benzyl)-2-methyl-1H-pyrrolo[2,3-b]pyridin-3-yl]-acetic acid;
(1-furan-2-ylmethyl-2-methyl-1H-pyrrolo[2,3-b]pyridin-3-yl)-acetic acid
[2-Methyl-1-(4-methyl-benzyl)-1H-pyrrolo[2,3-b]pyridin-3-yl]-acetic acid;
[1-(4-Fluoro-3-methyl-benzyl)-2-methyl-1H-pyrrolo[2,3-b]pyridin-3-yl]-acetic acid;
[1-(3-Fluoro-4-methyl-benzyl)-2-methyl-1H-pyrrolo[2,3-b]pyridin-3-yl]-acetic acid;
[1-(3-Chloro-4-fluoro-benzyl)-2-methyl-1H-pyrrolo[2,3-b]pyridin-3-yl]-acetic acid;
[1-(3-Fluoro-4-trifluoromethyl-benzyl)-2-methyl-1H-pyrrolo[2,3-b]pyridin-3-yl]-acetic acid;
[1-(4-Chloro-3-trifluoromethyl-benzyl)-2-methyl-1H-pyrrolo[2,3-b]pyridin-3-yl]-acetic acid;
[1-(2,5-Dimethyl-2H-pyrazol-3-ylmethyl)-2-methyl-1H-pyrrolo[2,3-b]pyridin-3-yl]-acetic acid;
[1-(3,5-Dimethyl-isoxazol-4-ylmethyl)-2-methyl-1H-pyrrolo[2,3-b]pyridin-3-yl]-acetic acid;
[2-Methyl-1-(5-methyl-2-trifluoromethyl-furan-3-ylmethyl)-1H-pyrrolo[2,3-b]pyridin-3-yl]-acetic acid;
[2-Methyl-1-(5-methyl-isoxazol-3-ylmethyl)-1H-pyrrolo[2,3-b]pyridin-3-yl]-acetic acid;
[1-(2,4-Dimethyl-thiazol-5-ylmethyl)-2-methyl-1H-pyrrolo[2,3-b]pyridin-3-yl]-acetic acid;
[1-(2-Fluoro-benzyl)-2-methyl-1H-pyrrolo[2,3-b]pyridin-3-yl]-acetic acid;
[2-Methyl-1-(2-trifluoromethyl-benzyl)-1H-pyrrolo[2,3-b]pyridin-3-yl]-acetic acid;
[1-(3-Methoxy-benzyl)-2-methyl-1H-pyrrolo[2,3-b]pyridin-3-yl]-acetic acid;
[1-(2-Cyano-benzyl)-2-methyl-1H-pyrrolo[2,3-b]pyridin-3-yl]-acetic acid;
[2-Methyl-1-(1-phenyl-ethyl)-1H-pyrrolo[2,3-b]pyridin-3-yl]-acetic acid;
(1-Benzofuran-2-ylmethyl-2-methyl-1H-pyrrolo[2,3-b]pyridin-3-yl)-acetic acid;
{1-[1-(4-Chloro-phenyl)-ethyl]-2-methyl-1H-pyrrolo[2,3-b]pyridin-3-yl}-acetic acid;
[1-(4-Methoxy-benzyl)-2-methyl-1H-pyrrolo[2,3-b]pyridin-3-yl]-acetic acid;
[1-(2-Methoxy-benzyl)-2-methyl-1H-pyrrolo[2,3-b]pyridin-3-yl]-acetic acid;
[2-Ethyl-1-(4-trifluoromethyl-benzyl)-1H-pyrrolo[2,3-b]pyridin-3-yl]-acetic acid;
[1-(4-Ethanesulfonyl-benzyl)-2-methyl-1H-pyrrolo[2,3-b]pyridin-3-yl]-acetic acid;
[4-Chloro-1-(4-methanesulfonyl-benzyl)-2-methyl-1H-pyrrolo[2,3-b]pyridin-3-yl]-acetic acid;
[1-(2-Chloro-4-methanesulfonyl-benzyl)-2-methyl-1H-pyrrolo[2,3-b]pyridin-3-yl]-acetic acid;
[1-(4-Methanesulfonyl-3-trifluoromethyl-benzyl)-2-methyl-1H-pyrrolo[2,3-b]pyridin-3-yl]-acetic acid;
[1-(4-Ethanesulfonyl-2-trifluoromethyl-benzyl)-2-methyl-1H-pyrrolo[2,3-b]pyridin-3-yl]-acetic acid;
[1-(2-Chloro-4-ethanesulfonyl-benzyl)-2-methyl-1H-pyrrolo[2,3-b]pyridin-3-yl]-acetic acid;
[1-(4-Methanesulfonyl-2-trifluoromethyl-benzyl)-2-methyl-1H-pyrrolo[2,3-b]pyridin-3-yl]-acetic acid;
1-(4-Methanesulfonyl-benzyl)-2-methyl-1H-pyrrolo[2,3-b]pyridin-3-yl]-acetic acid;
{1-[1-(4-Methanesulfonyl-phenyl)-ethyl]-2-methyl-1H-pyrrolo[2,3-b]pyridin-3-yl}-acetic acid;
[6-Chloro-1-(4-methanesulfonyl-benzyl)-2-methyl-1H-pyrrolo[2,3-b]pyridin-3-yl]-acetic acid;
[6-Chloro-1-(4-methanesulfonyl-2-trifluoromethyl-benzyl)-2-methyl-1H-pyrrolo[2,3-b]pyridin-3-yl]-acetic acid:
{2-Methyl-1-[4-(propane-2-sulfonyl)-benzyl]-1H-pyrrolo[2,3-b]pyridin-3-yl}-acetic acid;
[1-(3-Fluoro-4-methoxy-benzyl)-2-methyl-1H-pyrrolo[2,3-b]pyridin-3-yl]-acetic acid;
[1-(4-Fluoro-3-methoxy-benzyl)-2-methyl-1H-pyrrolo[2,3-b]pyridin-3-yl]-acetic acid;
[2-Methyl-1-(6-trifluoromethyl-pyridin-3-ylmethyl)-1H-pyrrolo[2,3-b]pyridin-3-yl]-acetic acid;
[1-(3-Cyano-4-fluoro-benzyl)-2-methyl-1H-pyrrolo[2,3-b]pyridin-3-yl]-acetic acid;
[1-(2-Chloro-5-fluoro-benzyl)-2-methyl-1H-pyrrolo[2,3-b]pyridin-3-yl]-acetic acid;
[1-(4-Chloro-3-methoxy-benzyl)-2-methyl-1H-pyrrolo[2,3-b]pyridin-3-yl]-acetic acid;
[1-(4-Methanesulfonyl-2-methyl-benzyl)-2-methyl-1H-pyrrolo[2,3-b]pyridin-3-yl]-acetic acid;
[1-(4-Methoxy-benzyl)-2-methyl-1H-pyrrolo[2,3-b]pyridin-3-yl]-acetic acid;
[1-(2-Methoxy-benzyl)-2-methyl-1H-pyrrolo[2,3-b]pyridin-3-yl]-acetic acid;
{2-Methyl-1-[1-(4-trifluoromethyl-phenyl)-ethyl]-1H-pyrrolo[2,3-b]pyridin-3-yl}-acetic acid;
{1-[1-(3-Chloro-phenyl)-ethyl]-2-methyl-1H-pyrrolo[2,3-b]pyridin-3-yl}-acetic acid;
{1-[1-(4-Methanesulfonyl-phenyl)-ethyl]-2-methyl-1H-pyrrolo[2,3-b]pyridin-3-yl}-acetic acid;
1-(4-Fluoro-2-trifluoromethyl-benzyl)-2-methyl-1H-pyrrolo[2,3-b]pyridin-3-yl]-acetic acid;
[1-(2,4-Bis-trifluoromethyl-benzyl)-2-methyl-1H-pyrrolo[2,3-b]pyridin-3-yl]-acetic acid;
{2-Methyl-1-[1-(2-trifluoromethyl-phenyl)-ethyl]-1H-pyrrolo[2,3-b]pyridin-3-yl}-acetic acid;
[1-(3-Methanesulfonyl-benzyl)-2-methyl-1H-pyrrolo[2,3-b]pyridin-3-yl]-acetic acid;
[2-Methyl-1-(4-nitro-benzyl)-1H-pyrrolo[2,3-b]pyridin-3-yl]-acetic acid;
[1-(4-Bromo-benzyl)-2-methyl-1H-pyrrolo[2,3-b]pyridin-3-yl]-acetic acid;
[1-(3-Chloro-4-methanesulfonyl-benzyl)-2-methyl-1H-pyrrolo[2,3-b]pyridin-3-yl]-acetic acid; and
[1-(3-Fluoro-4-methanesulfonyl-benzyl)-2-methyl-1H-pyrrolo[2,3-b]pyridin-3-yl]-acetic acid.

5. A compound in free or salt form selected from:
[2-Methyl-1-(2-trifluoromethyl-benzyl)-1H-pyrrolo[2,3-b]pyridin-3-yl]-acetic acid;

[4-Chloro-1-(4-methanesulfonyl-benzyl)-2-methyl-1H-pyrrolo[2,3-b]pyridin-3-yl]-acetic acid;

[1-(2-Chloro-4-methanesulfonyl-benzyl)-2-methyl-1H-pyrrolo[2,3-b]pyridin-3-yl]-acetic acid;

[1-(4-Ethanesulfonyl-2-trifluoromethyl-benzyl)-2-methyl-1H-pyrrolo[2,3-b]pyridin-3-yl]-acetic acid;

[1-(2-Chloro-4-ethanesulfonyl-benzyl)-2-methyl-1H-pyrrolo[2,3-b]pyridin-3-yl]-acetic acid;

[1-(4-Methanesulfonyl-2-trifluoromethyl-benzyl)-2-methyl-1H-pyrrolo[2,3-b]pyridin-3-yl]-acetic acid;

1-(4-Methanesulfonyl-benzyl)-2-methyl-1H-pyrrolo[2,3-b]pyridin-3-yl]-acetic acid;

{1-[1-(4-Methanesulfonyl-phenyl)-ethyl]-2-methyl-1H-pyrrolo[2,3-b]pyridin-3-yl}-acetic acid;

[6-Chloro-1-(4-methanesulfonyl-benzyl)-2-methyl-1H-pyrrolo[2,3-b]pyridin-3-yl]-acetic acid;

[6-Chloro-1-(4-methanesulfonyl-2-trifluoromethyl-benzyl)-2-methyl-1H-pyrrolo[2,3-b]pyridin-3-yl]-acetic acid;

[1-(3-Chloro-4-methanesulfonyl-benzyl)-2-methyl-1H-pyrrolo[2,3-b]pyridin-3-yl]-acetic acid; and

[1-(3-Fluoro-4-methanesulfonyl-benzyl)-2-methyl-1H-pyrrolo[2,3-b]pyridin-3-yl]-acetic acid.

6. A pharmaceutical composition, comprising:
the compound according to claim 5, and
pharmaceutical acceptable carrier.

7. The compound in free or salt form of claim 5 represented by [2-Methyl-1-(2-trifluoromethyl-benzyl)-1H-pyrrolo[2,3-b]pyridin-3-yl]-acetic acid.

8. The compound in free or salt form of claim 5 represented by [1-(2-Chloro-4-ethanesulfonyl-benzyl)-2-methyl-1H-pyrrolo[2,3-b]pyridin-3-yl]-acetic acid.

9. The compound in free or salt form of claim 5 represented by [1-(4-Methanesulfonyl-2-trifluoromethyl-benzyl)-2-methyl-1H-pyrrolo[2,3-b]pyridin-3-yl]-acetic acid.

10. The compound in free or salt form of claim 5 represented by 1-(4-Methanesulfonyl-benzyl)-2-methyl-1H-pyrrolo[2,3-b]pyridin-3-yl]-acetic acid.

11. The compound in free or salt form of claim 5 represented by {1-[1-(4-Methanesulfonyl-phenyl)-ethyl]-2-methyl-1H-pyrrolo[2,3-b]pyridin-3-yl}-acetic acid.

12. The compound in free or salt form of claim 5 represented by [1-(3-Chloro-4-methanesulfonyl-benzyl)-2-methyl-1H-pyrrolo[2,3-b]pyridin-3-yl]-acetic acid.

13. The compound in free or salt form of claim 5 represented by [1-(3-Fluoro-4-methanesulfonyl-benzyl)-2-methyl-1H-pyrrolo[2,3-b]pyridin-3-yl]-acetic acid.

\* \* \* \* \*